US012686713B2

(12) United States Patent
Alonso et al.

(10) Patent No.: US 12,686,713 B2
(45) Date of Patent: Jul. 21, 2026

(54) METHODS FOR TREATING COMPLEMENT-MEDIATED DISEASES

(71) Applicant: Bioverativ USA Inc., Waltham, MA (US)

(72) Inventors: Miguel Alonso Alonso, Somerville, MA (US); Nazem Atassi, Newton, MA (US); Rene Belder, Hopewell, NJ (US); Timothy Wing Yau Chow, Boston, MA (US); Pirouz Shamszad, Basking Ridge, NJ (US); Michael John Storek, Cambridge, MA (US); Christopher Lawrence Vinnard, Pennington, NJ (US); Erik Holger Wallstroem, Boston, MA (US); Yu Jyu Nancy Wong, North Andover, MA (US)

(73) Assignee: Bioverativ USA Inc., Waltham, MA (US)

( * ) Notice: Subject to any disclaimer, the term of this patent is extended or adjusted under 35 U.S.C. 154(b) by 47 days.

(21) Appl. No.: 18/340,797

(22) Filed: Jun. 23, 2023

(65) Prior Publication Data

US 2024/0025978 A1       Jan. 25, 2024

Related U.S. Application Data

(60) Provisional application No. 63/379,626, filed on Oct. 14, 2022, provisional application No. 63/375,041, filed on Sep. 8, 2022, provisional application No. 63/370,484, filed on Aug. 4, 2022, provisional application No. 63/355,296, filed on Jun. 24, 2022.

(51) Int. Cl.
| | |
|---|---|
| *C07K 16/18* | (2006.01) |
| *A61K 39/00* | (2006.01) |
| *A61P 7/06* | (2006.01) |

(52) U.S. Cl.
CPC ................ *C07K 16/18* (2013.01); *A61P 7/06* (2018.01); *A61K 2039/505* (2013.01); *A61K 2039/54* (2013.01); *A61K 2039/545* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 4,945,039 | A | 7/1990 | Suzuki et al. |
| 4,946,778 | A | 8/1990 | Ladner et al. |
| 5,225,539 | A | 7/1993 | Winter |
| 5,476,786 | A | 12/1995 | Huston et al. |
| 5,514,548 | A | 5/1996 | Krebber et al. |
| 5,585,097 | A | 12/1996 | Bolt et al. |
| 5,624,821 | A | 4/1997 | Winter et al. |
| 5,648,260 | A | 7/1997 | Winter et al. |
| 5,677,425 | A | 10/1997 | Bodmer et al. |
| 5,869,046 | A | 2/1999 | Presta et al. |
| 6,090,777 | A | 7/2000 | Hack et al. |
| 6,121,022 | A | 9/2000 | Presta et al. |
| 6,165,745 | A | 12/2000 | Ward et al. |
| 6,194,551 | B1 | 2/2001 | Idusogie et al. |
| 6,277,375 | B1 | 8/2001 | Ward |
| 6,737,056 | B1 | 5/2004 | Presta |
| 7,049,282 | B2 | 5/2006 | Frank et al. |
| 7,071,299 | B2 | 7/2006 | West et al. |
| 7,563,441 | B2 | 7/2009 | Graus et al. |
| 7,658,921 | B2 | 2/2010 | Dall |
| 7,666,627 | B2 | 2/2010 | Gal et al. |
| 7,897,561 | B2 | 3/2011 | Kotwal et al. |
| 7,919,094 | B2 | 4/2011 | Schwaeble et al. |
| 7,923,010 | B2 | 4/2011 | Christadoss et al. |
| 8,071,532 | B2 | 12/2011 | Mannesse et al. |
| 8,148,330 | B2 | 4/2012 | Barres et al. |
| 8,163,881 | B2 | 4/2012 | Ober |

(Continued)

FOREIGN PATENT DOCUMENTS

| | | | |
|---|---|---|---|
| BR | 112017021289 A2 | 6/2018 |
| CA | 1276103 C | 11/1990 |

(Continued)

OTHER PUBLICATIONS

Hughes et al. Phase 2 Proof-of-concept trial design for BIVV020, a monoclonal antibody targeting complement C1s, in CIDP. Journal of the Peripheral Nervous System, (Sep. 2021) vol. 26, No. 3, pp. 355. Abstract No. 111. Virtual. Jun. 12, 2021-Jun. 27, 2021. (Year: 2021).*
NCT04658472 Trail. Proof-of-concept Study for BIVV020 in Chronic Inflammatory Demyelinating Polyneuropathy (CIDP) (Viewing V7 (May 25, 2021). (Year: 2021).*
CTR20210677. Shanghai BIVV020 Phase II Clinical Trial— BIVV020 proof-of-conc study for the treatment of chronic inflammatory demyelinatin polyradiculoneuropathy (CIDP). Sanofi, pp. 1-8, Apr. 2, 2021. (Year: 2021).*
NCT04669600. A multicenter, Phase 2a, open-label, non-randomized study evaluating the efficacy, safety, and tolerability of BIVV020 in adults with persistent/chronic immune thrombocytopenia (ITP). Sanofi, pp. 1-87. Jan. 25, 2021. (Year: 2021).*

(Continued)

*Primary Examiner* — Maher M Haddad
(74) *Attorney, Agent, or Firm* — Wolf, Greenfield & Sacks, P.C.

(57) ABSTRACT
Provided herein are methods of treating cold agglutinin disease (CAD) or chronic inflammatory demyelinating polyneuropathy (CIDP) in a subject in need thereof. The methods comprise administering to a subject a humanized antibody that specifically binds complement component C1s (anti-C1s antibody). Methods of treating CAD comprise administering the anti-C1s antibody to a subject in a fixed dose. Methods of treating CIDP comprise administering to a subject a weight-based loading dose of the anti-C1s antibody followed by one or more fixed maintenance doses. The methods comprise administering an effective dose of anti-C1s antibody to achieve a minimum level of CP inhibition for therapeutic effect.

18 Claims, 29 Drawing Sheets

Specification includes a Sequence Listing.

(56) References Cited

U.S. PATENT DOCUMENTS

| | | | |
|---|---|---|---|
| 8,221,756 | B2 | 7/2012 | Fung et al. |
| 8,329,169 | B2 | 12/2012 | Fung et al. |
| 8,415,288 | B2 | 4/2013 | Mannesse et al. |
| 8,501,705 | B2 | 8/2013 | Christadoss et al. |
| 8,545,850 | B2 | 10/2013 | Chen et al. |
| 8,591,886 | B2 | 11/2013 | Ponath et al. |
| 8,877,197 | B2 | 11/2014 | van Vlasselaer et al. |
| 8,945,562 | B2 | 2/2015 | van Vlasselaer et al. |
| 9,074,003 | B2 | 7/2015 | van Vlasselaer et al. |
| 9,074,004 | B2 | 7/2015 | van Vlasselaer et al. |
| 9,206,259 | B2 | 12/2015 | van Vlasselaer et al. |
| 9,512,233 | B2 | 12/2016 | van Vlasselaer et al. |
| 9,562,092 | B2 | 2/2017 | van Vlasselaer et al. |
| 9,562,106 | B2 | 2/2017 | van Vlasselaer et al. |
| 10,450,382 | B2 | 10/2019 | van Vlasselaer et al. |
| 10,457,745 | B2 | 10/2019 | van Vlasselaer et al. |
| 10,729,767 | B2 | 8/2020 | Panicker et al. |
| 11,246,926 | B2 | 2/2022 | Panicker et al. |
| 12,215,169 | B2 | 2/2025 | van Vlasselaer et al. |
| 12,240,917 | B2 | 3/2025 | Van Vlasselaer et al. |
| 12,391,750 | B2 | 8/2025 | Panicker et al. |
| 2002/0010948 | A1 | 1/2002 | Patience |
| 2002/0037915 | A1 | 3/2002 | Illig et al. |
| 2002/0102256 | A1 | 8/2002 | West et al. |
| 2003/0190311 | A1 | 10/2003 | Dall'Acqua et al. |
| 2004/0115194 | A1 | 6/2004 | Wang |
| 2004/0219147 | A1 | 11/2004 | Bell |
| 2005/0004031 | A1 | 1/2005 | Subasinghe et al. |
| 2005/0032157 | A1 | 2/2005 | Gal et al. |
| 2005/0079174 | A1 | 4/2005 | Barbera-Guillem et al. |
| 2005/0136494 | A1 | 6/2005 | Akita et al. |
| 2005/0177882 | A1 | 8/2005 | Gavin et al. |
| 2005/0222027 | A1 | 10/2005 | Chiang et al. |
| 2005/0267035 | A1 | 12/2005 | West et al. |
| 2005/0271660 | A1 | 12/2005 | Wang |
| 2006/0002937 | A1 | 1/2006 | Schwaeble et al. |
| 2006/0008883 | A1 | 1/2006 | Lazar et al. |
| 2006/0018896 | A1 | 1/2006 | Schwaeble et al. |
| 2006/0148015 | A1 | 7/2006 | Roos et al. |
| 2006/0173170 | A1 | 8/2006 | Chamberlain et al. |
| 2007/0172483 | A1 | 7/2007 | Schwaeble et al. |
| 2008/0075712 | A1 | 3/2008 | Hattori et al. |
| 2008/0160015 | A1 | 7/2008 | Gilles et al. |
| 2008/0167449 | A1 | 7/2008 | Lazar et al. |
| 2008/0206242 | A1 | 8/2008 | Lawrence et al. |
| 2008/0233113 | A1 | 9/2008 | Bansal |
| 2009/0163699 | A1 | 6/2009 | Chamberlain et al. |
| 2009/0259019 | A1 | 10/2009 | Willis et al. |
| 2009/0269356 | A1 | 10/2009 | Epstein et al. |
| 2009/0324585 | A1 | 12/2009 | Robinson et al. |
| 2010/0074899 | A1 | 3/2010 | Schwaeble et al. |
| 2010/0143343 | A1 | 6/2010 | Halstead et al. |
| 2010/0143344 | A1 | 6/2010 | Baas et al. |
| 2010/0166862 | A1 | 7/2010 | Francois et al. |
| 2011/0002931 | A1 | 1/2011 | Tamburini |
| 2011/0020337 | A1 | 1/2011 | Schwaeble et al. |
| 2011/0081347 | A1 | 4/2011 | Gorlatov |
| 2011/0091450 | A1 | 4/2011 | Schwaeble et al. |
| 2011/0104156 | A1 | 5/2011 | Christadoss et al. |
| 2011/0190221 | A1 | 8/2011 | Francois et al. |
| 2011/0263436 | A1 | 10/2011 | Tu et al. |
| 2011/0281757 | A1 | 11/2011 | Tyan et al. |
| 2011/0311549 | A1 | 12/2011 | Schwaeble et al. |
| 2011/0311550 | A1 | 12/2011 | Law et al. |
| 2011/0312505 | A1 | 12/2011 | Reddy et al. |
| 2012/0195880 | A1 | 8/2012 | Barres et al. |
| 2012/0225056 | A1 | 9/2012 | Rother et al. |
| 2012/0230953 | A1 | 9/2012 | Goldenberg et al. |
| 2012/0244139 | A1 | 9/2012 | Madison et al. |
| 2012/0251549 | A1 | 10/2012 | Fung et al. |
| 2012/0258095 | A1 | 10/2012 | Demopulos et al. |
| 2012/0263717 | A1 | 10/2012 | Dennis et al. |
| 2012/0282263 | A1 | 11/2012 | Dudler et al. |
| 2012/0308566 | A1 | 12/2012 | Martin et al. |
| 2012/0309943 | A1 | 12/2012 | Kumada et al. |
| 2012/0315266 | A1 | 12/2012 | Olson et al. |
| 2012/0328601 | A1 | 12/2012 | Barres et al. |
| 2013/0064820 | A1 | 3/2013 | Magro |
| 2013/0078245 | A1 | 3/2013 | Holers et al. |
| 2013/0123473 | A1 | 5/2013 | Goldenberg et al. |
| 2013/0202612 | A1 | 8/2013 | Lin et al. |
| 2013/0203678 | A1 | 8/2013 | Francois et al. |
| 2013/0224187 | A1 | 8/2013 | Rother et al. |
| 2013/0237589 | A1 | 9/2013 | Benedict et al. |
| 2013/0244941 | A1 | 9/2013 | Mannesse et al. |
| 2013/0259860 | A1 | 10/2013 | Smith et al. |
| 2013/0261287 | A1 | 10/2013 | Sabbadini et al. |
| 2013/0273052 | A1 | 10/2013 | Gies et al. |
| 2013/0281677 | A1 | 10/2013 | Wilson et al. |
| 2014/0127196 | A1 | 5/2014 | van Vlasselaer et al. |
| 2014/0127208 | A1 | 5/2014 | van Vlasselaer et al. |
| 2014/0140933 | A1 | 5/2014 | van Vlasselaer et al. |
| 2014/0220014 | A1 | 8/2014 | Dillon et al. |
| 2014/0294812 | A1 | 10/2014 | Lazar |
| 2014/0357843 | A1 | 12/2014 | Oh et al. |
| 2015/0259437 | A1 | 9/2015 | van Vlasselaer et al. |
| 2015/0329645 | A1 | 11/2015 | van Vlasselaer et al. |
| 2016/0090425 | A1 | 3/2016 | Rosenthal et al. |
| 2016/0159890 | A1 | 6/2016 | Rosenthal et al. |
| 2016/0326237 | A1 | 11/2016 | Rosenthal et al. |
| 2017/0226229 | A1 | 8/2017 | van Vlasselaer et al. |
| 2017/0226230 | A1 | 8/2017 | van Vlasselaer et al. |
| 2017/0304439 | A1 | 10/2017 | Guettner et al. |
| 2018/0092974 | A1 | 4/2018 | Panicker et al. |
| 2018/0169240 | A1 | 6/2018 | Parry et al. |
| 2018/0280500 | A1* | 10/2018 | Ming ................. A61K 39/0008 |
| 2019/0175663 | A1 | 6/2019 | Choe et al. |
| 2020/0048332 | A1 | 2/2020 | Panicker et al. |
| 2020/0079875 | A1 | 3/2020 | van Vlasselaer et al. |
| 2020/0079876 | A1 | 3/2020 | van Vlasselaer et al. |
| 2020/0140533 | A1 | 5/2020 | Rosi et al. |
| 2020/0405852 | A1 | 12/2020 | Panicker et al. |
| 2021/0115116 | A1 | 4/2021 | van Vlasselaer et al. |
| 2022/0185912 | A1 | 6/2022 | van Vlasselaer et al. |
| 2022/0204647 | A1 | 6/2022 | van Vlasselaer et al. |
| 2022/0249664 | A1 | 8/2022 | Parry et al. |
| 2023/0218753 | A1 | 7/2023 | Panicker et al. |
| 2023/0357433 | A1 | 11/2023 | Arias et al. |
| 2024/0052062 | A1 | 2/2024 | Hobbs et al. |
| 2024/0076363 | A1 | 3/2024 | Panicker et al. |
| 2024/0117021 | A1 | 4/2024 | Patke et al. |
| 2025/0145696 | A1 | 5/2025 | Van Vlasselaer et al. |
| 2025/0188192 | A1 | 6/2025 | van Vlasselaer et al. |
| 2025/0263503 | A1 | 8/2025 | van Vlasselaer et al. |
| 2025/0295768 | A1 | 9/2025 | Parry et al. |

FOREIGN PATENT DOCUMENTS

| | | |
|---|---|---|
| CN | 101298481 A | 11/2008 |
| CN | 102170906 A | 8/2011 |
| CN | 102203610 A | 9/2011 |
| CN | 102459334 A | 5/2012 |
| CN | 104870475 A | 8/2015 |
| CN | 104884088 A | 9/2015 |
| CN | 105143261 A | 12/2015 |
| CN | 108348600 A | 7/2018 |
| CN | 110300520 A | 10/2019 |
| CN | 110753701 A | 2/2020 |
| CO | 2017011238 A2 | 1/2018 |
| EA | 201890106 A1 | 5/2018 |
| EA | 201990884 A1 | 10/2019 |
| EP | 0125023 B1 | 6/1991 |
| EP | 0519596 A1 | 12/1992 |
| EP | 0120694 B1 | 7/1993 |
| EP | 0194276 B1 | 8/1993 |
| EP | 0239400 B1 | 8/1994 |
| EP | 2 266 606 A1 | 12/2010 |
| JP | S61271455 A | 12/1986 |
| JP | 2007-535474 A | 12/2007 |
| JP | 2008-533156 A | 8/2008 |
| JP | 2012-510282 | 5/2012 |
| JP | 2013-136530 A | 7/2013 |
| JP | 2016-503400 | 2/2016 |
| JP | 2016-505240 | 2/2016 |

(56) References Cited

FOREIGN PATENT DOCUMENTS

| | | |
|---|---|---|
| JP | 2016-520313 | 7/2016 |
| JP | 6538561 B2 | 7/2019 |
| JP | 6543572 B2 | 7/2019 |
| JP | 2020-502996 A | 1/2020 |
| JP | 6691183 B2 | 4/2020 |
| JP | 6889308 B1 | 5/2021 |
| JP | 7069138 B2 | 5/2022 |
| TW | I773695 B | 8/2022 |
| WO | WO 1986/001533 A1 | 3/1986 |
| WO | WO 1993/006213 A1 | 4/1993 |
| WO | WO 1994/029351 A2 | 12/1994 |
| WO | WO 1997/034631 A1 | 9/1997 |
| WO | WO 1998/023289 A1 | 6/1998 |
| WO | WO 2000/042072 A2 | 7/2000 |
| WO | WO 2001/57079 A2 | 8/2001 |
| WO | WO 2002/060919 A2 | 8/2002 |
| WO | WO 2003/009803 A2 | 2/2003 |
| WO | WO 2005/056759 A2 | 6/2005 |
| WO | WO 2006/101860 A1 | 9/2006 |
| WO | WO 2007/022416 A2 | 2/2007 |
| WO | WO 2008/060645 A2 | 5/2008 |
| WO | WO 2008/074227 A1 | 6/2008 |
| WO | WO 2009/086320 A1 | 7/2009 |
| WO | WO 2011/102342 A1 | 8/2011 |
| WO | WO 2012/028622 A2 | 3/2012 |
| WO | WO 2013/093027 A1 | 6/2013 |
| WO | WO 2014/066744 A2 | 5/2014 |
| WO | WO 2014/071206 A1 | 5/2014 |
| WO | WO 2014/186599 A2 | 11/2014 |
| WO | WO 2015/004052 A1 | 1/2015 |
| WO | WO 2015/084999 A1 | 6/2015 |
| WO | WO 2016/059512 A1 | 4/2016 |
| WO | WO 2016/164358 A1 | 10/2016 |
| WO | WO 2016/193346 A1 | 12/2016 |
| WO | WO 2016/193348 A1 | 12/2016 |
| WO | WO 2016/193352 A1 | 12/2016 |
| WO | WO 2016/193353 A1 | 12/2016 |
| WO | WO 2016/193355 A1 | 12/2016 |
| WO | WO 2016/210172 A1 | 12/2016 |
| WO | WO 2018/071676 A1 | 4/2018 |
| WO | WO 2018/170145 A1 | 9/2018 |
| WO | WO 2018/204368 A1 | 11/2018 |
| WO | WO 2019/198807 A1 | 10/2019 |
| WO | WO 2020/081408 A1 | 4/2020 |
| WO | WO 2022/031978 A1 | 2/2022 |

OTHER PUBLICATIONS

PDY16894-ITP. A multicenter, phase 2a, open label, non-randomized study evaluating the efficacy, safety, and tolerability of BIVV020 in adult with persistent/chronic immune thrombocytopenia (ITP). NHS, Health Research Authority. pp. 1-3, Dec. 21, 2020. (Year: 2020).*

NL-OMON54382. A Phase 2, multicenter, open-label, nonrandomized, proof-of-concept study evaluating the efficacy, safety, and tolerability of SAR445088 (previously BIVV020) in . . . demyelinating polyneuropathy (CIDP). p. 1-11, published Jan. 19, 2021 and last updated Jan. 9, 2025. (Year: 2025).*

Statistical Analysis Plan SAR445088(BIVV020)—PDY16894, A multicenter, Phase 2a, open-label, non-randomized study evaluating the efficacy, safety, and tolerability of BIW020 in adults with persistent/chronic immune thrombocytopenia (ITP). p. 1-30, Sep. 30, 2021 (Year: 2021).*

International Preliminary Report on Patentability in connection with Application No. PCT/US2022/022745 mailed Oct. 12, 2023.

International Preliminary Report on Patentability for PCT/US2023/068420 mailed Dec. 26, 2024.

International Search Report and Written Opinion in connection with Application No. PCT/US2023/069027 mailed Nov. 7, 2023.

International Preliminary Report on Patentability for PCT/US2023/069027 mailed Jan. 2, 2025.

Chester et al., Clinical issues in antibody design. Trends Biotechnol. Aug. 1995;13(8):294-300. doi: 10.1016/S0167-7799(00)88968-4.

Chow et al., First-in-human study with SAR445088: A novel selective classical complement pathway inhibitor. Clin Transl Sci. Apr. 2023; 16(4):673-685. doi: 10.1111/cts.13481. Epub Feb. 2, 2023.

Cooper, The classical complement pathway: activation and regulation of the first complement component. Adv Immunol. 1985;37:151-216. doi: 10.1016/s0065-2776(08)60340-5.

Dunkelberger et al., Complement and its role in innate and adaptive immune responses. Cell Res. Jan. 2010;20(1):34-50. doi: 10.1038/cr.2009.139. Epub Dec. 15, 2009.

Gelbenegger et al., Inhibition of complement C1s in patients with cold agglutinin disease: lessons learned from a named patient program. Blood Adv. Mar. 24, 2020;4(6):997-1005. doi: 10.1182/bloodadvances.2019001321.

Hamano et al., High Serum IgG4 Concentrations in Patients with Sclerosing Pancreatitis, 2001, New England Journal of Medicine, vol. 344, No. 10, pp. 732-738 (Year: 2001).

Nesargikar et al., The complement system: history, pathways, cascade and inhibitors. Eur J Microbiol Immunol (Bp). Jun. 2012;2(2):103-11. doi: 10.1556/EuJMI.2.2012.2.2. Epub Jun. 13, 2012.

Querol et al., An innovative phase 2 proof-of-concept trial design to evaluate SAR445088, a monoclonal antibody targeting complement C1s in chronic inflammatory demyelinating polyneuropathy. J Peripher Nerv Syst. Jun. 2023;28(2):276-285. doi: 10.1111/jns.12551. Epub May 31, 2023.

Querol et al., Preliminary Efficacy and Safety Data from the Phase 2 Trial of Riliprubart (SAR445088), a Humanized Monoclonal Antibody Targeting Complement C1s, in Chronic Inflammatory Demyelinating Polyneuropathy (CIDP). Neurology. Apr. 2024;102(17):Supp. Supplement 1. Abstract No. S15.008. 11 pages.

Svačina et al., Chronic Inflammatory Demyelinating Polyneuropathy (CIDP): Current Therapies and Future Approaches. Curr Pharm Des. 2022;28(11):854-862. doi: 10.2174/1381612828666220325102840.

Partial Supplementary European Search Report in connection with Application No. EP 20156431.7 mailed Aug. 21, 2020.

Extended European Search Report in connection with Application No. EP 20156431.7 mailed Nov. 26, 2020.

International Search Report and Written Opinion in connection with Application No. PCT/US2013/066783 mailed May 5, 2014.

International Preliminary Report on Patentability in connection with Application No. PCT/US2013/066783 mailed May 7, 2015.

Extended European Search Report in connection with Application No. EP 21157955.2 mailed Aug. 31, 2021.

International Search Report and Written Opinion in connection with Application No. PCT/US2016/026038 mailed Aug. 30, 2016.

International Preliminary Report on Patentability in connection with Application No. PCT/US2016/026038 mailed Oct. 19, 2017.

Extended European Search Report in connection with Application No. EP 22207626.7 mailed on Jun. 15, 2023.

Partial Supplementary European Search Report in connection with Application No. EP 16815332.8 mailed on Feb. 12, 2019.

Extended European Search Report in connection with Application No. EP 16815332.8 mailed on May 15, 2019.

International Search Report and Written Opinion in connection with Application No. PCT/US2016/039087 mailed Oct. 4, 2016.

International Preliminary Report on Patentability in connection with Application No. PCT/US2016/039087 mailed Jan. 4, 2018.

Extended European Search Report in connection with Application No. EP 17859451.1 mailed May 13, 2020.

International Search Report and Written Opinion in connection with Application No. PCT/US2017/056349 mailed Jan. 23, 2018.

International Preliminary Report on Patentability in connection with Application No. PCT/US2017/056349 mailed Apr. 25, 2019.

International Search Report and Written Opinion in connection with Application No. PCT/US2018/022462 mailed Jun. 12, 2018.

International Preliminary Report on Patentability in connection with Application No. PCT/US2018/022462 mailed Sep. 26, 2019.

International Search Report and Written Opinion for PCT/US2021/044761 mailed Nov. 30, 2021.

International Preliminary Report on Patentability for PCT/US2021/044761 mailed Feb. 16, 2023.

(56) References Cited

OTHER PUBLICATIONS

International Search Report and Written Opinion in connection with Application No. PCT/US2022/022745 mailed Jul. 1, 2022.

International Search Report and Written Opinion in connection with Application No. PCT/US2023/068420 mailed Sep. 22, 2023.

[No Author Listed], ClinicalTrials.gov Identifier: NCT03347422. A Study to Assess the Efficacy and Safety of BIVV009 (Sutimlimab) in Participants With Primary Cold Agglutinin Disease Without A Recent History of Blood Transfusion (Cadenza). Sep. 1, 2020. https://clinicaltrials.gov/ct2/history/NCT03347422?V_54= View#StudyPageTop [last accessed Jun. 22, 2022]. pp. 7-13.

[No Author Listed] True North Therapeutics: Study NCT02502903. Jul. 14, 2016 (v3). Retrieved from the Internet: https://clinicaltrials. gov/ct2/history/NCT02502903?V_1=View#StudyPageTop on May 23, 2018. 7 pages.

Almagro et al., "Humanization of Antibodies," Frontiers in Bioscience 13:1619-1633, Frontiers In Bioscience Publications, United States (2008).

An et al., "IgG2m4, an Engineered Antibody Isotype with Reduced Fe function," Mabs 1(6):572-579, Philadelphia, PA : Taylor & Francis, United States (Nov.-Dec. 2009).

Angal et al., A single amino acid substitution abolishes the heterogeneity of chimeric mouse/human (IgG4) antibody. Mol Immunol. Jan. 1993;30(1):105-8.

Anti-Complement C1 s Antibody [clone 2011], Cat# LS-C173719, Lifespan Biosciences, accessed at http://www.lsbio.com/antibodies/ anti-complement-c1s-antibody-clone-2d11-mouse-anti-humanmonoclonal-for-ihc-western-blot-ls-c173719/181143, 2014.

Anti-Complement C1 s Antibody [clone 2A8], Cat# LS-C173720, Lifespan Biosciences, accessed at http://www.lsbio.com/antibodies/ anti-complement-cls-anti body-clone-2a8-mouse-anti-human-monoclonal-for-ihewestern-blot-ls-c173720/181144, 2014.

Anti-Complement C1 s Antibody [clone 2F5], Cat# LS-C173425, Lifespan Biosciences, accessed at http://www.lsbio.com/antibodies/ anti-complement-cls-antibody-ciane-2f5-mouse-anti-human-monoclonalfor-western-blot-ls-c173425/180849, 2014.

Anti-Complement C1 s Antibody [clone 409], Cat# LS-C173424, Lifespan Biosciences, accessed at http://www.lsbio.com/antibodies/ anti-complement-c1s-antibody-ciane-4d9-mouse-anti-human-monoclonal-for-western-blot-ls-c173424/180848, 2014.

Anti-Complement C1 s Antibody [clone 49], Cat# LS-C6209, Lifespan Biosciences, accessed at http://www.lsbio.com/antibodies/ anti-complement-cls-antibody-ciane-49-mouse-anti-human-monoclonalls-c6209/6950, 2014.

Anti-Complement C1 s Antibody [clone 5F2], Cat# LS-C173718, Lifespan Biosciences, accessed at http://www.lsbio.com/antibodies/ anti-complement-c1s-antibody-clone-5f2-mouse-anti-human-monoclonal-for-ihc-western-blot-ls-c173718/181142, 2014.

Anti-Complement C1 s Antibody, Cat# LS-C121168, Lifespan Biosciences, accessed at http://www.lsbio.com/antibodies/anti-complement-c1s-antibody-mouse-anti-human-monoclonal-for-ihc-western-blot-ls-c121168/124626, 2014.

Anti-Complement C1 s Antibody, Cat# LS-C6208, Lifespan Biosciences, accessed at http://www.lsbio.com/antibodies/anticomplement-c1s-antibody-mouse-anti-human-monoclonal-ls-c6208/6949, 2014.

Anti-Complement C1s Antibody (aa1-688), Cat# LS-C128271, Lifespan Biosciences, accessed at http://www.lsbio.com/antibodies/anticomplement-c1s-antibody-aa1-688-mouse-anti-human-polyclonalfor-western-blot-ls-c128271 /131891, 2014.

Anti-Complement C1s Antibody (Internal) [clone EPR9066(B)], Cat# LS-C154717, Lifespan Biosciences, accessed at http://www. lsbio.com/antibodies/anti-complement-c1s-antibody-internal-cloneepr9066b-rabbit-anti-human-monoclonal-for-ihc-western-blot-lsc154717/161392, 2014.

Anti-Complement C1s Antibody (Internal) [clone EPR9067(B)], Cat# LS-C154704, Lifespan Biosciences, accessed at http://www. lsbio.com/antibodies/anti-complement-c1s-antibody-internal-cloneepr9067b-rabbit-anti-human-monoclonal-for-western-blot-ls-c154704/ 161379, 2014.

Anti-Complement C1s Antibody [clone M81], Cat# LS-C140039, accessed at Lifespan Biosciences, accessed at http://www.lsbio.com/ antibodies/anti-complement-c1s-antibody-clone-m81-mouse-antihuman-monoclonal-for-ihc-western-blot-ls-c140039/144752, 2014.

Anti-Complement C1 s Antibody [clone 401 0], Cat# LS-C173540, Lifespan Biosciences, accessed at http://www.lsbio.com/antibodies/ anti-complement-c1s-anti body-clone-4d10-mouse-anti-human-monoclonal-for-westernblot-ls-c173540/180964, 2014.

Bai et al., A guide to rational dosing of monoclonal antibodies. Clin Pharmacokinet. Feb. 1, 2012;51(2):119-35. doi: 10.2165/11596370-000000000-00000.

Baker et al., Immunogenicity of protein therapeutics: The key causes, consequences and challenges. Self Nonself. Oct. 2010;1(4):314-322. doi: 10.4161/self.1.4.13904.

Basiglio et al., "Complement Activation and Disease: Protective Effects of Hyperbilirubinaemia," Clinical Science 118(2):99-113, London : Portland Press on behalf of the Medical Research Society and the Biochemical Society, England (Oct. 2009).

Baynes et al., Role of arginine in the stabilization of proteins against aggregation. Biochemistry. Mar. 29, 2005;44(12):4919-25. doi: 10.1021/bi047528r.

Berentsen et al., Novel insights into the treatment of complement-mediated hemolytic anemias. Ther Adv Hematol. Sep. 9, 2019;10:2040620719873321. doi: 10.1177/2040620719873321.

Brahmi et al., "Synergistic Inhibition of Human Cell-Mediated Cytotoxicity by Complement Component Antisera Indicates That Target Cell Lysis May Result From an Enzymatic Cascade Involving Granzymes and Perforin," Nature Immunology 14(5-6):271-285, New York : S. Karger, Switzerland (Sep. 1995).

Brown et al., Tolerance of single, but not multiple, amino acid replacements in antibody VH CDR 2: a means of minimizing B cell wastage from somatic hypermutation? J Immunol. May 1, 1996;156(9):3285-91.

Caldas et al., "Humanization of the anti-CD18 antibody 6.7: an unexpected effect of a framework residue in binding to antigen," Mol. Immunol., 39(15):941-952 (2003) (Elsevier Pub., Cambridge, MA).

Carroll "Strategies for Generating Therapeutic Antibodies," Dissertation, The University of Texas at Austin, 170 pages (Aug. 2012).

Carroll et al., "Antibody-Mediates Inhibition of Human C1s and the Classical Complement Pathway," Immunobiology 218(8):1041-1048, Amsterdam : Elsevier, Netherlands (Aug. 2013).

Chen et al., "Enhancement and Destruction of Antibody Function by Somatic Mutation: Unequal Occurrence Is Controlled by V Gene Combinatorial Associations," The EMBO Journal 14(12):2784-2794, Wiley Blackwell, England (1995).

Colman, "Effects of Amino Acid Sequence Changes on Antibody-antigen Interactions," Research in Immunology 145(1):33-36, Elsevier, France (Jan. 1994).

Collett, J. "Dosage Regimens", Jan. 1, 2001 (Jan. 1, 2001), Pharmaceutics. The Science Of Dosage Form Design Ed. 2, Churchill Livingstone, pp. 275-288, Xp003030862, Isbn: 978-0-443-05517-1.

D'Angelo et a., Many Routes to an Antibody Heavy-Chain CDR3: Necessary, Yet Insufficient, for Specific Binding. Front Immunol. Mar. 8, 2018;9:395. doi: 10.3389/fimmu.2018.00395. eCollection 2018.

Datta-Mannan et al., The interplay of non-specific binding, target-mediated clearance and FcRn interactions on the pharmacokinetics of humanized antibodies. MAbs. 2015;7(6):1084-93. doi: 10.1080/ 19420862.2015.1075109. Epub Sep. 4, 2015.

Derhaschnig et al., Combined integrated protocol/basket trial design for a first-in-human trial. Orphanet J Rare Dis. Oct. 4, 2016;11(1):134.

Dmytrijuk et al., FDA report: eculizumab (Soliris) for the treatment of patients with paroxysmal nocturnal hemoglobinuria. Oncologist. Sep. 2008;13(9):993-1000. doi: 10.1634/theoncologist.2008-0086. Epub Sep. 10, 2008.

Doevendans et al., Immunogenicity of Innovative and Biosimilar Monoclonal Antibodies. Antibodies (Basel). Mar. 5, 2019;8(1):21. doi: 10.3390/antib8010021.

Du et al., "Molecular basis of recognition of human osteopontin by 23C3, a potential therapeutic antibody for treatment of rheumatoid arthritis," J Mol. Biol., 382(4):835-842 (2008), United Kingdom.

(56) References Cited

OTHER PUBLICATIONS

Dua et al., A Tutorial on Target-Mediated Drug Disposition (TMDD) Models. CPT Pharmacometrics Syst Pharmacol. Jun. 2015;4(6):324-37. doi: 10.1002/psp4.41. Epub Jun. 15, 2015. Supporting Information, 11 pages.

Dumet et al., Insights into the IgG heavy chain engineering patent landscape as applied to IgG4 antibody development. MAbs. Nov.-Dec. 2019;11(8):1341-1350. doi: 10.1080/19420862.2019.1664365. Epub Sep. 26, 2019.

Fitzpatrick et al., An open label clinical trial of complement inhibition in multifocal motor neuropathy. J Peripher Nerv Syst. Jun. 2011;16:84-91.

Foote et al., "Antibody framework residues affecting the conformation of the hypervariable loops," J. Mol. Biol. 224:487-499, Elsevier, Netherlands (1992) (Elsevier Pub., Cambridge, MA).

Frank et al., Cold agglutinins and cold-agglutinin disease. Annu Rev Med. 1977;28:291-8. doi: 10.1146/annurev.me.28.020177.001451.

Gal et al., "C1s, the Protease Messenger of C1. Structure, Function and Physiological Significance," Immunobiology 205(4-5):383-394, Amsterdam : Elsevier, Netherlands (Sep. 2002).

Gal et al., "Early Complement Proteases: C1r, C1s and MASPs. A Structural Insight into Activation and Functions," Molecular Immunology 46(14):2745-2752, Elsmford, N. Y., Pergamon Press, England (May 2009).

Hamad et al., "Complement Activation by PEGylated Single-Walled Carbon Nanotubes Is Independent of C1q and Alternative Pathway Turnover," Molecular Immunology 45(14):3797-3803, Elmsford, N. Y., Pergamon Press, England (Aug. 2008 ). Author manuscript.

Heinz et al., "Monoclonal Antibodies Against Components of the Classical Pathway of Complement," Complement and Inflammation 6(3):166-174, New York : Karger, Switzerland (1989).

Hinson et al., Prediction of Neuromyelitis Optica Attack Severity by Quantitation of Complement-Mediated Injury to Aquaporin-4-Expressing Cells. Arch Neurol. Sep. 2009;66(9):1164-7.

Ishikawa et al., Influence of pH on heat-induced aggregation and degradation of therapeutic monoclonal antibodies. Biol Pharm Bull. 2010;33(8):1413-7. doi: 10.1248/bpb.33.1413.

Iwata et al., Bullous pemphigoid: role of complement and mechanisms for blister formation within the lamina lucida. Exp Derm. May 7, 2013;22:381-5.

Jaeger et al., Therapeutic Rationale and Clinical Development of TNT009, an Upstream Classical Pathway Inhibitor, for Cold Agglutinin Disease. Blood. 2015;126:3560. Retrieved from the Internet: http://www.bloodjournal.org/content/126/23/3560. 7 pages.

Jilma et al., Chronic Inhibition of Complement C1s By TNT009 Produces Sustained, Complete Remission in Patients with Severe, Transfusion-Dependent Cold Agglutinin Disease (CAD). Blood. 2016;128:2435. Retrieved from the Internet: http://www.bloodjournal.org/content/128/22/2435 on Apr. 9, 2019. 8 pages.

Kaminski et al., Multiparameter flow cytometry and bioanalytics for B cell profiling in systemic lupus erythematosus. Methods Mol Biol. 2012;900:109-34. doi: 10.1007/978-1-60761-720-4_6.

Kidmose et al., " Structural Basis for Activation of the Complement System by Component C4 Cleavage," Proceedings of the National Academy of Sciences 109(38):15425-15430, Washington, DC : National Academy of Sciences, United States (Sep. 2012).

Klechevsky et al., Cross-priming CD8+ T cells by targeting antigens to human dendritic cells through DCIR. Blood. Sep. 9, 2010;116(10):1685-97. doi: 10.1182/blood-2010-01-264960. Epub Jun. 7, 2010.

Konstantinov et al., Detection of autoantibodies in a point-of-care rheumatology setting. Auto Immun Highlights. May 18, 2013;4(2):55-61. doi: 10.1007/s13317-013-0052-9.

Kusner et al., Effect of complement and its regulation on myasthenia gravis pathogenesis. Expert Rev Clin Immunol. Jan. 2008;4(1):43-52.

Kussie et al., "A Single Engineered Amino Acid Substitution Changes Antibody Fine Specificity," Journal of Immunology 152(1):146-152, American Association of Immunologists, United States (1994).

Matsumoto et al., "Acceleration of Site-To-Site Transfer of C1—by a Monoclonal Antibody to C1-s ," Molecular Immunology 26(8):697-703, Oxford, Elmsford, N. Y., Pergamon Press, England (Aug. 1989).

Matsumoto et al., "Functional Analysis of Activated C1s, a Subcomponent of the First Component of Human Complement, by Monoclonal Antibodies," Journal of Immunology 137(9):2907-2912, Baltimore : Williams & Wilkins, United States (Nov. 1986).

Matsumoto et al., "Probing the C4-Binding Site on C1s with Monoclonal Antibodies. Evidence for a C4/C4b-Binding Site on the Gamma-Domain," Journal of Immunology 142(8):2743-2750, Baltimore : Williams & Wilkins, United States (Apr. 1989).

Monnet et al., Selection of IgG Variants with Increased FcRn Binding Using Random and Directed Mutagenesis: Impact on Effector Functions. Front Immunol. Feb. 4, 2015;6:39. doi: 10.3389/fimmu.2015.00039.

Moore et al., Engineered Fc variant antibodies with enhanced ability to recruit complement and mediate effector functions. MAbs. Mar.-Apr. 2010;2(2):181-9.

Mould et al., The pharmacokinetics and pharmacodynamics of monoclonal antibodies—mechanistic modeling applied to drug development. Curr Opin Drug Discov Devel. Jan. 2007;10(1):84-96.

Mühlbacher et al., Blockade of HLA Antibody-Triggered Classical Complement Activation in Sera From Subjects Dosed With the Anti-C1s Monoclonal Antibody TNT009—Results from a Randomized First-in-Human Phase 1 Trial. Transplantation. Oct. 2017;101(10):2410-2418. doi: 10.1097/TP.0000000000001804.

Nagaki et al., "Specific Antisera to C1s: Detection of Different Electrophoretic Species of C1s," Journal of Immunology 103(1):141-145, Baltimore : Williams & Wilkins, United States (Jul. 1969).

Nakagawa et al., "Complement C1s Activation In Degenerating Articular Cartilage of Rheumatoid Arthritis Patients: Immunohistochemical Studies With an Active Form Specific Antibody," Annals of the Rheumatic Diseases 58(3):175-181, London : BMJ, England (Mar. 1999).

Nakagawa et al., "Coordinated Change Between Complement C1s Production and Chondrocyte Differentiation In Vitro," Cell and Tissue Research 289(2):299-305, Berlin, New York, Springer-Verlag, Germany (Aug. 1997).

Panicker et al., TNT009 Prevents Erythrocyte C3 Fragment Opsonization and Rescues Reticulocytes from Destruction in Patients with Cold Agglutinin Disease. Blood. 2016;128:94. Retrieved from the Internet: http://www.bloodjournal.org/content/128/22/94 on Apr. 9, 2019. 7 pages.

Phuan et al., "C1q-targeted Monoclonal Antibody Prevents Complement-Dependent Cytotoxicity and Neuropathology In in Vitro and Mouse Models of Neuromyelitis Optica," Acta Neuropathologica 125(6):829-840, Berlin : Springer Verlag, Germany (Jun. 2013). Author manuscript.

Piche-Nicholas et al., Changes in complementarity-determining regions significantly alter IgG binding to the neonatal Fc receptor (FcRn) and pharmacokinetics. MAbs. Jan. 2018;10(1):81-94. doi: 10.1080/19420862.2017.1389355. Epub Nov. 3, 2017.

Reddy et al., "Elimination of Fc Receptor-Dependent Effector Functions of a Modified IgG4 Monoclonal Antibody to Human CD4," Journal of Immunology 164(4):1925-1933, American Association of Immunologists, United States (2000).

Ricklin et al., Complement in Immune and Inflammatory Disorders: Pathophysiological Mechanisms. Apr. 15, 2013;190(8):3831-8.

Rossi et al., "Baculovirmediated Expression of Truncated Modular Fragments from the Catalytic Region of Human Complement Serine Protease C1s. Evidence for the Involvement of Both Complement Control Protein Modules In the Recognition of the C4 Protein Substrate," Journal of Biological Chemistry 273(2):1232-1239, Baltimore, MD : American Society for Biochemistry and Molecular Biology, United States (Jan. 1998).

Röth et al., Inhibition of complement C1s with sutimlimab in patients with cold agglutinin disease (CAD): results from the phase 3 cardinal study. Blood. Nov. 21, 2019;134:LBA-2.

Röth et al., Sutimlimab in Cold Agglutinin Disease. N Engl J Med. Apr. 8, 2021;384(14):1323-1334. doi: 10.1056/NEJMoa2027760.

Rudikoff et al., "Single Amino Acid Substitution Altering Antigen-binding Specificity," Proceedings of the National Academy of

(56) References Cited

OTHER PUBLICATIONS

Sciences of the United States of America 79(6): 1979-1983, National Academy of Sciences, Washington (Mar. 1982).

Sakiyama et al., "Biochemical Characterization and Tissue Distribution of Hamster Complement C1s," Journal of Immunology. 146(1):183-187, Bethesda, MD : American Association of Immunologists, United States (Jan. 1991).

Sakiyama et al., "Complement C1s, a Classical Enzyme with Novel Functions at the Endochondral Ossification Center: Immunohistochemical Staining of Activated Cls with a Neoantigen-Specific Antibody," Cell and Tissue Research 288(3):557-565, Berlin, New York, Springer-Verlag, Germany (Jun. 1997).

Sakiyama et al., "Site-Directed Mutagenesis of Hamster Complement C1S: Characterization with an Active Form-Specific Antibody and Possible Involvement of CIS in Tumorigenicity," International Journal of Cancer 66(6):768-771, New York, NY : Wiley-Liss, United States (Jun. 1996).

Sethi et al., Membranoproliferative Glomerulonephritis and C3 Glomerulopathy: Resolving the Confusion. Kidney Int. Mar. 2012;81(5):434-441.

Shi et al., TNT003, an inhibitor of the serine protease C1s, prevents complement activation induced by cold agglutinins. Blood. Jun. 26, 2014;123(26):4015-22. doi: 10.1182/blood-2014-02-556027. Epub Apr. 2, 2014.

Silva et al., The S228P mutation prevents in vivo and in vitro IgG4 Fab-arm exchange as demonstrated using a combination of novel quantitative immunoassays and physiological matrix preparation. J Biol Chem. Feb. 27, 2015;290(9):5462-9. doi: 10.1074/jbc.M114.600973. Epub Jan. 7, 2015.

Strobel et al., Hemolytic Transfusion Reactions. Transfus Med Hemother. Sep. 18, 2008;35:346-353.

Susuki et al., Anti-GM1 antibodies cause complement-mediated disruption of sodium channel clusters in peripheral motor nerve fibers. J Neurosci. Apr. 11, 2007;27(15):3956-67.

Thielens et al., "Comparative Study of the Fluid-Phase Proteolytic Cleavage of Human Complement Subcomponents C4 and C2 by C1s and C1r2-C1s2," FEBS Letters 165(1):111-116, West Sussex : John Wiley & Sons Ltd, England (Jan. 1984).

Tichaczek-Goska, Deficiencies and Excessive Human Complement System Activation in Disorders of Multifarious Etiology. Adv Clin Exp Med. Jan.-Feb. 2012;21(1):105-14.

Tseng et al., "Probing the Structure of C1 with an Anti-C1s Monoclonal Antibody: The Possible Existence of Two Forms of C1 in Solution," Molecular Immunology 34(8-9):671-679, Oxford, Elmsford, N. Y., Pergamon Press, England (Jun. 1997).

Veerhuis et al., "Early Complement Components in Alzheimer's Disease Brains," Acta Neuropathologica 91(1):53-60, Berlin : Springer Verlag, Germany (1996).

Wahrmann et al., Effect of the Anti-C1s Humanized Antibody TNT009 and Its Parental Mouse Variant TNT003 on HLA Antibody-Induced Complement Activation—A Preclinical In Vitro Study. Am J Transplant. Sep. 2017;17(9):2300-2311. doi: 10.1111/ajt.14256. Epub Mar. 31, 2017.

Walpole et al., The weight of nations: an estimation of adult human biomass. BMC Public Health. Jun. 18, 2012;12:439. doi: 10.1186/1471-2458-12-439.

Weitz et al., Inflammation and fatigue in patients with cold agglutinin disease (CAD): analysis from the phase 3 Cardinal study. Blood. Nov. 5, 2020;136:7-8.

Williams et al., Humanising antibodies by CDR grafting. Antibody Engineering. 2010;1:319-39.

Wines et al., "The IgG Fe Contains Distinct Fe Receptor (FcR) Binding Sites: The Leukocyte Receptors Fc Gamma RI and Fc Gamma RIIa Bind to a Region in the Fc Distinct from that Recognized by Neonatal FcR and Protein A," Journal of Immunology 164(10):5313-5318, Bethesda, MD : American Association of Immunologists, United States (May 2000).

Zalevsky et al., Enhanced antibody half-life improves in vivo activity. Nat Biotechnol. Feb. 2010;28(2):157-9. doi: 10.1038/nbt.1601. Epub Jan. 17, 2010.

Benhnia et al., Heavily isotype-dependent protective activities of human antibodies against vaccinia virus extracellular virion antigen B5. J Virol. Dec. 2009;83(23):12355-67. doi: 10.1128/JVI.01593-09. Epub Sep. 30, 2009.

Berentsen et al., New Insights in the Pathogenesis and Therapy of Cold Agglutinin-Mediated Autoimmune Hemolytic Anemia. Front Immunol. Apr. 7, 2020;11:590. doi: 10.3389/fimmu.2020.00590.

Dall'Acqua et al., Properties of human IgG1s engineered for enhanced binding to the neonatal Fc receptor (FcRn). J Biol Chem. Aug. 18, 2006;281(33):23514-24. doi: 10.1074/jbc.M604292200. Epub Jun. 21, 2006.

Daugherty et al., Polymerase chain reaction facilitates the cloning, CDR-grafting, and rapid expression of a murine monoclonal antibody directed against the CD18 component of leukocyte integrins. Nucleic Acids Res. May 11, 1991;19(9):2471-6. doi: 10.1093/nar/19.9.2471.

Doneddu et al., Atypical chronic inflammatory demyelinating polyradiculoneuropathy: recent advances on classification, diagnosis, and pathogenesis. Curr Opin Neurol. Oct. 1, 2021;34(5):613-624. doi: 10.1097/WCO.0000000000000979.

Drachenberg et al., Guidelines for the diagnosis of antibody-mediated rejection in pancreas allografts-updated Banff grading schema. Am J Transplant. Sep. 2011;11(9):1792-802. doi: 10.1111/j.1600-6143.2011.03670.x. Epub Aug. 3, 2011.

Extended European Search Report mailed Nov. 14, 2025 for European Application No. 25188610.7.

Holliger et al., "Diabodies": small bivalent and bispecific antibody fragments. Proc Natl Acad Sci U S A. Jul. 15, 1993;90(14):6444-8. doi: 10.1073/pnas.90.14.6444.

Jäger et al., Inhibition of complement C1s improves severe hemolytic anemia in cold agglutinin disease: a first-in-human trial. Blood. Feb. 28, 2019;133(9):893-901. doi: 10.1182/blood-2018-06-856930. Epub Dec. 17, 2018.

Kabat et al., Unusual distributions of amino acids in complementarity-determining (hypervariable) segments of heavy and light chains of immunoglobulins and their possible roles in specificity of antibody-combining sites. J Biol Chem. Oct. 10, 1977;252(19):6609-16.

Kammann et al., Rapid insertional mutagenesis of DNA by polymerase chain reaction (PCR). Nucleic Acids Res. Jul. 11, 1989;17(13):5404. doi: 10.1093/nar/17.13.5404.

Lewis et al., Placebo effect in chronic inflammatory demyelinating polyneuropathy: The PATH study and a systematic review. J Peripher Nerv Syst. Sep. 2020;25(3):230-237. doi: 10.1111/jns.12402. Epub Aug. 5, 2020.

Sandhu, J. Protein engineering of antibodies. Crit Rev Biotechnol. 1992;12(5-6):437-62. doi: 10.3109/07388559209114235.

Sato et al., Reshaping a human antibody to inhibit the interleukin 6-dependent tumor cell growth. Cancer Res. Feb. 15, 1993;53(4):851-6.

Shields et al., High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-604. doi: 10.1074/jbc.M009483200. Epub Nov. 28, 2000.

Smith et al., Mouse model recapitulating human Fcγ receptor structural and functional diversity. Proc Natl Acad Sci U S A. Apr. 17, 2012;109(16):6181-6. doi: 10.1073/pnas.1203954109. Epub Apr. 2, 2012.

Ulvestad et al., Acute phase haemolysis in chronic cold agglutinin disease. Scand J Immunol. Jul.-Aug. 2001;54(1-2):239-42. doi: 10.1046/j.1365-3083.2001.00960.x.

Van Den Bergh et al. European Academy of Neurology/Peripheral Nerve Society guideline on diagnosis and treatment of chronic inflammatory demyelinating polyradiculoneuropathy: Report of a joint Task Force-Second revision. Eur J Neurol. Nov. 2021;28(11):3556-3583. doi: 10.1111/ene.14959. Epub Jul. 30, 2021. Erratum in: Eur J Neurol. Apr. 2022;29(4):1288. doi: 10.1111/ene.15225.

Van Den Bergh et al., European Academy of Neurology/Peripheral Nerve Society guideline on diagnosis and treatment of chronic inflammatory demyelinating polyradiculoneuropathy: Report of a joint Task Force-Second revision. J Peripher Nerv Syst. Sep. 2021;26(3):242-268. doi: 10.1111/jns.12455. Epub Jul. 30, 2021.

(56) References Cited

OTHER PUBLICATIONS

Erratum in: J Peripher Nerv Syst. Mar. 2022;27(1):94. doi: 10.1111/jns.12479. Erratum in: Eur J Neurol. Apr. 2022;29(4):1288. doi: 10.1111/ene.15225.

Van Den Bergh et al., European Federation of Neurological Societies/Peripheral Nerve Society Guideline on management of chronic inflammatory demyelinating polyradiculoneuropathy: Report of a joint task force of the European Federation of Neurological Societies and the Peripheral Nerve Society—First Revision. European J of Neurology. 2010;17:356-363. doi:10.1111/j.1468-1331.2009.02930.x.

Wagner et al., Therapeutic potential of complement modulation. Nat Rev Drug Discov. Jan. 2010;9(1):43-56. doi: 10.1038/nrd3011. Epub Dec. 4, 2009.

* cited by examiner

METHODS FOR TREATING COMPLEMENT-MEDIATED DISEASES

RELATED APPLICATIONS

This application claims the benefit under 35 U.S.C. § 119(e) of U.S. provisional application Ser. No. 63/355,296, filed Jun. 24, 2022; U.S. provisional application Ser. No. 63/370,484, filed Aug. 4, 2022; U.S. provisional application Ser. No. 63/375,041, filed Sep. 8, 2022; and U.S. provisional application Ser. No. 63/379,626, filed Oct. 14, 2022; the entire contents of each of which is incorporated herein by reference.

REFERENCE TO AN ELECTRONIC SEQUENCE LISTING

The contents of the electronic sequence listing (File Name: B155370018WO00-SEQ-JRV.xml; Size: 21,392 bytes; and Date of Creation: Jun. 19, 2023) is herein incorporated by reference in its entirety.

BACKGROUND

The complement system is a well-known effector mechanism of the immune response, providing not only protection against pathogens and other harmful agents but also recovery from injury. The classical complement pathway is triggered by activation of the first component of complement, referred to as the C1 complex, which includes C1q, C1r, and C1s proteins. Upon binding of C1 to an immune complex, the C1s component, a di-isopropyl fluorophosphate (DFP)-sensitive serine protease, cleaves complement components C4 and C2 to initiate activation of the classical complement pathway. The classical complement pathway appears to play a role in many diseases and disorders and there is a need for safe and effective therapeutics targeting this pathway.

SUMMARY

The present disclosure provides methods of treating classical complement-mediated disorders such as cold agglutinin disease (CAD) and chronic inflammatory demyelinating polyneuropathy (CIDP) using a humanized antibody that specifically binds complement C1s protein (i.e., a humanized anti-complement C1s antibody, also referred to herein as a "humanized anti-C1s antibody," a "humanized C1s antibody," or a "subject antibody").

Therapeutic options are limited for classical complement-mediated disorders, such as CAD and CIDP. The subject antibody, a humanized monoclonal antibody directed against activated C1s, can provide clinical benefit to patients with diseases of the classical complement system by specifically targeting the activated classical pathway. The studies described herein assess the safety, tolerability, and pharmacokinetic and pharmacodynamic profiles of the subject antibody in healthy participants as well as in CAD and CIDP patients. It is demonstrated herein that the subject antibody was generally well tolerated. The subject antibody demonstrated acceptable bioavailability after SC administration, and a long elimination half-life with linear kinetics. The subject antibody further inhibited the classical complement pathway (CP) and 50% hemolytic complement activity (CH50) activity to levels consistent with complement-deficient states in a dose-dependent manner. Preliminary results in CIDP patients further indicate that treatment with the subject antibody is able to improve functional disability, as measured by the INCAT score, in patients with CIDP who are refractory to other CIDP treatments and in patients with CIDP who are being treated with standard of care treatments. The results support further evaluation of the subject antibody in diseases characterized by dysfunctional or uncontrolled activation of the classical pathway of complement such as CAD and CIDP.

In one aspect, the present disclosure provides a method for treating cold-agglutinin disease in a subject in need thereof, comprising administering to the subject about 3.5 g of a humanized antibody that specifically binds complement component C1s, wherein the antibody comprises a light chain (LC) complementarity determining region (CDR) 1 comprising the amino acid sequence of SEQ ID NO: 1, a LC CDR2 comprising the amino acid sequence of SEQ ID NO: 2, a LC CDR3 comprising the amino acid sequence of SEQ ID NO: 3 and a heavy chain (HC) CDR1 comprising the amino acid sequence of SEQ ID NO: 4, an HC CDR2 comprising the amino acid sequence of SEQ ID NO: 5, and an HC CDR3 comprising the amino acid sequence of SEQ ID NO: 6.

In some embodiments, the antibody is administered about every 10, 12, 14, or 16 weeks. In some embodiments, the antibody is administered about every 12 weeks.

In some embodiments, about 3.5 g of the antibody is administered about 4 weeks after the first dose.

In some embodiments the antibody is administered intravenously or subcutaneously. In some embodiments, the antibody is administered intravenously.

In some embodiments, about 3.5 g of the antibody is administered intravenously on Day 1 and about every 10, 12, 14, or 16 weeks thereafter, and about 3.5 g of the antibody is additionally administered intravenously on or about Day 29. In some embodiments, 3.5 g of the antibody is administered intravenously on Day 1 and about every 10, 12, 14, or 16 weeks thereafter, and 3.5 g of the antibody is additionally administered intravenously on Day 29.

In some embodiments, about 3.5 g of the antibody is administered intravenously on Day 1 and about every 12 weeks thereafter, and about 3.5 g of the antibody is additionally administered intravenously on or about Day 29. In some embodiments, 3.5 g of the antibody is administered intravenously on Day 1 and about every 12 weeks thereafter, and 3.5 g of the antibody is additionally administered intravenously on Day 29.

In some embodiments, administration of the antibody increases the level of hemoglobin in the subject. In some embodiments, administration of the antibody decreases the level of bilirubin in the subject. In some embodiments, administration of the antibody inhibits the classical complement pathway activity by about 90% or greater. In some embodiments, classical complement pathway activity is determined by measuring the amount of the terminal complement complex, C5b-9. In some embodiments, administration of the antibody decreases the 50% hemolytic complement activity (CH50) level to less than about 10 IU/mL. In some embodiments, following administration of the antibody, the subject has a plasma concentration of the antibody of at least about 100 μg/mL.

In one aspect, the present disclosure provides a method for treating chronic inflammatory demyelinating polyneuropathy (CIDP) in a subject in need thereof, comprising administering to the subject a loading dose of about 50 mg/kg of the subject's body weight of a humanized antibody that specifically binds complement component C1s, and one or more maintenance doses of about 300 mg of the antibody, wherein the antibody comprises a light chain (LC) complementarity determining region (CDR) 1 comprising the amino acid sequence of SEQ ID NO: 1, a LC CDR2 comprising the amino acid sequence of SEQ ID NO: 2, a LC CDR3 comprising the amino acid sequence of SEQ ID NO: 3 and a heavy chain (HC) CDR1 comprising the amino acid sequence of SEQ ID NO: 4, an HC CDR2 comprising the amino acid sequence of SEQ ID NO: 5, and an HC CDR3 comprising the amino acid sequence of SEQ ID NO: 6.

In one aspect, the present disclosure provides a method for treating chronic inflammatory demyelinating polyneuropathy (CIDP) in a subject in need thereof, comprising administering to the subject a loading dose of about 50 mg/kg of the subject's body weight of a humanized antibody that specifically binds complement component C1s, and one or more maintenance doses of about 600 mg of the antibody, wherein the antibody comprises a light chain (LC) complementarity determining region (CDR) 1 comprising the amino acid sequence of SEQ ID NO: 1, a LC CDR2 comprising the amino acid sequence of SEQ ID NO: 2, a LC CDR3 comprising the amino acid sequence of SEQ ID NO: 3 and a heavy chain (HC) CDR1 comprising the amino acid sequence of SEQ ID NO: 4, an HC CDR2 comprising the amino acid sequence of SEQ ID NO: 5, and an HC CDR3 comprising the amino acid sequence of SEQ ID NO: 6.

In one aspect, the present disclosure provides a method for treating chronic inflammatory demyelinating polyneuropathy (CIDP) in a subject in need thereof, comprising administering to the subject a loading dose of about 50 mg/kg of the subject's body weight of a humanized antibody that specifically binds complement component C1s, and one or more maintenance doses of about 1200 mg of the antibody, wherein the antibody comprises a light chain (LC) complementarity determining region (CDR) 1 comprising the amino acid sequence of SEQ ID NO: 1, a LC CDR2 comprising the amino acid sequence of SEQ ID NO: 2, a LC CDR3 comprising the amino acid sequence of SEQ ID NO: 3 and a heavy chain (HC) CDR1 comprising the amino acid sequence of SEQ ID NO: 4, an HC CDR2 comprising the amino acid sequence of SEQ ID NO: 5, and an HC CDR3 comprising the amino acid sequence of SEQ ID NO: 6.

In one aspect, the present disclosure provides a method for treating chronic inflammatory demyelinating polyneuropathy (CIDP) in a subject in need thereof, comprising administering to the subject a loading dose of about 50 mg/kg of the subject's body weight of a humanized antibody that specifically binds complement component C1s, and one or more maintenance doses of about 2400 mg of the antibody, wherein the antibody comprises a light chain (LC) complementarity determining region (CDR) 1 comprising the amino acid sequence of SEQ ID NO: 1, a LC CDR2 comprising the amino acid sequence of SEQ ID NO: 2, a LC CDR3 comprising the amino acid sequence of SEQ ID NO: 3 and a heavy chain (HC) CDR1 comprising the amino acid sequence of SEQ ID NO: 4, an HC CDR2 comprising the amino acid sequence of SEQ ID NO: 5, and an HC CDR3 comprising the amino acid sequence of SEQ ID NO: 6.

In one aspect, the present disclosure provides a method for treating chronic inflammatory demyelinating polyneuropathy (CIDP) in a subject in need thereof, comprising administering to the subject a loading dose of about 50 mg/kg of the subject's body weight of a humanized antibody that specifically binds complement component C1s, and one or more maintenance doses of about 3600 mg of the antibody, wherein the antibody comprises a light chain (LC) complementarity determining region (CDR) 1 comprising the amino acid sequence of SEQ ID NO: 1, a LC CDR2 comprising the amino acid sequence of SEQ ID NO: 2, a LC CDR3 comprising the amino acid sequence of SEQ ID NO: 3 and a heavy chain (HC) CDR1 comprising the amino acid sequence of SEQ ID NO: 4, an HC CDR2 comprising the amino acid sequence of SEQ ID NO: 5, and an HC CDR3 comprising the amino acid sequence of SEQ ID NO: 6.

In one aspect, the present disclosure provides a method for treating chronic inflammatory demyelinating polyneuropathy (CIDP) in a subject in need thereof, comprising administering to the subject a loading dose of about 50 mg/kg of the subject's body weight of a humanized antibody that specifically binds complement component C1s, and one or more maintenance doses of about 7200 mg of the antibody, wherein the antibody comprises a light chain (LC) complementarity determining region (CDR) 1 comprising the amino acid sequence of SEQ ID NO: 1, a LC CDR2 comprising the amino acid sequence of SEQ ID NO: 2, a LC CDR3 comprising the amino acid sequence of SEQ ID NO: 3 and a heavy chain (HC) CDR1 comprising the amino acid sequence of SEQ ID NO: 4, an HC CDR2 comprising the amino acid sequence of SEQ ID NO: 5, and an HC CDR3 comprising the amino acid sequence of SEQ ID NO: 6.

In some embodiments, the one or more maintenance doses are administered about every week, every 2 weeks, every 4 weeks, or every 12 weeks.

In some embodiments, the antibody is administered intravenously or subcutaneously.

In some embodiments, the loading dose is administered intravenously. In some embodiments, the one or more maintenance doses are administered subcutaneously.

In some embodiments, the loading dose is administered intravenously on Day 1, followed by subcutaneous administration of the maintenance dose about every week starting on Day 8.

In some embodiments, the loading dose of about 50 mg/kg of the subject's body weight of the antibody is administered intravenously on Day 1, followed by subcutaneous administration of a maintenance dose of about 300 mg of the antibody about every week starting on Day 8. In some embodiments, the loading dose of 50 mg/kg of the subject's body weight of the antibody is administered intravenously on Day 1, followed by subcutaneous administration of a maintenance dose of 300 mg of the antibody every week starting on Day 8.

In some embodiments, the loading dose of about 50 mg/kg of the subject's body weight of the antibody is administered intravenously on Day 1, followed by subcutaneous administration of a maintenance dose of about 600 mg of the antibody about every week starting on Day 8. In some embodiments, the loading dose of 50 mg/kg of the subject's body weight of the antibody is administered intravenously on Day 1, followed by subcutaneous administration of a maintenance dose of 600 mg of the antibody every week starting on Day 8.

In some embodiments, the loading dose of about 50 mg/kg of the subject's body weight of the antibody is administered intravenously on Day 1, followed by subcutaneous administration of a maintenance dose of about 600 mg of the antibody about every 2 weeks starting on Day 8. In some embodiments, the loading dose of 50 mg/kg of the subject's body weight of the antibody is administered intravenously on Day 1, followed by subcutaneous administration of a maintenance dose of 600 mg of the antibody every 2 weeks starting on Day 8.

In some embodiments, the loading dose of about 50 mg/kg of the subject's body weight of the antibody is administered intravenously on Day 1, followed by subcutaneous administration of a maintenance dose of about 1200 mg of the antibody about every 2 weeks starting on Day 8. In some embodiments, the loading dose of 50 mg/kg of the subject's body weight of the antibody is administered intravenously on Day 1, followed by subcutaneous administration of a maintenance dose of 1200 mg of the antibody every 2 weeks starting on Day 8.

In some embodiments, the loading dose of about 50 mg/kg of the subject's body weight of the antibody is administered intravenously on Day 1, followed by subcutaneous administration of a maintenance dose of about 1200 mg of the antibody about every 4 weeks starting on Day 29. In some embodiments, the loading dose of 50 mg/kg of the subject's body weight of the antibody is administered intravenously on Day 1, followed by subcutaneous administration of a maintenance dose of 1200 mg of the antibody every 4 weeks starting on Day 29.

In some embodiments, the loading dose of about 50 mg/kg of the subject's body weight of the antibody is administered intravenously on Day 1, followed by subcutaneous administration of a maintenance dose of about 2400 mg of the antibody about every 4 weeks starting on Day 29. In some embodiments, the loading dose of 50 mg/kg of the subject's body weight of the antibody is administered intravenously on Day 1, followed by subcutaneous administration of a maintenance dose of 2400 mg of the antibody every 4 weeks starting on Day 29.

In some embodiments, the loading dose of about 50 mg/kg of the subject's body weight of the antibody is administered intravenously on Day 1, followed by subcutaneous administration of a maintenance dose of about 3600 mg of the antibody about every 12 weeks starting on Day 29. In some embodiments, the loading dose of 50 mg/kg of the subject's body weight of the antibody is administered intravenously on Day 1, followed by subcutaneous administration of a maintenance dose of 3600 mg of the antibody every 12 weeks starting on Day 29.

In some embodiments, the loading dose of about 50 mg/kg of the subject's body weight of the antibody is administered intravenously on Day 1, followed by subcutaneous administration of a maintenance dose of about 7200 mg of the antibody about every 12 weeks starting on Day 29. In some embodiments, the loading dose of 50 mg/kg of the subject's body weight of the antibody is administered intravenously on Day 1, followed by subcutaneous administration of a maintenance dose of 7200 mg of the antibody every 12 weeks starting on Day 29.

In some embodiments, a one-time 50 mg/kg intravenous loading dose is administered on Day 1 and subcutaneous (SC) doses are administered with a pre-filled syringe, or autoinjector, or large-volume drug delivery system. In some embodiments, the SC doses administered are 300 mg qw, 600 mg qw, 600 mg q2w, 1200 mg q2w, 1200 mg q4w, 2400 mg q4w, 3600 mg q12w, or 7200 mg q12w. In some embodiments, SC doses are administered with a pre-filled syringe, or autoinjector, or large-volume drug delivery system until end of treatment.

In some embodiments, the subject is refractory to another CIDP treatment. In some embodiments, the subject has received another CIDP treatment within about one week of the loading dose or is concomitantly receiving another CIDP treatment. In some embodiments, the subject has not received another treatment for CIDP within about 6 months prior to the loading dose. In some embodiments, the other CIDP treatment is intravenous immunoglobulin (IVIg), subcutaneous immunoglobulin (SCIg), or corticosteroids.

In some embodiments, administration of the antibody results in a one point or greater decrease in adjusted Inflammatory Neuropathy Cause and Treatment (INCAT) disability score relative to the INCAT score prior to treatment with the antibody.

In some embodiments, following administration of the antibody, the subject has a plasma concentration of the antibody of at least about 1200 μg/mL.

In some embodiments, the antibody is contained in a syringe or a vial.

In some embodiments, the antibody is administered using a syringe, a pre-filled syringe, or a large-volume drug delivery system.

In some embodiments, the antibody is administered using an autoinjector.

In some embodiments, the antibody is administered using a large-volume device for subcutaneous injection.

In some embodiments, the antibody comprises a light chain variable region (VL) comprising the amino acid sequence of SEQ ID NO: 7 and a heavy chain variable region (VH) comprising the amino acid sequence of SEQ ID NO: 8.

In some embodiments, the antibody is a Fab fragment, a F(ab')2 fragment, a scFv, or a Fv.

In some embodiments, the antibody comprises a heavy chain constant region of the isotype IgG4.

In some embodiments, the IgG4 constant region comprises a proline, a glutamic acid, a leucine, and a serine substitutions at amino acid residues 108, 115, 308, and 314, respectively, relative to the IgG4 constant region sequence of SEQ ID NO: 11.

In some embodiments, the IgG4 constant region comprises the sequence of SEQ ID NO: 13.

In some embodiments, the antibody comprises a light chain comprising the amino acid sequence of SEQ ID NO: 9 and a heavy chain comprising the amino acid sequence of SEQ ID NO: 10.

Each of International Publication Nos. WO 2014/066744, filed Oct. 25, 2013, entitled Anti-Complement C1s Antibodies and Uses Thereof, WO 2016/164358, filed Apr. 5, 2016, entitled Humanized Anti-C1s Antibodies and Methods of Use Thereof, and WO 2018/071676, filed Oct. 12, 2017, entitled Anti-C1s Antibodies and Methods of Use Thereof, is herein incorporated by reference in its entirety.

BRIEF DESCRIPTION OF THE DRAWINGS

FIG. 21A. Overall data across the three study groups. FIG. 21B. Detailed and expanded analysis in SOC-Treated group based on response.

DETAILED DESCRIPTION

Humanized Anti-C1s Antibodies

Figure 1:
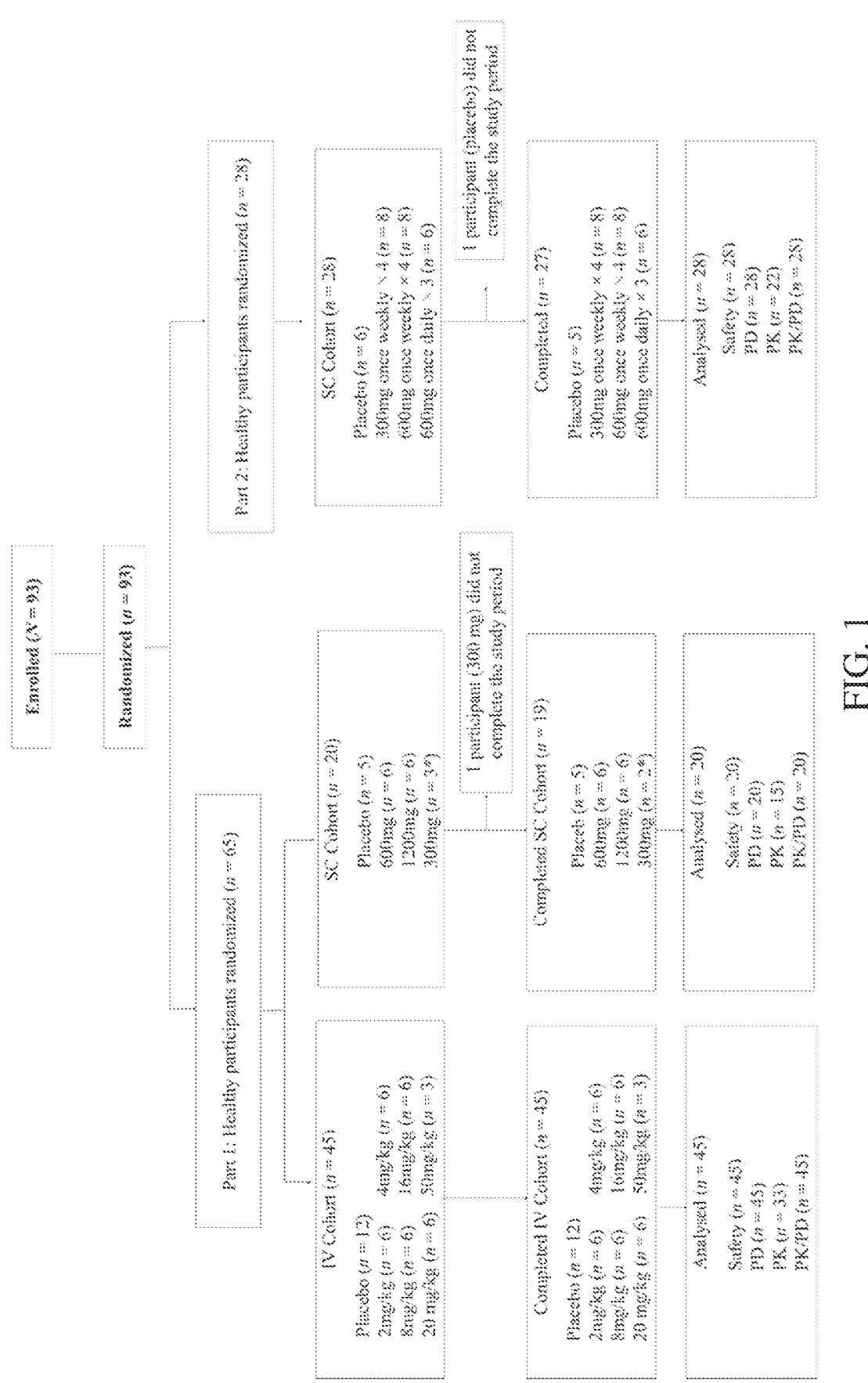
FIG. 1 shows a schematic of the participants' disposition. IV, intravenous; SC, subcutaneous; PD, pharmacodynamic; PK, pharmacokinetic; *Japanese.

The methods of the present disclosure comprise administering a humanized anti-C1s antibody. A humanized anti-C1s antibody of the disclosure binds to and inhibits the activated form of C1s within the classical pathway (CP). The complement system is a component of the innate immune system that mediates humoral immunity. The mechanism of the antibody is specific to the CP, leaving the lectin and the alternative pathways functionally intact.

In some embodiments, a humanized anti-C1s antibody of the present disclosure inhibits C1s-mediated cleavage of complement component C4, e.g., by inhibiting enzymatic activity of the serine-protease domain of C1s. In some embodiments, a humanized anti-C1s antibody of the present disclosure inhibits C1s-mediated cleavage of complement component C2. In some embodiments, a humanized anti-C1s antibody of the present disclosure inhibits C1s-mediated cleavage of C4 and C2.

In some embodiments, a humanized anti-C1s antibody of the present disclosure binds a complement C1s protein having the amino acid sequence depicted in SEQ ID NO: 15. Amino acid sequence SEQ ID NO: 15, provided below, represents the *Homo sapiens* complement C1s protein:

```
                                    (SEQ ID NO: 15)
EPTMYGEILSPNYPQAYPSEVEKSWDIEVPEGYGIHLYFT

HLDIELSENCAYDSVQIISGDTEEGRLCGQRSSNNPHSPI

VEEFQVPYNKLQVIFKSDFSNEERFTGFAAYYVATDINEC

TDFVDVPCSHFCNNFIGGYFCSCPPEYFLHDDMKNCGVNC

SGDVFTALIGEIASPNYPKPYPENSRCEYQIRLEKGFQVV

VTLRREDFDVEAADSAGNCLDSLVFVAGDRQFGPYCGHGF

PGPLNIETKSNALDIIFQTDLTGQKKGWKLRYHGDPMPCP

KEDTPNSVWEPAKAKYVFRDVVQITCLDGFEVVEGRVGAT

SFYSTCQSNGKWSNSKLKCQPVDCGIPESIENGKVEDPES

TLFGSVIRYTCEEPYYYMENGGGGEYHCAGNGSWVNEVLG

PELPKCVPVCGVPREPFEEKQRIIGGSDADIKNFPWQVFF

DNPWAGGALINEYWVLTAAHVVEGNREPTMYVGSTSVQTS

RLAKSKMLTPEHVFIHPGWKLLEVPEGRTNFDNDIALVRL

KDPVKMGPTVSPICLPGTSSDYNLMDGDLGLISGWGRTEK

RDRAVRLKAARLPVAPLRKCKEVKVEKPTADAEAYVFTPN
```

9

```
MICAGGEKGMDSCKGDSGGAFAVQDPNDKTKFYAAGLVSW

GPQCGTYGLYTRVKNYVDWIMKTMQENSTPRED.
```

In some embodiments, a humanized anti-C1s antibody of the present disclosure binds a human complement C1s protein with a dissociation constant (KD) of no more than 2.5 nM. In some embodiments, a humanized anti-C1s antibody of the present disclosure binds a human complement C1s protein with a KD of no more than 2 nM. In some embodiments, a humanized anti-C1s antibody of the present disclosure binds a human complement C1s protein with a KD of no more than 1 nM. In some embodiments, a humanized anti-C1s antibody of the present disclosure binds a human complement C1s protein with a KD of no more than 0.9 nM, no more than 0.8 nM, no more than 0.7 nM, no more than 0.6 nM, no more than 0.5 nM, no more than 0.4 nM, no more than 0.3 nM, no more than 0.2 nM, or no more than 0.1 nM. In some embodiments, a humanized anti-C1s antibody of the present disclosure binds a human complement C1s protein with a KD of no more than 0.3 nM. In some embodiments, a humanized anti-C1s antibody of the present disclosure binds a human complement C1s protein with a KD of no more than 0.2 nM. In some embodiments, a humanized anti-C1s antibody of the present disclosure binds a human complement C1s protein with a KD of no more than 0.1 nM. Methods to measure binding of an antibody to human complement C1s protein can be determined by one skilled in the art.

In some embodiments, a humanized anti-C1s antibody of the present disclosure binds a human complement C1s protein with a KD of no more than 90 pM, no more than 80 pM, no more than 70 pM, no more than 60 pM, no more than 50 pM, no more than 40 pM, no more than 30 pM, no more than 20 pM, no more than 10 pM, no more than 9 pM, no more than 8 pM, no more than 7 pM, no more than 6 pM, no more than 5 pM, no more than 4 pM, no more than 3 pM, no more than 2 pM, or no more than 1 pM.

In some embodiments, the humanized anti-C1s antibody of the present disclosure preferentially binds an active (or activated) human complement C1s protein, and does not substantially bind the inactive form of human complement C1s protein.

In some embodiments, a humanized anti-C1s antibody of the present disclosure inhibits the classical complement pathway with a half-maximal inhibitory concentration (IC50) of $10^{-8}$ M or less, $5\times10^{-9}$ M or less, or $10^{-9}$ M or less.

"Antibody" encompasses antibodies or immunoglobulins of any isotype, including but not limited to humanized antibodies and chimeric antibodies. An antibody may be a single-chain antibody (scAb) or a single domain antibody (dAb) (e.g., a single domain heavy chain antibody or a single domain light chain antibody; see Holt et al. (2003) Trends Biotechnol. 21:484). The term "antibody" also encompasses fragments of antibodies (antibody fragments) that retain specific binding to an antigen. "Antibody" further includes single-chain variable fragments (scFvs), which are fusion proteins of the variable regions of the heavy ($V_H$) and light chains ($V_L$) of antibodies, connected with a short linker peptide, and diabodies, which are noncovalent dimers of scFv fragments that include the $V_H$ and $V_L$ connected by a small peptide linker (Zapata et al., *Protein Eng.* 8(10): 1057-1062 (1995)). Other fusion proteins that comprise an antigen-binding portion of an antibody and a non-antibody protein are also encompassed by the term "antibody."

"Antibody fragments" comprise a portion of an intact antibody, for example, the antigen binding or variable region of the intact antibody. Examples of antibody fragments include an antigen-binding fragment (Fab), Fab', F(ab')$_2$, a variable domain Fv fragment (Fv), an Fd fragment, and an antigen binding fragment of a chimeric antigen receptor.

Papain digestion of antibodies produces two identical antigen-binding fragments, referred to as "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Fv" is the minimum antibody fragment that contains a complete antigen-recognition and -binding site. This region includes a dimer of one heavy-chain variable domain and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Fab" fragments contain the constant domain of the light chain and the first constant domain (CH$_1$) of the heavy chain. Fab fragments differ from Fab' fragments by the addition of a few residues at the carboxyl terminus of the heavy chain CH$_1$ domain including at least one cysteine from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"scFv" antibody fragments comprise the $V_H$ and $V_L$ of an antibody, wherein these regions are present in a single polypeptide chain. In some embodiments, the Fv polypeptide further comprises a polypeptide linker between the $V_H$ and $V_L$ regions, which enables the scFv to form the desired structure for antigen binding. For a review of scFv, see Pluckthun in *The Pharmacology of Monoclonal Antibodies*, vol. 113, Rosenburg and Moore eds., Springer-Verlag, New York, pp. 269-315 (1994).

"Diabody" refers to a small antibody fragment with two antigen-binding sites, which fragments comprise a $V_H$ connected to a $V_L$ in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, Hollinger et al. *Proc. Natl. Acad. Sci. USA* 90: 6444-6448 (1993).

An antibody can be monovalent or bivalent. An antibody can be an Ig monomer, which is a "Y-shaped" molecule that consists of four polypeptide chains: two heavy chains and two light chains connected by disulfide bonds.

Antibodies can be detectably labeled, e.g., with a radio-isotope, an enzyme that generates a detectable product, and/or a fluorescent protein. Antibodies can be further conjugated to other moieties, such as members of specific binding pairs, e.g., biotin member of biotin-avidin specific binding pair. Antibodies can also be bound to a solid support, including, but not limited to, polystyrene plates and/or beads.

An "isolated" antibody is one that has been identified and separated and/or recovered from a component of its natural environment (i.e., is not naturally occurring). Contaminant components of its natural environment are materials that would interfere with uses (e.g., diagnostic or therapeutic uses) of the antibody, and can include enzymes, hormones, and other proteinaceous or nonproteinaceous solutes. In some embodiments, an antibody is purified (1) to greater than 90%, greater than 95%, greater than 98% or greater than 99% by weight of antibody as determined by the Lowry method, for example, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or non-reducing conditions using Coomassie blue or silver stain. Isolated antibodies encompass antibodies in situ within recombinant cells, as at least one component of the antibody's natural environment will not be present. In some embodiments, an isolated antibody is prepared by at least one purification step.

A "monoclonal antibody" is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries).

A "complementarity determining region (CDR)" is the non-contiguous antigen combining sites found within the variable region of both heavy and light chain polypeptides. CDRs have been described by Lefranc et al. (2003) *Developmental and Comparative Immunology* 27:55; Kabat et al., J. Biol. Chem. 252:6609-6616 (1977); Kabat et al., U.S. Dept. of Health and Human Services, "Sequences of proteins of immunological interest" (1991); by Chothia et al., *J. Mol. Biol.* 196:901-917 (1987); and MacCallum et al., *J. Mol. Biol.* 262:732-745 (1996), where the definitions include overlapping or subsets of amino acid residues when compared against each other. Nevertheless, application of any of the Kabat, Lefranc, Chothia, or MacCallum definitions (also referred to as numbering systems) to refer to a CDR of an antibody or grafted antibodies or variants thereof is intended to be within the scope of the term as defined and used herein.

The terms "LC CDR1," "LC CDR2," and "LC CDR3" refer, respectively, to the first, second, and third CDRs in a light chain variable region. As used herein, the terms "HC CDR1," "HC CDR2," and "HC CDR3" refer, respectively, to the first, second, and third CDRs in a heavy chain variable region. As used herein, the terms "CDR1," "CDR2," and "CDR3" refer, respectively, to the first, second and third CDRs of either chain's variable region.

A "framework" when used in reference to an antibody variable region includes all amino acid residues outside the CDR regions within the variable region of an antibody. A variable region framework is generally a discontinuous amino acid sequence that includes only those amino acids outside of the CDRs. A "framework region" includes each domain of the framework that is separated by the CDRs.

A "humanized antibody" is an antibody comprising portions of antibodies of different origin, wherein at least one portion comprises amino acid sequences of human origin. For example, the humanized antibody can comprise portions derived from an antibody of nonhuman origin with the requisite specificity, such as a mouse, and from antibody sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized antibody is an antibody containing at least one chain comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120, 694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946, 778; Huston, U.S. Pat. No. 5,476,786; and Bird, R. E. et al., Science, 242: 423-426 (1988)), regarding single chain antibodies.

In some embodiments, a humanized antibody is produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

In some embodiments, a humanized anti-C1s antibody described herein is a full-length IgG, an Ig monomer, a Fab fragment, a F(ab')2 fragment, a Fd fragment, a scFv, a scAb, or a Fv. In some embodiments, a humanized anti-C1s antibody described herein is a full-length IgG. In some embodiments, the heavy chain of any of the humanized anti-C1s antibodies as described herein comprises a heavy chain constant region (CH) or a portion thereof (e.g., CH1, CH2, CH3, or a combination thereof). The heavy chain constant region can be of any suitable origin, e.g., human, mouse, rat, or rabbit. In some embodiments, the heavy chain constant region is from a human IgG (a gamma heavy chain), e.g., IgG1, IgG2, or IgG4.

In some embodiments, mutations can be introduced into the heavy chain constant region of any one of the humanized anti-C1s antibodies described herein. In some embodiments, one, two or more mutations (e.g., amino acid substitutions) are introduced into the heavy chain constant region (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, one, two or more mutations (e.g., amino acid substitutions) are introduced into the hinge region of the heavy chain constant region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more amino acid mutations (i.e., substitutions, insertions or deletions) are introduced into an IgG constant domain, or FcRn-binding fragment thereof to alter (e.g., decrease or increase) half-life of the antibody in vivo. In some embodiments, the one or more mutations are introduced into an Fc or hinge-Fc domain fragment. See, e.g., International Publication Nos. WO 02/060919; WO 98/23289; and WO 97/34631; and U.S. Pat. Nos. 5,869,046; 6,121,022; 6,277,375; and 6,165,745 for examples of mutations that will alter (e.g., decrease or increase) the half-life of an antibody in vivo.

In some embodiments, the constant region antibody described herein is an IgG1 constant region and comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat. Additional mutations that may be introduced to the heavy chain constant region that would increase the half-life of the antibody are known in the art, e.g., the M428L/N434S (EU numbering; M459L/N466S Kabat numbering) mutations as described in Zalevsky et al., Nat Biotechnol. 2010 February; 28(2): 157-159.

In some embodiments, one, two or more amino acid substitutions are introduced into an IgG constant domain Fc region to alter the effector function(s) of the antibody. The effector ligand to which affinity is altered can be, for example, an Fc receptor or the C1 component of complement. This approach is described in further detail in U.S. Pat. Nos. 5,624,821, and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591, 886 for a description of mutations that delete or inactivate the constant domain and thereby increase tumor localization. In some embodiments, at least one amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, at least one amino acid in the constant region can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.). In some embodiments, at least one amino acid residue in the N-terminal region of the CH2 domain of an antibody described herein is altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or to increase the affinity of the antibody for an Fcγ receptor. This approach is described further in International Publication No. WO 00/42072.

In some embodiments, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. In some embodiments, to reduce residual antibody-dependent cellular cytotoxicity, a L235E (EU numbering, corresponding to L248E in Kabat numbering) mutation is introduced to the heavy chain constant region, e.g., as described in Benhnia et al., J. Virology, December 2009, p. 12355-12367.

In some embodiments, a humanized anti-C1s antibody comprises a light chain complementarity determining region 1 (LC CDR1) comprising the amino acid sequence of KASQSVDYDGDSYMN (SEQ ID NO: 1). In some embodiments, a humanized anti-C1s antibody comprises a light chain complementarity determining region 2 (LC CDR2) comprising the amino acid sequence of DASNLES (SEQ ID NO: 2). In some embodiments, a humanized anti-C1s antibody comprises a light chain complementarity determining region 3 (LC CDR3) comprising the amino acid sequence of QQSNEDPWT (SEQ ID NO: 3). In some embodiments, a humanized anti-C1s antibody comprises an LC CDR1 comprising the amino acid sequence of SEQ ID NO: 1, an LC CDR2 comprising the amino acid sequence of SEQ ID NO: 2, and an LC CDR3 comprising the amino acid sequence of SEQ ID NO: 3.

In some embodiments, a humanized anti-C1s antibody comprises a heavy chain complementarity determining region 1 (HC CDR1) comprising the amino acid sequence of DDYIH (SEQ ID NO: 4). In some embodiments, a humanized anti-C1s antibody comprises a heavy chain complementarity determining region 2 (HC CDR2) comprising the amino acid sequence of RIDPADGHTKYAPKFQV (SEQ ID NO: 5). In some embodiments, a humanized anti-C1s antibody comprises a heavy chain complementarity determining region 3 (HC CDR3) comprising the amino acid sequence of YGYGREVFDY (SEQ ID NO: 6). In some embodiments, a humanized anti-C1s antibody comprises an HC CDR1 comprising the amino acid sequence of SEQ ID NO: 4, an HC CDR2 comprising the amino acid sequence of SEQ ID NO: 5, and an HC CDR3 comprising the amino acid sequence of SEQ ID NO: 6.

In some embodiments, a humanized anti-C1s antibody comprises an LC CDR1 that comprises the amino acid sequence of SEQ ID NO: 1, an LC CDR2 comprising the amino acid sequence of SEQ ID NO: 2, and an LC CDR3 comprising the amino acid sequence of SEQ ID NO: 3, an HC CDR1 comprising the amino acid sequence of SEQ ID NO: 4, an HC CDR2 comprising the amino acid sequence of SEQ ID NO: 5, an HC CDR3 comprising the amino acid sequence of SEQ ID NO: 6.

In some embodiments, a humanized anti-C1s antibody comprises a light chain variable region (VL) comprising the amino acid sequence of

```
                                    (SEQ ID NO: 7)
DIVLTQSPDSLAVSLGERATISCKASQSVDYDGDSYMNWY

QQKPGQPPKILIYDASNLESGIPARFSGSGSGTDFTLTIS

SLEPEDFAIYYCQQSNEDPWTFGGGTKVEIK.
```

In some embodiments, a humanized anti-C1s antibody comprises a LC CDR1, LC CDR2, and LC CDR3 of a VL comprising the amino acid sequence of SEQ ID NO: 7.

In some embodiments, a humanized anti-C1s antibody comprises a heavy chain variable region (VH) comprising the amino acid sequence of

```
                                    (SEQ ID NO: 8)
QVQLVQSGAEVKKPGASVKLSCTASGFNIKDDYIHWVKQA

PGQGLEWIGRIDPADGHTKYAPKFQVKVTITADTSTSTAY

LELSSLRSEDTAVYYCARYGYGREVEDYWGQGTTVTVSS.
```

HC CDR1, HC CDR2, and HC CDR3 of a VH comprising the amino acid sequence of SEQ ID NO: 8.

In some embodiments, a humanized anti-C1s antibody comprises a VL comprising the amino acid sequence of SEQ ID NO: 7 and a VH comprising the amino acid sequence of SEQ ID NO: 8.

In some embodiments, a humanized anti-C1s antibody comprises a LC CDR1, LC CDR2, and LC CDR3 of a VL comprising the amino acid sequence of SEQ ID NO: 7 and HC CDR1, HC CDR2, and HC CDR3 of a VH comprising the amino acid sequence of SEQ ID NO: 8.

In some embodiments, a humanized anti-C1s antibody comprises a light chain (LC) comprising the amino acid sequence of

```
                                    (SEQ ID NO: 9)
DIVLTQSPDSLAVSLGERATISCKASQSVDYDGDSYMNWY

QQKPGQPPKILIYDASNLESGIPARFSGSGSGTDFTLTIS

SLEPEDFAIYYCQQSNEDPWTFGGGTKVEIKRTVAAPSVF

IFPPSDEQLKSGTASVVCLLNNFYPREAKVQWKVDNALQS

GNSQESVTEQDSKDSTYSLSSTLTLSKADYEKHKVYACEV

THQGLSSPVTKSFNRGEC.
```

In some embodiments, a humanized anti-C1s antibody comprises a heavy chain (HC) comprising the amino acid sequence of

```
                                    (SEQ ID NO: 10)
QVQLVQSGAEVKKPGASVKLSCTASGFNIKDDYIHWVKQA

PGQGLEWIGRIDPADGHTKYAPKFQVKVTITADTSTSTAY
```

```
                                    -continued
LELSSLRSEDTAVYYCARYGYGREVEDYWGQGTTVTVSSA

STKGPSVFPLAPCSRSTSESTAALGCLVKDYFPEPVTVSW

NSGALTSGVHTFPAVLQSSGLYSLSSVVTVPSSSLGTKTY

TCNVDHKPSNTKVDKRVESKYGPPCPPCPAPEFEGGPSVF

LFPPKPKDTLMISRTPEVTCVVVDVSQEDPEVQFNWYVDG

VEVHNAKTKPREEQFNSTYRVVSVLTVLHQDWLNGKEYKC

KVSNKGLPSSIEKTISKAKGQPREPQVYTLPPSQEEMTKN

QVSLTCLVKGFYPSDIAVEWESNGQPENNYKTTPPVLDSD

GSFFLYSRLTVDKSRWQEGNVFSCSVLHEALHSHYTQKSL

SLSLGK.
```

In some embodiments, a humanized anti-C1s antibody comprises a LC comprising the amino acid sequence of SEQ ID NO: 9 and a HC comprising the amino acid sequence of SEQ ID NO: 10.

In some embodiments, a humanized anti-C1s antibody comprises an LC CDR1 comprising an amino acid sequence containing no more than 3 amino acid variations (e.g., no more than 3, 2, or 1 amino acid variation(s)) relative to the LC CDR1 amino acid sequence of SEQ ID NO: 1. In some embodiments, a humanized anti-C1s antibody comprises an LC CDR2 comprising an amino acid sequence containing no more than 3 amino acid variations (e.g., no more than 3, 2, or 1 amino acid variation(s)) relative to the LC CDR2 amino acid sequence of SEQ ID NO: 2. In some embodiments, a humanized anti-C1s antibody comprises an LC CDR3 comprising an amino acid sequence containing no more than 3 amino acid variations (e.g., no more than 3, 2, or 1 amino acid variation(s)) relative to the LC CDR3 amino acid sequence of SEQ ID NO: 3.

In some embodiments, a humanized anti-C1s antibody comprises an HC CDR1 comprising an amino acid sequence containing no more than 3 amino acid variations (e.g., no more than 3, 2, or 1 amino acid variation(s)) relative to the HC CDR1 amino acid sequence of SEQ ID NO: 4. In some embodiments, a humanized anti-C1s antibody comprises an HC CDR2 comprising an amino acid sequence containing no more than 3 amino acid variations (e.g., no more than 3, 2, or 1 amino acid variation(s)) relative to the HC CDR2 amino acid sequence of SEQ ID NO: 5. In some embodiments, a humanized anti-C1s antibody comprises an HC CDR3 comprising an amino acid sequence containing no more than 3 amino acid variations (e.g., no more than 3, 2, or 1 amino acid variation(s)) relative to the HC CDR3 amino acid sequence of SEQ ID NO: 6.

In some embodiments, a humanized anti-C1s antibody comprises a VL comprising an amino acid sequence containing no more than 20 amino acid variations (e.g., no more than 19, 18, 17, 16, 15, 14, 13, 12, 11, 10, 9, 8, 7, 6, 5, 4, 3, 2, or 1 amino acid variation(s)) relative to the VL amino acid sequence of SEQ ID NO: 7.

In some embodiments, a humanized anti-C1s antibody comprises a VH comprising an amino acid sequence containing no more than 20 amino acid variations (e.g., no more than 20, 19, 18, 17, 16, 15, 14, 13, 12, 11, 10, 9, 8, 7, 6, 5, 4, 3, 2, or 1 amino acid variation(s)) relative to the VH amino acid sequence of SEQ ID NO: 8.

In some embodiments, a humanized anti-C1s antibody comprises a VL comprising an LC CDR1 comprising the amino acid sequence of SEQ ID NO: 1, an LC CDR2 comprising the amino acid sequence of SEQ ID NO: 2, an LC CDR3 comprising the amino acid sequence of SEQ ID NO: 3, and comprises framework regions that contain no more than 20 amino acid variations (e.g., no more than 20, 19, 18, 17, 16, 15, 14, 13, 12, 11, 10, 9, 8, 7, 6, 4, 3, 2, or 1 amino acid variation(s)) relative to the VL sequence of SEQ ID NO: 7.

In some embodiments, a humanized anti-C1s antibody comprises a VH comprising an HC CDR1 comprising the amino acid sequence of SEQ ID NO: 4, an HC CDR2 comprising the amino acid sequence of SEQ ID NO: 5, an HC CDR3 comprising the amino acid sequence of SEQ ID NO: 6, and comprises framework regions that contain no more than 20 amino acid variations (e.g., no more than 20, 19, 18, 17, 16, 15, 14, 13, 12, 11, 10, 9, 8, 7, 6, 4, 3, 2, or 1 amino acid variation(s)) relative to the VH sequence of SEQ ID NO: 8.

In some embodiments, a humanized anti-C1s antibody comprises (a) a VL comprising an LC CDR1 comprising the amino acid sequence of SEQ ID NO: 1, an LC CDR2 comprising the amino acid sequence of SEQ ID NO: 2, an LC CDR3 comprising the amino acid sequence of SEQ ID NO: 3, and comprises framework regions that contain no more than amino acid variations (e.g., no more than 20, 19, 18, 17, 16, 15, 14, 13, 12, 11, 10, 9, 8, 7, 6, 5, 4, 3, 2, or 1 amino acid variation(s)) relative to the VL sequence of SEQ ID NO: 7, and (b) a VH comprising an HC CDR1 comprising the amino acid sequence of SEQ ID NO: 4, an HC CDR2 comprising the amino acid sequence of SEQ ID NO: 5, an HC CDR3 comprising the amino acid sequence of SEQ ID NO: 6, and comprises framework regions that contain no more than 20 amino acid variations (e.g., no more than 20, 19, 18, 17, 16, 15, 14, 13, 12, 11, 9, 8, 7, 6, 5, 4, 3, 2, or 1 amino acid variation(s)) relative to the VH sequence of SEQ ID NO: 8.

In some embodiments, a humanized anti-C1s antibody comprises a VL comprising an amino acid sequence having at least 80% (e.g., 80%, 85%, 90%, 95%, 96%, 97%, 98%, or 99%) identity to the VL amino acid sequence of SEQ ID NO: 7.

In some embodiments, a humanized anti-C1s antibody comprises a VH comprising an amino acid sequence having at least 80% (e.g., 80%, 85%, 90%, 95%, 96%, 97%, 98%, or 99%) identity to the VH amino acid sequence of SEQ ID NO: 8.

In some embodiments, a humanized anti-C1s antibody comprises a VL comprising an LC CDR1 comprising the amino acid sequence of SEQ ID NO: 1, an LC CDR2 comprising the amino acid sequence of SEQ ID NO: 2, an LC CDR3 comprising the amino acid sequence of SEQ ID NO: 3 and comprises framework regions that have at least 80% (e.g., 80%, 85%, 90%, 95%, 96%, 97%, 98%, or 99%) identity to the framework regions of the VL sequence of SEQ ID NO: 7.

In some embodiments, a humanized anti-C1s antibody comprises a VH comprising an HC CDR1 comprising the amino acid sequence of SEQ ID NO: 4, an HC CDR2 comprising the amino acid sequence of SEQ ID NO: 5, an HC CDR3 comprising the amino acid sequence of SEQ ID NO: 6 and comprises framework regions that have at least 80% (e.g., 80%, 85%, 90%, 95%, 96%, 97%, 98%, or 99%) identity to the framework regions of the VH sequence of SEQ ID NO: 8.

In some embodiments, a humanized anti-C1s antibody comprises (a) a VL comprising an LC CDR1 comprising the amino acid sequence of SEQ ID NO: 1, an LC CDR2 comprising the amino acid sequence of SEQ ID NO: 2, an LC CDR3 comprising the amino acid sequence of SEQ ID NO: 3, and comprises framework regions that have at least 80% (e.g., 80%, 85%, 90%, 95%, 96%, 97%, 98%, or 99%) identity to the framework regions of the VL sequence of SEQ ID NO: 7, and (b) a VH comprising an HC CDR1 comprising the amino acid sequence of SEQ ID NO: 4, an HC CDR2 comprising the amino acid sequence of SEQ ID NO: 5, an HC CDR3 comprising the amino acid sequence of SEQ ID NO: 6, and comprises framework regions that have at least 80% (e.g., 80%, 85%, 90%, 95%, 96%, 97%, 98%, or 99%) identity to the framework regions of the VH sequence of SEQ ID NO: 8.

In some embodiments, the heavy chain constant region in any one of the humanized anti-C1s antibodies described herein is an IgG4 constant region, or a variant there of. Examples of IgG4 constant regions and variants are provided in Table 1.

TABLE 1

Examples of Heavy Chain Constant Regions

| Heavy Chain Constant Region | Amino Acid Sequence |
|---|---|
| IgG4 constant region WT | ASTKGPSVFPLAPCSRSTSESTAAL GCLVKDYFPEPVTVSWNSGALTSGV HTFPAVLQSSGLYSLSSVVTVPSSS LGTKTYTCNVDHKPSNTKVDKRVES KYGPPCPSCPAPEFLGGPSVFLFPP KPKDTLMISRTPEVTCVVVDVSQED PEVQFNWYVDGVEVHNAKTKPREEQ FNSTYRVVSVLTVLHQDWLNGKEYK CKVSNKGLPSSIEKTISKAKGQPRE PQVYTLPPSQEEMTKNQVSLTCLVK GFYPSDIAVEWESNGQPENNYKTTP PVLDSDGSFFLYSRLTVDKSRWQEG NVFSCSVMHEALHNHYTQKSLSLSL GK (SEQ ID NO: 11) |
| IgG4 constant region variant 1 | ASTKGPSVFPLAPCSRSTSESTAAL GCLVKDYFPEPVTVSWNSGALTSGV HTFPAVLQSSGLYSLSSVVTVPSSS LGTKTYTCNVDHKPSNTKVDKRVES KYGPPCPPCPAPEFEGGPSVELFPP KPKDTLMISRTPEVTCVVVDVSQED PEVQFNWYVDGVEVHNAKTKPREEQ FNSTYRVVSVLTVLHQDWLNGKEYK CKVSNKGLPSSIEKTISKAKGQPRE PQVYTLPPSQEEMTKNQVSLTCLVK GFYPSDIAVEWESNGQPENNYKTTP PVLDSDGSFFLYSRLTVDKSRWQEG NVFSCSVMHEALHNHYTQKSLSLSL GK (SEQ ID NO: 12) |
| IgG4 constant region variant 2 | ASTKGPSVFPLAPCSRSTSESTAAL GCLVKDYFPEPVTVSWNSGALTSGV HTFPAVLQSSGLYSLSSVVTVPSSS LGTKTYTCNVDHKPSNTKVDKRVES KYGPPCPPCPAPEFEGGPSVELFPP KPKDTLMISRTPEVTCVVVDVSQED PEVQFNWYVDGVEVHNAKTKPREEQ FNSTYRVVSVLTVLHQDWLNGKEYK CKVSNKGLPSSIEKTISKAKGQPRE PQVYTLPPSQEEMTKNQVSLTCLVK GFYPSDIAVEWESNGQPENNYKTTP PVLDSDGSFFLYSRLTVDKSRWQEG NVFSCSVLHEALHSHYTQKSLSLSL GK (SEQ ID NO: 13) |

In some embodiments, the light chain of any of the humanized anti-C1s antibodies described herein may further comprise a light chain constant region ($C_L$). In some examples, the $C_L$ is a kappa light chain. In other examples, the $C_L$ is a lambda light chain. In some embodiments, the $C_L$ is a kappa light chain, the sequence of which is provided below:

```
RTVAAPSVFIFPPSDEQLKSGTASVVCLLNNFYPREAKVQWKVDN

ALQSGNSQESVTEQDSKDSTYSLSSTLTLSKADYEKHKVYACEVT

HQGLSSPVTKSENRGEC
```

Other antibody heavy and light chain constant regions are well known in the art, e.g., those provided in the IMGT database (imgt.org) or at vbase2.org/vbstat.php, both of which are incorporated by reference herein.

Methods of Treating CAD

Cold agglutinin disease (CAD) is an autoimmune hemolytic anemia caused by IgM-induced classical complement pathway activation. The IgM autoantibodies in CAD are referred to as cold agglutinins (CAgs) given their inherent property of increased binding as a function of decreased temperature. The CAg thermal amplitude, which is the highest temperature at which the CAg can be detected to react with the red blood cell antigen approaches core body temperature in many patients. Symptoms of CAD are typically triggered by exposure to cold environmental temperatures (i.e., temperatures at or below core body temperature), viral infections, or inflammation. All patients with CAD have active disease with varying levels of chronic, ongoing hemolysis resulting in anemia.

The present disclosure provides methods of treating CAD in a subject. In one aspect, the methods comprise administering to the subject an anti-C1s antibody in a fixed (or flat) dose of about 3 g to about 5 g. In some embodiments, the methods comprise administering to the subject an anti-C1s antibody in a fixed dose of about 3.5 g. In some embodiments, the methods comprise administering to the subject an anti-C1s antibody in a fixed dose of about 3 g, about 3.5 g, about 4 g, about 4.5 g, or about 4.5 g.

In some embodiments, the antibody is administered about every 10, 12, 14, or 16 weeks. In some embodiments, the anti-C1s antibody is administered about every 12 weeks.

In some embodiments, the anti-C1s antibody is additionally administered about 4 weeks after the first dose. In some embodiments, about 3 g to about 5 g of the anti-C1s antibody is administered about 4 weeks after the first dose. In some embodiments, about 3.5 g of the anti-C1s antibody is administered about 4 weeks after the first dose. In some embodiments, about 3 g, about 3.5 g, about 4 g, about 4.5 g, or about 4.5 g of the anti-C1s antibody is administered about 4 weeks after the first dose.

In some embodiments, about 3 g to about 5 g of the antibody is administered on Day 1 and about every 10, 12, 14, or 16 weeks thereafter, and about 3 g to about 5 g of the antibody is additionally administered on or about Day 29. In some embodiments, about 3 g to about 5 g of the antibody is administered intravenously on Day 1 and about every 10, 12, 14, or 16 weeks thereafter, and about 3 g to about 5 g of the antibody is additionally administered intravenously on or about Day 29.

In some embodiments, about 3 g to about 5 g of the antibody is administered on Day 1 and about every 12 weeks thereafter, and about 3 g to about 5 g of the antibody is additionally administered on or about Day 29. In some embodiments, about 3 g to about 5 g of the antibody is administered intravenously on Day 1 and about every 12 weeks thereafter, and about 3 g to about 5 g of the antibody is additionally administered intravenously on or about Day 29.

In some embodiments, about 3 g, about 3.5 g, about 4 g, about 4.5 g, or about 5 g of the antibody is administered on Day 1 and about every 10, 12, 14, or 16 weeks thereafter, and about 3 g, about 3.5 g, about 4 g, about 4.5 g, or about 5 g of the antibody is additionally administered on or about Day 29. In some embodiments, about 3 g, about 3.5 g, about 4 g, about 4.5 g, or about 5 g of the antibody is administered intravenously on Day 1 and about every 10, 12, 14, or 16 weeks thereafter, and about 3 g, about 3.5 g, about 4 g, about 4.5 g, or about 5 g of the antibody is additionally administered intravenously on or about Day 29.

In some embodiments, about 3 g, about 3.5 g, about 4 g, about 4.5 g, or about 5 g of the antibody is administered on Day 1 and about every 12 weeks thereafter, and about 3 g, about 3.5 g, about 4 g, about 4.5 g, or about 5 g of the antibody is additionally administered on or about Day 29. In some embodiments, about 3 g, about 3.5 g, about 4 g, about 4.5 g, or about 5 g of the antibody is administered intravenously on Day 1 and about every 12 weeks thereafter, and about 3 g, about 3.5 g, about 4 g, about 4.5 g, or about 5 g of the antibody is additionally administered intravenously on or about Day 29.

In some embodiments, about 3.5 g of the antibody is administered on Day 1 and about every 10, 12, 14, or 16 weeks thereafter, and about 3.5 g of the antibody is additionally administered on or about Day 29. In some embodiments, about 3.5 g of the antibody is administered intravenously on Day 1 and about every 10, 12, 14, or 16 weeks thereafter, and about 3.5 g of the antibody is additionally administered intravenously on or about Day 29.

In some embodiments, about 3.5 g of the antibody is administered on Day 1 and about every 12 weeks thereafter, and about 3.5 g of the antibody is additionally administered on or about Day 29. In some embodiments, about 3.5 g of the antibody is administered intravenously on Day 1 and about every 12 weeks thereafter, and about 3.5 g of the antibody is additionally administered intravenously on or about Day 29.

In some embodiments, about 3 g to about 5 g of the anti-C1s antibody is administered to the subject about every 12 weeks for a period of time from about 12 weeks to 1 year, e.g., from about 12 weeks to about 24 weeks, from about 6 months to about 9 months, or from about 6 months to 1 year. In some cases, about 3 g to about 5 g of the anti-C1s antibody is administered to the subject about every twelve weeks for a period of time of more than 1 year. For example, in some embodiments, about 3 g to about 5 g of the anti-C1s antibody is administered to the subject about every 12 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, about 3 g, about 3.5 g, about 4 g, about 4.5 g, or about 5 g of the anti-C1s antibody is administered to the subject about every 12 weeks for a period of time from about 12 weeks to 1 year, e.g., from about 12 weeks to about 24 weeks, from about 6 months to about 9 months, or from about 6 months to 1 year. In some cases, about 3 g, about 3.5 g, about 4 g, about 4.5 g, or about 5 g of the anti-C1s antibody is administered to the subject every twelve weeks for a period of time of more than 1 year. For example, in some embodiments, about 3 g, about 3.5 g, about 4 g, about 4.5 g, or about 5 g of the anti-C1s antibody is administered to the subject about every 12 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, about 3.5 g of the anti-C1s antibody is administered to the subject about every 12 weeks for a period of time from about 12 weeks to 1 year, e.g., from about 12 weeks to about 24 weeks, from about 6 months to about 9 months, or from about 6 months to 1 year. In some cases, about 3.5 g of the anti-C1s antibody is administered to the subject about every twelve weeks for a period of time of more than 1 year. For example, in some embodiments, about 3.5 g of the anti-C1s antibody is administered to the subject about every 12 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, about 3 g to about 5 g of the anti-C1s antibody is administered to the subject about every 12 weeks for a period of time from about 12 weeks to 1 year, e.g., from about 12 weeks to about 24 weeks, from about 6 months to about 9 months, or from about 6 months to 1 year, and about 3 g to about 5 g of the antibody is additionally administered on or about Day 29. In some cases, about 3 g to about 5 g of the anti-C1s antibody is administered to the subject about every twelve weeks for a period of time of more than 1 year, and about 3 g to about 5 g of the antibody is additionally administered on or about Day 29. For example, in some embodiments, about 3 g to about 5 g of the anti-C1s antibody is administered to the subject about every 12 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years, and about 3 g to about 5 g of the antibody is additionally administered on or about Day 29.

In some embodiments, about 3 g, about 3.5 g, about 4 g, about 4.5 g, or about 5 g of the anti-C1s antibody is administered to the subject about every 12 weeks for a period of time from about 12 weeks to 1 year, e.g., from about 12 weeks to about 24 weeks, from about 6 months to about 9 months, or from about 6 months to 1 year, and about 3 g, about 3.5 g, about 4 g, about 4.5 g, or about 5 g of the antibody is additionally administered on or about Day 29. In some cases, about 3 g, about 3.5 g, about 4 g, about 4.5 g, or about 5 g of the anti-C1s antibody is administered to the subject every twelve weeks for a period of time of more than 1 year, and about 3 g, about 3.5 g, about 4 g, about 4.5 g, or about 5 g of the antibody is additionally administered on or about Day 29. For example, in some embodiments, about 3 g, about 3.5 g, about 4 g, about 4.5 g, or about 5 g of the anti-C1s antibody is administered to the subject about every 12 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years, and about 3 g, about 3.5 g, about 4 g, about 4.5 g, or about 5 g of the antibody is additionally administered on or about Day 29.

In some embodiments, about 3.5 g of the anti-C1s antibody is administered to the subject about every 12 weeks for a period of time from about 12 weeks to 1 year, e.g., from about 12 weeks to about 24 weeks, from about 6 months to about 9 months, or from about 6 months to 1 year, and about 3.5 g of the antibody is additionally administered on or about Day 29. In some cases, about 3.5 g of the anti-C1s antibody is administered to the subject about every twelve weeks for a period of time of more than 1 year, and about 3.5 g of the antibody is additionally administered on or about Day 29. For example, in some embodiments, about 3.5 g of the anti-C1s antibody is administered to the subject about every 12 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years, and about 3.5 g of the antibody is additionally administered on or about Day 29.

In some embodiments, the present disclosure provides a method of treating CAD in a subject in need thereof, comprising administering an effective dose of an anti-C1s antibody to the subject, where the subject has a plasma concentration of the antibody of at least about 100 μg/mL, at least about 200 μg/mL, at least about 300 μg/mL, at least about 400 μg/mL, at least about 500 μg/mL, at least about 600 μg/mL, at least about 700 μg/mL, at least about 800 μg/mL, at least about 900 μg/mL, at least about 1000 μg/mL, at least about 1100 μg/mL, at least about 1200 μg/mL, or at least about 1300 μg/mL. The plasma concentration of the anti-C1s antibody in the subject can be measured using techniques known in the art. In some embodiments, the anti-C1s antibody is measured using a direct binding Enzyme-Linked Immunosorbent Assay (ELISA). In some embodiments, the anti-C1s antibody is measured using an indirect ELISA. In some embodiments, the anti-C1s antibody is measured using a sandwich ELISA. In some embodiments, the anti-C1s antibody is measured using a competitive ELISA.

In some embodiments, the present disclosure provides a method of increasing the number of reticulocytes in the blood of a subject having CAD, comprising administering an anti-C1s antibody to the subject. In some embodiments, the anti-C1s antibody increases the number of reticulocytes in the blood of the subject after the administration at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2.0 fold, at least about 2.1 fold, at least about 2.2 fold, at least about 2.3 fold, at least about 2.4 fold, at least about 2.5 fold, at least about 2.6 fold, at least about 2.7 fold, at least about 2.8 fold, at least about 2.9 fold, at least about 3.0 fold, at least about 4 fold, at least about 5 fold, at least about 6 fold, at least about 7 fold, at least about 8 fold, at least about 9 fold, or at least about 10 fold.

In some embodiments, the anti-C1s antibody increases the number of reticulocytes in the blood of the subject within about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 2 weeks, about 3 weeks, about 4 weeks, about 5 weeks, about 6 weeks, about 7 weeks, about 8 weeks, about 9 weeks, about 10 weeks, about 11 weeks, or about 12 weeks of the administration.

In some embodiments, the present disclosure provides a method of decreasing the level of lactate dehydrogenase (LDH) in a subject having CAD, comprising administering an anti-C1s antibody to the subject. In some embodiments, the anti-C1s antibody decreases the level of LDH to about the normal reference range (about 105-333 IU/L). In some embodiments, the anti-C1s antibody decreases the total level of bilirubin to about 333 IU/L or below.

In some embodiments, the anti-C1s antibody decreases the level of LDH in the subject within about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, about 7 days, about 8 days, about 9 days, about 10 days, about 11 days, about 12 days about 13 days, about 14 days, about 2 weeks, about 3 weeks, about 4 weeks, about 5 weeks, about 6 weeks, about 7 weeks, about 8 weeks, about 9 weeks, about 10 weeks, about 11 weeks, or about 12 weeks of the administration.

In some embodiments, the present disclosure provides a method of increasing the level of hemoglobin a subject having CAD, comprising administering an anti-C1s antibody to the subject. In some embodiments, the anti-C1s antibody increases the level of hemoglobin in the subject after administration by at least about 1.0 g/dL, 1.1 g/dL, 1.2 g/dL, 1.3 g/dL, 1.4 g/dL, 1.5 g/dL, 1.6 g/dL, 1.7 g/dL, 1.8 g/dL, 1.9 g/dL, 2.0 g/dL, 2.1 g/dL, 2.2 g/dL, 2.3 g/dL, 2.4 g/dL, 2.5 g/dL, 2.6 g/dL, 2.7 g/dL, 2.8 g/dL, 2.9 g/dL, 3.0 g/dL, 3.1 g/dL, 3.2 g/dL, 3.3 g/dL, 3.4 g/dL, 3.5 g/dL, 3.6 g/dL, 3.7 g/dL, 3.8 g/dL, 3.9 g/dL, 4.0 g/dL, 4.1 g/dL, 4.2 g/dL, 4.3 g/dL, 4.4 g/dL, or 4.5 g/dL. In some embodiments, the anti-C1s antibody increases the total level of hemoglobin in the subject after the administration to at least about 10.0 g/dL, at least about 10.1 g/dL, at least about 10.2 g/dL, at least about 10.3 g/dL, at least about 10.4 g/dL, at least about 10.5 g/dL, at least about 10.6 g/dL, at least about 10.7 g/dL, at least about 10.8 g/dL, at least about 10.9 g/dL, at least about 11.0 g/dL, at least about 11.1 g/dL, at least about 11.2 g/dL, at least about 11.3 g/dL, at least about 11.4 g/dL, at least about 11.5 g/dL, at least about 11.6 g/dL, at least about 11.7 g/dL, at least about 11.8 g/dL, at least about 11.9 g/dL, at least about 12.0 g/dL, at least about 12.1 g/dL, at least about 12.2 g/dL, at least about 12.3 g/dL, at least about 12.4 g/dL, at least about 12.5 g/dL, at least about 12.6 g/dL, at least about 12.7 g/dL, at least about 12.8 g/dL, at least about 12.9 g/dL, at least about 13.0 g/dL, at least about 13.1 g/dL, at least about 13.2 g/dL, at least about 13.3 g/dL, at least about 13.4 g/dL, at least about 13.5 g/dL, at least about 13.6 g/dL, at least about 13.7 g/dL, at least about 13.8 g/dL, at least about 13.9 g/dL, at least about 14.0 g/dL, at least about 14.1 g/dL, at least about 14.2 g/dL, at least about 14.3 g/dL, at least about 14.4 g/dL, at least about 14.5 g/dL, at least about 14.6 g/dL, at least about 14.7 g/dL, at least about 14.8 g/dL, at least about 14.9 g/dL, at least about 15.0 g/dL, at least about 15.1 g/dL, at least about 15.2 g/dL, at least about 15.3 g/dL, at least about 15.4 g/dL, at least about 15.5 g/dL, at least about 15.6 g/dL, at least about 15.7 g/dL, at least about 15.8 g/dL, at least about 15.9 g/dL, at least about 16.0 g/dL, at least about 16.1 g/dL, at least about 16.2 g/dL, at least about 16.3 g/dL, at least about 16.4 g/dL, at least about 16.5 g/dL, at least about 16.6 g/dL, at least about 16.7 g/dL, at least about 16.8 g/dL, at least about 16.9 g/dL, at least about 17.0 g/dL, at least about 17.1 g/dL, at least 17.2 g/dL, at least about 17.3 g/dL, at least about 17.4 g/dL, at least about 17.5 g/dL, at least about 17.6 g/dL, at least about 17.7 g/dL, at least about 17.8 g/dL, at least about 17.9 g/dL, or at least about 18.0 g/dL.

In some embodiments, the anti-C1s antibody increases the level of hemoglobin in the subject within about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, about 7 days, about 8 days, about 9 days, about 10 days, about 11 days, about 12 days about 13 days, about 14 days, about 2 weeks, about 3 weeks, about 4 weeks, about 5 weeks, about 6 weeks, about 7 weeks, about 8 weeks, about 9 weeks, about 10 weeks, about 11 weeks, or about 12 weeks of the administration.

In some embodiments, the present disclosure provides a method of decreasing the level of bilirubin in a subject having CAD, comprising administering an anti-C1s antibody to the subject. In some embodiments, the anti-C1s antibody decreases the total level of bilirubin to about the normal reference range (about 1.71 to about 20.5 μmol/L). In some embodiments, the anti-C1s antibody decreases the total level of bilirubin to about 20.5 μmol/L or below.

In some embodiments, the anti-C1s antibody decreases the total level of bilirubin in the subject within about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, about 7 days, about 8 days, about 9 days, about 10 days, about 11 days, about 12 days about 13 days, about 14 days, about 2 weeks, about 3 weeks, about 4 weeks, about 5 weeks, about 6 weeks, about 7 weeks, about 8 weeks, about 9 weeks, about 10 weeks, about 11 weeks, or about 12 weeks of the administration.

In some embodiments, the present disclosure provides a method of inhibiting the classical complement pathway (e.g., in a fluid, tissue, or organ in the individual) by at least about 75%, at least about 80%, at least about 85%, or at least about 90% in a subject having CAD, comprising administering an anti-C1s antibody to the subject. In some embodiments, the classical complement pathway is inhibited by at least about 90%. In some embodiments, the classical complement pathway is inhibited by about 90%, about 91%, about 92%, about 93%, about 94%, about 95%, about 96%, about 97%, about 98%, or about 99%. The level of activity of the classical complement pathway can be determined using any of a variety of methods. As one non-limiting example, the activity of the classical complement pathway can be determined ex vivo, e.g., by determining the level of activity of the classical complement pathway in a blood, serum, or plasma sample obtained from the individual. For example, the classical complement pathway in the blood, serum, or plasma sample can be activated ex vivo, and the amount of a complement component cleavage product (such as C5b-9) generated by such activation can be determined. In some embodiments, the level of activity of the classical complement pathway is determined using the Wieslab® Complement System Classical Pathway assay.

In some embodiments, the anti-C1s antibody inhibits the classical complement pathway in the subject within about 1 hour, 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, about 7 days, about 8 days, about 9 days, about 10 days, about 11 days, about 12 days about 13 days, about 14 days, about 2 weeks, about 3 weeks, about 4 weeks, about 5 weeks, about 6 weeks, about 7 weeks, about 8 weeks, about 9 weeks, about 10 weeks, about 11 weeks, or about 12 weeks of the administration.

In some embodiments, the present disclosure provides a method of decreases the 50% hemolytic complement activity (CH50) level in a subject having CAD, comprising administering an anti-C1s antibody to the subject. The CH50 assay is a standard clinical test used to measure the complement mediated hemolytic capacity of a serum sample. In some embodiments, the CH50 level is decreased by about 10-20 IU/mL, by about 10-15 IU/mL, or by about 15-20 IU/mL. In some embodiments, the (CH50) level is decreased by 10, 11, 12, 13, 14, 15, 16, 17, 18, 19, or 20 IU/mL. In some embodiments, the (CH50) level is decreased to less than about 10 IU/mL, less than about 9 IU/mL, less than about 8 IU/mL, less than about 7 IU/mL, less than about 6 IU/mL, or less than about 5 IU/mL.

In some embodiments, the anti-C1s antibody decreases the CH50 level in the subject within about 1 hour, 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, about 7 days, about 8 days, about 9 days, about 10 days, about 11 days, about 12 days about 13 days, about 14 days, about 2 weeks, about 3 weeks, about 4 weeks, about 5 weeks, about 6 weeks, about 7 weeks, about 8 weeks, about 9 weeks, about 10 weeks, about 11 weeks, or about 12 weeks of the administration.

In some embodiments, inclusion criteria are as follows. Participants are male and female adults who are ≥18 years of age at the time of signing the informed consent and display the following characteristics:

1. Confirmed diagnosis of CAD based on the following criteria:
   chronic hemolysis;
   polyspecific direct antiglobulin test (DAT) positive status;
   monospecific DAT strongly positive for C3d;
   cold agglutinin [CAg] titer≥64 at 4° C.;
   IgG DAT≤1+; and
   No overt malignant disease
2. Hgb levels ≤10.0 g/dL at both Day −42 and Day −21 of the Screening period; if a patient receives a transfusion during Screening, the Hgb value for eligibility must be obtained at least 28 days following the transfusion.
3. Bilirubin levels above the normal reference range, including participants with Gilbert Syndrome
4. Ferritin levels above the lower limit of normal. Concurrent treatment with iron supplementation is permitted if the participant has been on a stable dose during the previous 4 weeks.
5. Presence of CAD-related fatigue of at least moderate degree based on "Fatigue Screener" performed on Day −42 of the Screening Period. That is, participants must report having Moderate fatigue, Severe fatigue, or Very severe fatigue related to CAD in the past month.

In some embodiments, methods of the present disclosure prevent or delay the onset of at least one symptom of CAD in a subject. In some embodiments, a composition of the present disclosure reduces or eliminates at least one symptom of CAD in a subject. The symptom can also be the activity of C1s protein in a cell, tissue, or fluid of an individual. The symptom can also be the extent of complement activation in a cell, tissue, or fluid of an individual.

By "treatment" is meant at least an amelioration of the symptoms associated with CAD, where amelioration is used in a broad sense to refer to at least a reduction in the magnitude of a parameter, e.g., symptom, associated with CAD.

Baseline values of laboratory parameters related to anemia (Hgb) and hemolysis (bilirubin) and baseline values related to fatigue (FACIT-fatigue scale score) are defined as the mean of the assessments on Day −21 during the screening period and Day 1 before treatment administration. If a transfusion occurs during the screening period, the baseline measurements must be at least 28 days after the transfusion. In that case, any measurement within 28 days of transfusion is considered as invalid and subsequently excluded, and the baseline value is then the last valid measurements before treatment administration.

The primary treatment assessment value of laboratory parameters related to anemia is the mean of the non-missing measurements of Hgb assessed at Day 141, Day 155, and Day 169 [Weeks 21, 23, and 25].

Endpoint Response Rate: Percentage of participants who achieve a ≥2 g/dL increase from baseline based on the mean of Hgb values measured at Day 141, Day 155, and Day 169 [Weeks 21, 23, and 25], and meeting both of these two conditions: (1) absence of transfusion during the final 21 weeks; and (2) no use of protocol-prohibited CAD medication from baseline.

The primary treatment assessment value of the FACIT-fatigue scale score measurements is the mean of non-missing FACIT-fatigue scale scores assessed at the same time points, at Day 141, Day 155, and Day 169. Endpoint: Change from baseline at the primary treatment assessment time point for FACIT-Fatigue measurement.

There are three key secondary endpoints: 1. change in bilirubin from baseline at the primary treatment assessment time point; 2. change in Hgb from baseline at Day 29; and 3. change in the FACIT-fatigue scale score from baseline at Day 29. The other secondary endpoint is: mean change in bilirubin from baseline at Day 29.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., cats), herbivores (e.g., cattle, horses, and sheep), omnivores (e.g., dogs, goats, and pigs), rodentia (e.g., mice, guinea pigs, and rats), and primates (e.g., humans, chimpanzees, and monkeys). In some embodiments, the host is an individual that has a complement system, such as a mammal, fish, or invertebrate. In some embodiments, the host is a complement system-containing mammal, fish, or invertebrate companion animal, agricultural animal, work animal, zoo animal, or lab animal. In some embodiments, the host is human.

Methods of Treating CIDP

Chronic inflammatory demyelinating polyneuropathy (CIDP) is a rare, immune-mediated disease of the peripheral nervous system, characterized by loss of myelin sheath in motor and sensory nerves that manifests as weakness, hypo or areflexia, numbness, paresthesia and sensory ataxia, indicative of large sensory fiber involvement.

The diagnosis of CIDP is usually confirmed by neurophysiological evidence of peripheral nerve demyelination and ruling out other causes of demyelinating polyneuropathy or diseases that can have similar manifestations. Commonly used Expert consensus criteria for the diagnosis of CIDP have been provided by the Joint Task Force of the European Federation of Neurological Societies/Peripheral Nerve Society (EFNS/PNS) (2010) (Bergh Van den PYK., et al. European J. of Neurology 2010, 17:356-363), and a recent revision of these criteria (2021) is available (Van den Bergh et al. Eur J Neurol 2021; 28(11):3556-3583).

Activation of the complement pathway is expected to play a key role in the pathophysiology of CIDP. In CIDP patients, this pathway, an enzymatic cascade, is triggered by pathogenic autoantibodies causing inflammatory damage, ultimately driving demyelinating and inflammatory processes in the peripheral nerves that are the basis for functional disability.

By more selectively targeting a key mechanism of the disease, an anti-C1s antibody of the disclosure has the potential for an improved efficacy profile across the broad CIDP population, including patients who are refractory to standard of care (SOC) therapies.

The present disclosure provides methods of treating CIDP in a subject. CIDP may be typical or atypical (Doneddu et al., Curr Opin Neurol. 34(5): 613-624 (2021). In some embodiments, the CIDP may be typical CIDP. In some embodiments, the CIDP may be atypical CIDP. In some embodiments, atypical CIDP may present with Lewis-Sumner syndrome (LSS). In some embodiments, atypical CIDP may present with pure motor CIDP. In one aspect, the methods comprise administering to the subject a loading dose of an anti-C1s antibody followed by one or more maintenance doses of the antibody.

In some embodiments, the loading dose is a weight-based dose. In some embodiments, the loading dose of the antibody is about 50 mg/kg of the subject's body weight.

In some embodiments, a maintenance dose of the antibody is a fixed dose. In some embodiments, a maintenance dose of the antibody is between 200 mg to about 800 mg. In some embodiments, a maintenance dose of the antibody is between about 200 mg to about 300 mg, about 300 mg to about 400 mg, about 200 mg to about 500 mg, about 300 mg to about 600 mg, about 400 mg to about 800 mg or about 600 mg to about 800 mg. In some embodiments, a maintenance dose of the antibody is between about 300 mg to about 600 mg. In some embodiments, a maintenance dose of the antibody is about 300 mg, about 400 mg, about 500 mg, or about 600 mg. In some embodiments, a maintenance dose of the antibody is about 300 mg. In some embodiments, a maintenance dose of the antibody is about 600 mg.

In some embodiments, a maintenance dose of the antibody is a fixed dose. In some embodiments, a maintenance dose of the antibody is between about 200 mg to about 800 mg. In some embodiments, a maintenance dose of the antibody is between about 200 mg to about 300 mg, about 300 mg to about 400 mg, about 200 mg to about 500 mg, about 300 mg to about 600 mg, about 400 mg to about 800 mg or about 600 mg to about 800 mg. In some embodiments, a maintenance dose of the antibody is between about 300 mg to about 600 mg. In some embodiments, a maintenance dose of the antibody is about 300 mg, about 400 mg, about 500 mg, or about 600 mg. In some embodiments, a maintenance dose of the antibody is about 300 mg. In some embodiments, a maintenance dose of the antibody is about 600 mg.

In some embodiments, the one or more maintenance doses are administered about every week (i.e., weekly), every 2 weeks, every 4 weeks, or every 12 weeks.

In some embodiments, the loading dose is administered on Day 1, followed by administration of the maintenance dose about weekly starting on Day 8. In some embodiments, the loading dose is administered intravenously on Day 1, followed by subcutaneous administration of the maintenance dose about weekly starting on Day 8.

In some embodiments, the loading dose is administered on Day 1, followed by administration of a maintenance dose of between about 200 mg to about 800 mg about weekly starting on Day 8. In some embodiments, the loading dose is administered intravenously on Day 1, followed by subcutaneous administration of a maintenance dose of between about 200 mg to about 800 mg about weekly starting on Day 8.

In some embodiments, the loading dose is administered on Day 1, followed by administration of a maintenance dose of between about 1000 mg to about 8000 mg about every 2 weeks, about every 4 weeks, or about every 12 weeks starting on Day 8 or Day 29. In some embodiments, the loading dose is administered intravenously on Day 1, followed by subcutaneous administration of a maintenance dose of between about 1000 mg to about 8000 mg about every 2 weeks, about every 4 weeks, or about every 12 weeks starting on Day 8 or Day 29.

In some embodiments, the loading dose is administered on Day 1, followed by administration of a maintenance dose of between about 300 mg to about 600 mg about weekly starting on Day 8. In some embodiments, the loading dose is administered intravenously on Day 1, followed by subcutaneous administration of a maintenance dose of between about 300 mg to about 600 mg about weekly starting on Day 8.

In some embodiments, the loading dose is administered on Day 1, followed by administration of a maintenance dose of between about 1200 mg to about 7200 mg about every 4 weeks or about every 12 weeks starting on Day 29. In some embodiments, the loading dose is administered intravenously on Day 1, followed by subcutaneous administration of a maintenance dose of between about 1200 mg to about 7200 mg about every 4 weeks or about every 12 weeks starting on Day 29.

In some embodiments, the loading dose is administered on Day 1, followed by administration of a maintenance dose of about 300 mg about weekly starting on Day 8. In some embodiments, the loading dose is administered intravenously on Day 1, followed by subcutaneous administration of a maintenance dose of about 300 mg about weekly starting on Day 8.

In some embodiments, the loading dose is administered on Day 1, followed by administration of a maintenance dose of about 600 mg about weekly starting on Day 8. In some embodiments, the loading dose is administered intravenously on Day 1, followed by subcutaneous administration of a maintenance dose of about 600 mg about weekly starting on Day 8.

In some embodiments, the loading dose is administered on Day 1, followed by administration of a maintenance dose of about 600 mg about every 2 weeks starting on Day 8. In some embodiments, the loading dose is administered intravenously on Day 1, followed by subcutaneous administration of a maintenance dose of about 600 mg about every 2 weeks starting on Day 8.

In some embodiments, the loading dose is administered on Day 1, followed by administration of a maintenance dose of about 1200 mg about every 2 weeks starting on Day 8. In some embodiments, the loading dose is administered intravenously on Day 1, followed by subcutaneous administration of a maintenance dose of about 1200 mg about every 2 weeks starting on Day 8.

In some embodiments, the loading dose is administered on Day 1, followed by administration of a maintenance dose of about 1200 mg about every 4 weeks starting on Day 29. In some embodiments, the loading dose is administered intravenously on Day 1, followed by subcutaneous administration of a maintenance dose of about 1200 mg about every 4 weeks starting on Day 29.

In some embodiments, the loading dose is administered on Day 1, followed by administration of a maintenance dose of about 2400 mg about every 4 weeks starting on Day 29. In some embodiments, the loading dose is administered intravenously on Day 1, followed by subcutaneous administration of a maintenance dose of about 2400 mg about every 4 weeks starting on Day 29.

In some embodiments, the loading dose is administered on Day 1, followed by administration of a maintenance dose of about 3600 mg about every 12 weeks starting on Day 29. In some embodiments, the loading dose is administered intravenously on Day 1, followed by subcutaneous administration of a maintenance dose of about 3600 mg about every 12 weeks starting on Day 29.

In some embodiments, the loading dose is administered on Day 1, followed by administration of a maintenance dose of about 7200 mg about every 12 weeks starting on Day 29. In some embodiments, the loading dose is administered intravenously on Day 1, followed by subcutaneous administration of a maintenance dose of about 7200 mg every 12 weeks starting on Day 29.

In some embodiments, a maintenance dose of between about 200 mg to about 800 mg of the anti-C1s antibody is administered to the subject about weekly for a period of time from about 4 weeks to 1 year, e.g., from about 4 weeks to about 8 weeks, from about 2 months to about 6 months, from about 6 months to about 9 months, or from about 6 months to 1 year. In some embodiments, a maintenance dose of between about 200 mg to about 800 mg of the anti-C1s antibody is administered to the subject about weekly for a period of time of more than 1 year. For example, in some embodiments, a maintenance dose of between about 200 mg to about 800 mg of the anti-C1s antibody is administered to the subject about weekly for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, a maintenance dose of between about 1000 mg to about 8000 mg of the anti-C1s antibody is administered to the subject about every 2 weeks, or every 4 weeks, or about every 12 weeks for a period of time from about 4 weeks to 1 year, e.g., from about 4 weeks to about 8 weeks, from about 2 months to about 6 months, from about 6 months to about 9 months, or from about 6 months to 1 year. In some embodiments, a maintenance dose of between about 1000 mg to about 8000 mg of the anti-C1s antibody is administered to the subject about every 2 weeks, or about every 4 weeks, or about every 12 weeks for a period of time of more than 1 year. For example, in some embodiments, a maintenance dose of between about 1000 mg to about 8000 mg of the anti-C1s antibody is administered to the subject about every 2 weeks, or about every 4 weeks, or about every 12 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, a maintenance dose of between about 300 mg to about 600 mg of the anti-C1s antibody is administered to the subject about weekly for a period of time from about 4 weeks to 1 year, e.g., from about 4 weeks to about 8 weeks, from about 2 months to about 6 months, from about 6 months to about 9 months, or from about 6 months to 1 year. In some embodiments, a maintenance dose of between about 300 mg to about 600 mg of the anti-C1s antibody is administered to the subject about weekly for a period of time of more than 1 year. For example, in some embodiments, a maintenance dose of between about 300 mg to about 600 mg of the anti-C1s antibody is administered to the subject about weekly for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, a maintenance dose of between about 1200 mg to about 7200 mg of the anti-C1s antibody is administered to the subject about every 2 weeks, or about every 4 weeks, or about every 12 weeks for a period of time from about 4 weeks to 1 year, e.g., from about 4 weeks to about 8 weeks, from about 2 months to about 6 months, from about 6 months to about 9 months, or from about 6 months to 1 year. In some embodiments, a maintenance dose of between about 1200 mg to about 7200 mg of the anti-C1s antibody is administered to the subject about every 2 weeks, or about every 4 weeks, or about every 12 weeks for a period of time of more than 1 year. For example, in some embodiments, a maintenance dose of between about 1200 mg to about 7200 mg of the anti-C1s antibody is administered to the subject about every 2 weeks, or about every 4 weeks, or about every 12 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, a maintenance dose of about 300 mg of the anti-C1s antibody is administered to the subject about weekly for a period of time from about 4 weeks to 1 year, e.g., from about 4 weeks to about 8 weeks, from about 2 months to about 6 months, from about 6 months to about 9 months, or from about 6 months to 1 year. In some embodiments, a maintenance dose of about 300 mg of the anti-C1s antibody is administered to the subject about weekly for a period of time of more than 1 year. For example, in some embodiments, a maintenance dose of about 300 mg of the anti-C1s antibody is administered to the subject about weekly for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, a maintenance dose of about 600 mg of the anti-C1s antibody is administered to the subject about weekly or about every 2 weeks for a period of time from about 4 weeks to 1 year, e.g., from about 4 weeks to about 8 weeks, from about 2 months to about 6 months, from about 6 months to about 9 months, or from about 6 months to 1 year. In some embodiments, a maintenance dose of about 600 mg of the anti-C1s antibody is administered to the subject about weekly or about every 2 weeks for a period of time of more than 1 year. For example, in some embodiments, a maintenance dose of about 600 mg of the anti-C1s antibody is administered to the subject about weekly or about every 2 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, a maintenance dose of about 1200 mg of the anti-C1s antibody is administered to the subject about every 2 weeks or about every 4 weeks for a period of time from about 4 weeks to 1 year, e.g., from about 4 weeks to about 8 weeks, from about 2 months to about 6 months, from about 6 months to about 9 months, or from about 6 months to 1 year. In some embodiments, a maintenance dose of about 1200 mg of the anti-C1s antibody is administered to the subject about every 2 weeks or about every 4 weeks for a period of time of more than 1 year. For example, in some embodiments, a maintenance dose of about 1200 mg of the anti-C1s antibody is administered to the subject about ever 2 weeks or about every 4 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, a maintenance dose of about 2400 mg of the anti-C1s antibody is administered to the subject about every 4 weeks for a period of time from about 4 weeks to 1 year, e.g., from about 4 weeks to about 8 weeks, from about 2 months to about 6 months, from about 6 months to about 9 months, or from about 6 months to 1 year. In some embodiments, a maintenance dose of about 2400 mg of the anti-C1s antibody is administered to the subject about every 4 weeks for a period of time of more than 1 year. For example, in some embodiments, a maintenance dose of about 2400 mg of the anti-C1s antibody is administered to the subject about every 4 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, a maintenance dose of about 3600 mg of the anti-C1s antibody is administered to the subject about every 12 weeks for a period of time from about 12 weeks to 1 year, e.g., from about 12 weeks to about 8 weeks, from about 2 months to about 6 months, from about 6 months to about 9 months, or from about 6 months to 1 year. In some embodiments, a maintenance dose of about 3600 mg of the anti-C1s antibody is administered to the subject about every 12 weeks for a period of time of more than 1 year. For example, in some embodiments, a maintenance dose of about 3600 mg of the anti-C1s antibody is administered to the subject about every 12 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, a maintenance dose of about 7200 mg of the anti-C1s antibody is administered to the subject about every 12 weeks for a period of time from about 12 weeks to 1 year, e.g., from about 12 weeks to about 8 weeks, from about 2 months to about 6 months, from about 6 months to about 9 months, or from about 6 months to 1 year. In some embodiments, a maintenance dose of about 7200 mg of the anti-C1s antibody is administered to the subject about every 12 weeks for a period of time of more than 1 year. For example, in some embodiments, a maintenance dose of about 7200 mg of the anti-C1s antibody is administered to the subject about every 12 weeks for a period of time from 1 year to 50 years, e.g., from 1 year to 2 years, from 2 years to 5 years, from 5 years to 10 years, from 10 years to 20 years, from 20 years to 30 years, from 30 years to 40 years, or from 40 years to 50 years.

In some embodiments, a one-time 50 mg/kg intravenous loading dose is administered on Day 1 and subcutaneous (SC) doses are administered with a syringe, or pre-filled syringe, or autoinjector, or large-volume drug delivery system. In some embodiments, the SC doses administered are 300 mg qw, 600 mg qw, 600 mg q2w, 1200 mg q2w, 1200 mg q4w, 2400 mg q4w, 3600 mg q12w, or 7200 mg q12w. In some embodiments, SC doses are administered with a syringe, or pre-filled syringe, or autoinjector, or large-volume drug delivery system until end of treatment.

In some embodiments, the subject is refractory to another CIDP treatment, also referred to herein as "Standard of Care (SOC)-refractory." SOC-refractory patients are patients with evidence of failure or inadequate response to SOC, defined as no clinically meaningful improvement and persistent Inflammatory Neuropathy Cause and Treatment (INCAT) score ≥2 after treatment for a minimum of 12 weeks on SOC (Hughes et al. Ann Neurol. 2001; 50(2):195-201), or patients who are unable to receive or continue treatment with immunoglobulins or corticosteroids due to side effects. In some embodiments, clinically meaningful improvement (and deterioration) is defined, respectively, as one of the following: ≥1-point decrease (increase) in adjusted INCAT score, ≥4 points increase (decrease) in Inflammatory Rasch-built Overall Disability Scale (I-RODS) total score (van Nes et al. Neurology. 2011; 76(4):337-45), ≥3 points increase (decrease) in Medical Research Council (MRC) Sum score, ≥8 kilopascal improvement (decrease) in mean grip strength (one hand), or an equivalent improvement (deterioration) based on information documented in medical records.

In some embodiments, the subject is being treated with another CIDP treatment, also referred to herein as "SOC-Treated." In some embodiments, the subject has received another CIDP treatment within about one week of the loading dose or is concomitantly receiving another CIDP treatment. SOC-Treated patients are patients on stable SOC therapy, who showed documented evidence of objective and clinically meaningful response, and evidence of clinically meaningful deterioration on interruption or dose reduction of SOC therapy. In some embodiments, clinically meaningful improvement (and deterioration) is defined, respectively, as one of the following: ≥1-point decrease (increase) in adjusted INCAT score, ≥4 points increase (decrease) in I-RODS total score, ≥3 points increase (decrease) in MRC Sum score, ≥8 kilopascal improvement (decrease) in mean grip strength (one hand), or an equivalent improvement (deterioration) based on information documented in medical records.

In some embodiments, the subject is naïve to CIDP treatment, also referred to herein as "SOC-naïve." SOC-naïve patients are patients without previous treatment for CIDP or patients who received immunoglobulins (IVIg or SCIg) or corticosteroids but were stopped for reasons other than lack of response or side effects. Patients should not have received treatment with immunoglobulins (IVIg or SCIg) or corticosteroids for at least 6 months prior to screening.

The other CIDP treatments may be any known CIDP treatment. In some embodiments, the other CIDP treatment is intravenous immunoglobulin (IVIg), subcutaneous immunoglobulin (SCIg), corticosteroids (e.g., prednisone, prednisolone, methylprednisolone), cyclophosphamide, rituximab, toclizumab, azathioprine, tacrolimus, plasma exchange, mycophenolate mofetil, cyclosporine, plasma exchange, or a combination thereof. Corticosteroid treatment may be oral or intravenous.

In some embodiments, administration of the anti-C1s antibody improves the adjusted INCAT disability score. In some embodiments, administration of the anti-C1s antibody decreases the INCAT score by 1 point or more. In some embodiments, the subject is SOC-refractory. In some embodiments, the subject is SOC-naïve. The INCAT disability scale is a validated instrument to measure disability in patients with CIDP. It has been used in large clinical trials leading to approval of IVIg and SCIg (PATH). The total INCAT score is obtained by adding the points corresponding to the arm and leg parts.

In some embodiments, the primary endpoint is the percentage of participants with a 1 point or more decrease relative to baseline (response) in adjusted INCAT score at Week 24. The adjusted INCAT disability score is identical to the INCAT disability score, except for the exclusion of changes in upper-limb function from 0 (normal) to 1 (minor symptoms or signs in 1 or both arms, but not affecting any of the functions listed in the scale), or from 1 to 0.

In some embodiments, inclusion and exclusion criteria are as follows. Participants are male and female adults (≥18 years of age) with CIDP or possible CIDP criteria, based on EAN/PNS Task Force CIDP guidelines, second revision (2021). Participants with CIDP must have typical CIDP, pure motor CIDP, or Lewis-Summer Syndrome, and not other polyneuropathy, including pure sensory CIDP or distal CIDP.

Participants must also:
i. Have responded to IVIg in the past. Response must be an objective clinically meaningful improvement defined by at least one of the following: ≥1-point decrease in adjusted INCAT score, ≥4 points increase in I-RODS total score, ≥3 points increase in MRC Sum score, ≥8 kilopascal improvement in mean grip strength (one hand), or an equivalent improvement based on information documented in medical records and per the PI's judgement.
ii. Be receiving treatment with IVIg within a 20% range of the standard maintenance dosing regimen. Standard maintenance dosing is defined as 0.4-1 g/kg every 2-6 weeks (EAN/PNS 2021 guidelines).
iii. Be on stable maintenance dose of IVIg, defined as no change greater than 10% in frequency or dose of IVIg within 8 weeks prior to screening, and remaining stable until baseline.
iv. Have residual disability, defined as an adjusted INCAT score of 2-9 at screening that is confirmed at baseline.
v. Have been previously vaccinated against encapsulated organisms.

In some embodiments, administration of the anti-C1s antibody prevents relapse. Relapse is defined as an increase in the adjusted INCAT disability score of 1 or more. In some embodiments, administration of the anti-C1s antibody prevents relapse following withdrawal of another CIDP treatment.

In some embodiments, administration of the anti-C1s antibody improves the MRC sum score by 3 points or more.

In some embodiments, administration of the anti-C1s antibody improves the I-RODS score by 4 points or more.

In some embodiments, administration of the anti-C1s antibody improves mean grip strength (e.g., one hand) by 8 kilopascals or more.

In some embodiments, the present disclosure provides a method of treating CIDP in a subject in need thereof, comprising administering an effective dose of an anti-C1s antibody to the subject, where the subject has a plasma concentration of the antibody of at least about 100 μg/mL, at least about 200 μg/mL, at least about 300 μg/mL, at least about 400 μg/mL, at least about 500 μg/mL, at least about 600 μg/mL, at least about 700 μg/mL, at least about 800 μg/mL, at least about 900 μg/mL, at least about 1000 μg/mL, at least about 1100 μg/mL, at least about 1200 μg/mL, at least about 1300 μg/mL, at least about 1400 μg/mL, or at least about 1500 μg/mL. The plasma concentration of the anti-C1s antibody in the subject can be measured using techniques known in the art. In some embodiments, the anti-C1s antibody is measured using a direct binding Enzyme-Linked Immunosorbent Assay (ELISA). In some embodiments, the anti-C1s antibody is measured using an indirect ELISA. In some embodiments, the anti-C1s antibody is measured using a sandwich ELISA. In some embodiments, the anti-C1s antibody is measured using a competitive ELISA.

In some embodiments, the present disclosure provides a method of inhibiting the classical complement pathway (e.g., in a fluid, tissue, or organ in the individual) by at least about 75%, at least about 80%, at least about 85%, or at least about 90% in a subject having CIDP, comprising administering an anti-C1s antibody to the subject. In some embodiments, the classical complement pathway is inhibited by at least about 90%. In some embodiments, the classical complement pathway is inhibited by about 90%, about 91%, about 92%, about 93%, about 94%, about 95%, about 96%, about 97%, about 98%, or about 99%. The level of activity of the classical complement pathway can be determined using any of a variety of methods. As one non-limiting example, the activity of the classical complement pathway can be determined ex vivo, e.g., by determining the level of activity of the classical complement pathway in a blood, serum, or plasma sample obtained from the individual. For example, the classical complement pathway in the blood, serum, or plasma sample can be activated ex vivo, and the amount of a complement component cleavage product (such as C5b-9) generated by such activation can be determined. In some embodiments, the level of activity of the classical complement pathway is determined using the Wieslab® Complement System Classical Pathway assay.

In some embodiments, the anti-C1s antibody inhibits the classical complement pathway in the subject within about 1 hour, 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about days, about 6 days, about 7 days, about 8 days, about 9 days, about 10 days, about 11 days, about 12 days about 13 days, about 14 days, about 2 weeks, about 3 weeks, about 4 weeks, about 5 weeks, about 6 weeks, about 7 weeks, about 8 weeks, about 9 weeks, about 10 weeks, about 11 weeks, or about 12 weeks of the administration.

In some embodiments, the present disclosure provides a method of decreases the 50% hemolytic complement activity (CH50) level in a subject having CIDP, comprising administering an anti-C1s antibody to the subject. The CH50 assay is a standard clinical test used to measure the complement mediated hemolytic capacity of a serum sample. In some embodiments, the CH50 level is decreased by about 10-20 IU/mL, by about 10-15 IU/mL, or by about 15-20 IU/mL. In some embodiments, the (CH50) level is decreased by 10, 11, 12, 13, 14, 15, 16, 17, 18, 19, or 20 IU/mL. In some embodiments, the (CH50) level is decreased to less than about 10 IU/mL, less than about 9 IU/mL, less than about 8 IU/mL, less than about 7 IU/mL, less than about 6 IU/mL, or less than about 5 IU/mL.

In some embodiments, the anti-C1s antibody decreases the CH50 level in the subject within about 1 hour, 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, about 7 days, about 8 days, about 9 days, about 10 days, about 11 days, about 12 days about 13 days, about 14 days, about 2 weeks, about 3 weeks, about 4 weeks, about 5 weeks, about 6 weeks, about 7 weeks, about 8 weeks, about 9 weeks, about 10 weeks, about 11 weeks, or about 12 weeks of the administration.

In some embodiments, methods of the present disclosure prevent or delay the onset of at least one symptom of CIDP in a subject. In some embodiments, a composition of the present disclosure reduces or eliminates at least one symptom of CIDP in a subject. The symptom can also be the activity of C1s protein in a cell, tissue, or fluid of an individual. The symptom can also be the extent of complement activation in a cell, tissue, or fluid of an individual.

By "treatment" is meant at least an amelioration of the symptoms associated with CIDP, where amelioration is used in a broad sense to refer to at least a reduction in the magnitude of a parameter, e.g. symptom, associated with CIDP.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., cats), herbivores (e.g., cattle, horses, and sheep), omnivores (e.g., dogs, goats, and pigs), rodentia (e.g., mice, guinea pigs, and rats), and primates (e.g., humans, chimpanzees, and monkeys). In some embodiments, the host is an individual that has a complement system, such as a mammal, fish, or invertebrate. In some embodiments, the host is a complement system-containing mammal, fish, or invertebrate companion animal, agricultural animal, work animal, zoo animal, or lab animal. In some embodiments, the host is human.

Compositions

An anti-C1s antibody is generally present in a composition, e.g., a pharmaceutical composition. A humanized anti-C1s antibody of the present disclosure can be formulated into pharmaceutical compositions by combination with appropriate pharmaceutically acceptable carriers, pharmaceutically acceptable diluents, or other pharmaceutically acceptable excipients.

Exemplary antibody concentrations in a composition of the disclosure can range from about 50 mg/mL to about 250 mg/mL, about 75 mg/mL to about 225 mg/mL, about 100 mg/mL to about 200 mg/mL, about 100 mg/mL to about 150 mg/mL, about 150 mg/mL to about 200 mg/mL, about 125 mg/mL to about 175 mg/mL, or about 140 mg/mL to about 160 mg/mL. In some embodiments, the antibody concentration in a composition of the disclosure is about 50 mg/mL, about 75 mg/mL, about 100 mg/mL, about 125 mg/mL, about 130 mg/mL, about 140 mg/mL, about 150 mg/mL, about 160 mg/mL, about 170 mg/mL, about 175 mg/mL, about 200 mg/mL, or about 250 mg/mL. In some embodiments, a composition of the disclosure comprises about 150 mg/mL of the humanized anti-C1s antibody.

A composition comprising an anti-C1s antibody, in some embodiments, comprises one or more of a stabilizer, a buffering agent, a cryoprotectant, a chelator, and a surfactant.

Suitable stabilizers include arginine or a salt thereof (e.g., arginine citrate, arginine hydrochloride, arginine oxalate, arginine phosphate, arginine succinate, or arginine tartrate), a sugar, a sugar alcohol, or an amino sugar (e.g., fructose, galactose, glucose, lactose, maltose, mannose, raffinose, sorbitol, sorbose, sucrose, galactosamine, glucosamine, N-methylglucosamine, and neuraminic acid). Other stabilizers may also be used.

Suitable buffering agents include acetate, citrate, histidine, oxalate, phosphate, succinate, and tartrate. Other buffering agents may also be used.

Suitable cryoprotectants include sucrose, ethylene glycol, dimethyl sulfoxide (DMSO), glycerol, trehalose, and propylene glycol. Other cryoprotectants may also be used.

Suitable chelators include ethylenediaminetetraacetic acid (EDTA), diethylenetriamine pentaacetate (DTPA), dihyroxy ethyl glycine, citric acid, tartaric acid, and methionine. Other chelators may also be used.

Suitable surfactants include polysorbates (e.g., polysorbate 20 (PS20), polysorbate 40 (PS40), polysorbate 60 (PS60), and polysorbate 80 (PS80)), dicarboxylic acids, oxalic acid, succinic acid, fumaric acid, phthalic acid, polyoxyethylene sorbitan monooleate, poloxamers (e.g., P188), and polyethylene glycol. Other surfactants may also be used.

A composition of the disclosure may have a pH of from about 6 to about 7.5, about 6 to about 7, about 6.5 to about 7.5, or about 6.5 to about 7.1. In some embodiments, a composition of the disclosure has a pH of about 6.0, about 6.1, about 6.2, about 6.3, about 6.4, about 6.5, about 6.6. about 6.7, about 6.8, about 6.9, about 7.0, about 7.1, about 7.2, about 7.3, about 7.4, or about 7.5. In some embodiments, a composition of the disclosure has a pH of about 6.5-7.1. In some embodiments, a composition of the disclosure has a pH of about 6.8.

A composition of the disclosure may comprise other excipients including, but not limited to, water for injection, diluents, solubilizing agents, soothing agents, additional buffers, inorganic or organic salts, antioxidants, or the like. Pharmaceutically acceptable excipients are readily available to the public. In some embodiments, a composition of the disclosure comprises no other excipients, except those described above. Other pharmaceutically acceptable carriers or excipients such as those described in Remington's Pharmaceutical Sciences 16$^{th}$ edition, Osol, A. Ed. (1980) may be included in the formulation provided that they do not adversely affect the desired characteristics of the formulation. In some embodiments, a preservative may be added. In some embodiments, the composition is substantially free of preservatives. Cryoprotectants or lyoprotectants may be included in lyophilized formulations.

A composition of the disclosure can be in a liquid form, a lyophilized form wherein the lyophilized preparation is to be reconstituted with a sterile solution prior to administration, or a liquid form reconstituted from a lyophilized form. The standard procedure for reconstituting a lyophilized composition is to add back a volume of pure water (typically equivalent to the volume removed during lyophilization);

however solutions comprising antibacterial agents can be used for the production of pharmaceutical compositions for parenteral administration; see also Chen (1992) Drug Dev Ind Pharm 18, 1311-54. In some embodiments, a composition of the disclosure is a liquid form. A liquid formulation may be ready for injection, or may be diluted prior to injection.

Routes of Administration

An antibody of the present disclosure can be administered to a subject using any available conventional methods and routes suitable for delivery of conventional drugs, including systemic or localized routes. In general, routes of administration contemplated by the disclosure include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intrathecal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

Routes of administration can be combined, if desired, or adjusted depending upon the desired effect. An antibody can be administered in a single dose or in multiple doses. In some embodiments, an antibody of the disclosure is administered intravenously. In some embodiments, an antibody of the disclosure is administered subcutaneously.

The disclosure also provides a pharmaceutical unit dosage form comprising a therapeutically effective amount of a composition of the disclosure for the treatment of one or more complement-mediated disease in a subject through administration of the dosage form to the subject. In some embodiments, the subject is a human. The term "pharmaceutical unit dosage form" refers to a physically discrete unit suitable as unitary dosages for the subjects to be treated, each unit containing a predetermined quantity of active compound calculated to produce the desired therapeutic/prophylactic effect.

The unit dosage form may be a container comprising the formulation. Suitable containers include, but are not limited to, sealed ampoules, vials (e.g., a glass vial), bottles, syringes, and test tubes. The containers may be formed from a variety of materials, such as glass or plastic, and may have a sterile access port (for example, the container may be a vial having a stopper that can be pierced by a hypodermic injection needle). In some embodiments, the container is a vial. In some embodiments, the container is a pre-filled syringe. Generally, the container should maintain the sterility and stability of the formulation.

An exemplary drug delivery device may involve a needle-based injection system as described in Table 1 of section 5.2 of ISO 11608-1:2022. As described in ISO 11608-1:2022, needle-based injection systems may be broadly distinguished into multi-dose container systems and single-dose (with partial or full evacuation) container systems. The container may be a replaceable container or an integrated non-replaceable container.

As further described in ISO 11608-1:2022, a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2022, a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2022, a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

An exemplary sleeve-triggered auto-injector with manual needle insertion is described in International Publication WO2015/004052. Example audible end-of-dose feedback mechanisms are described in International Publications WO2016/193346 and WO2016/193348. An example needle-safety mechanism after using an auto-injector is described in International Publication WO2016/193352. An example needle sheath remover mechanism for a syringe auto-injector is described in International Publication WO2016/193353. An example support mechanism for supporting an axial position of a syringe is described in International Publication WO2016/193355.

Kits and Articles of Manufacture

The present disclosure provides a kit or an article of manufacture comprising a composition of the disclosure. The kit or article of manufacture comprises a container comprising an antibody of the disclosure. The kit or article of manufacture may further comprise one or more containers comprising pharmaceutically acceptable excipients, and include other materials desirable from a commercial and user standpoint, including filters, needles and syringes. Associated with the kits can be instructions customarily included in commercial packages of therapeutic, prophylactic or diagnostic products, that contain information about, for example, the indications, usage, dosage, manufacture, administration, contra-indications, and/or warnings concerning the use of such therapeutic, prophylactic or diagnostic products. The kit can also be associated with a label that can be any kind of data carrier (e.g., a leaflet, sticker, chip, print or bar code) comprising information. In certain embodiments, the instructions as listed above can be comprised in or on the label. The kit can further comprise a device for administration of the formulation, and particularly a device that contains the composition, i.e., a pre-filled device such as, but not limited to, a pre-filled syringe or a pre-filled autoinjector. The kit can also comprise a container comprising the antibody, i.e., a pre-filled container, such as a pre-filled vial, cartouche, sachet, or ampoule.

EXAMPLES

Example 1. First-In-Human Study with SAR445088

SAR445088 is a humanized monoclonal antibody that selectively inhibits activated C1s and prevents the enzymatic action of C1 on its substrates C4 and C2, thus inhibiting the formation of the classical pathway C3 convertase, C4b2a. SAR445088 inhibits the downstream signaling cascade of the complement system that originates via the CP, while the alternative pathway (AP) and lectin pathways remain functional.

SAR445088 contains a serine-proline mutation (S241P) that stabilizes the core-hinge region of the molecule, a leucine-to-glutamic acid mutation (L248E) that abrogates Fcγ receptor binding, and methionine-to-leucine (M428L) and asparagine-to-serine (N434S) mutations that increase neonatal Fc receptor (FcRn) binding affinity and increase the half-life. The LC CDR1, LC CDR2, LC CDR3, HC CDR1, HC CDR2, HC CDR3, VH, VL, and heavy and light chain sequences of the SAR445088 are described elsewhere in the application as SEQ ID NOs. 1-10. The sequences are also described in U.S. Pat. Nos. 9,512,233, 10,729,767, and U.S. Patent Application Publication No. US 2020/0048332, each of which is herein incorporated by reference in its entirety.

In non-clinical studies, SAR445088 showed a graded inhibition-concentration relationship. This first-in-human (FIH) clinical trial investigated the safety, tolerability, pharmacokinetic (PK) and pharmacodynamic (PD) profiles of single intravenous (IV) and subcutaneous (SC) administration and multiple SC doses of SAR445088 in healthy participants.

METHODS

Study Design

This FIH trial was a single-center, double-blind, randomized, placebo-controlled, integrated single ascending dose (SAD; Part 1) and multiple ascending dose (MAD; Part 2) study of SAR445088 in healthy participants and included a Japanese cohort. In Part 1, nine dose cohorts (IV: 2, 4, 8, 16, 30, and 50 mg/kg; SC: 300, 600, and 1200 mg) of eight participants each were planned and randomized in a 3:1 ratio of SAR445088 (n=6) and matched placebo (n=2). For Part 2, three cohorts of 10 participants each were planned and randomized in a 4:1 ratio of SAR445088 (n=8) and matched placebo (n=2). Participants in Part 2 received 300 or 600 mg SC once weekly for 4 weeks or 600 mg SC once daily for 3 consecutive days of SAR445088 or placebo.

The study enrolled healthy male and female participants (age: 18-50 years, bodyweight: 45.0-110.0 kg, and body mass index: 18-32 kg/m 2). Vaccinations against encapsulated bacterial pathogens, such as meningococcus, were administered during the screening period to participants who had not received these vaccinations within 5 years prior to enrollment.

Study Objectives

The primary objective of the study was to assess the safety and tolerability of SAR445088 in healthy participants. Secondary objectives included the assessment of PK and PD profiles and immunogenicity.

Safety Assessments

Safety assessments included physical examination, clinical laboratory tests, serology tests (including SLE panel), urine analysis, vital signs, anti-drug antibodies (ADA), adverse events (AEs), and electrocardiograms (ECGs).

Bioanalytical Methods

Quantitation of SAR445088: A high-performance liquid chromatography assay with tandem mass spectrometry (MS/MS) detection was used to measure SAR445088 in plasma. An immunoaffinity approach was used to enrich SAR445088 from human plasma using magnetic beads coated with Protein G. The bound proteins were subject to on-bead proteolysis with trypsin, following standard protein denaturation, reduction, and alkylation processing steps. As a result of the trypsin digestion, characteristic peptide fragments originating as surrogates were used to determine the SAR445088 concentration. The lower limit of quantitation (LLOQ) was 10 μg/mL.

Wieslab CP assay: An enzyme-linked immunosorbent assay (ELISA) was used for the quantitative determination of complement activation in serum. The LLOQ was 10% activity.

Complement mediated hemolytic capacity (CH50) assay: CH50 was measured using an in vitro automated homogenous liposome-based assay (Fujifilm Wako) for the quantitative determination of total complement activity in human serum. The LLOQ for this assay was 10 IU/mL.

Estimation of anti-drug antibodies (ADA): An electrochemiluminescent immunoassay was used to evaluate the presence of ADA in plasma (PPD Laboratories, Richmond, VA).

Estimation of C4: C4 was quantitatively assessed using a commercially available in vitro diagnostic (Beckman Coulter, Brea, CA) assay kit at Gen X Laboratories Inc (Los Angeles, CA). The LLOQ for this assay was 8 mg/dL.

Wieslab alternate pathway (AP) assay: An ELISA assay was used for the qualitative determination of functional complement AP in human serum with an LLOQ of 10%.

Pharmacokinetic assessment: PK parameters were calculated by non-compartmental analysis. SAR445088 plasma concentrations and PK were summarized by descriptive statistics (such as mean, geometric mean, median, standard deviation [SD], standard error of mean (SEM), and coefficient of variation (CV), minimum and maximum) for each dose level and each route (IV and SC) using PKDMS (in-house software) version 3.1 with Phoenix WinNonLin Professional version 8.1. Data were also summarized by the ADA status as relevant. For each presentation, the mean concentration and PK parameter values are arithmetic means, unless specified. Concentration values below the plasma assay limit were treated as zero in calculating mean values. The below the limit of quantification (BLQ) data after the time to reach the maximum drug concentration ($t_{max}$) was treated as missing/omitted. The mean concentration values BLQ were reported as BLQ in tables and not plotted in the figures if after time to last observed concentration ($t_{last}$).

Population PK/PD modelling: The population PK analysis with data from both Part 1 and Part 2 was performed with nonlinear mixed effects modeling (NONMEM; version 7.4.1). Covariates including demographics (gender, age, weight, and race), ADA status, baseline complement factor C4, alanine aminotransferase (ALT), and aspartate transaminase (AST) were screened graphically. Selected covariates (ADA status, gender, age, weight, and race) were assessed statistically using stepwise forward selection/backward elimination steps. The relationship between SAR445088 exposure and PD response was examined. The impact of covariates (age, weight, sex, race, baseline CP, and CH50) was assessed statistically using stepwise forward selection/backward elimination. Covariates contributing at least a 6.63 unit change in the minimum value of the objective function (MVOF) (α=0.01, one degree of freedom) were considered statistically significant during the stepwise forward selection. The covariate contributing the most significant change in the MVOF (smallest p-value) was included in the new base covariate model. The new model was also evaluated for the decrease in the inter-individual variability (IIV) of the PK parameters. Highly correlated covariates were not included in a single covariate-parameter submodel. This process was repeated until there were no further covariates that produced significant changes in the MVOF. The resulting model was considered the full multivariable model. The appropriateness of structure and statistical models was assessed throughout and refined as necessary.

In the backward elimination of covariates, each covariate was removed from the parameter equation separately. A covariate was considered significant if it contributed to at least a 10.83 change in the MVOF value ($\alpha=0.001$, one degree of freedom) when removed from the model. The most non-significant covariate (the highest p-value >0.001) was removed from the model, and this reduced model then served as the new base multivariate model. The backward elimination procedure was repeated until all remaining covariates were statistically significant (p<0.001).

Statistical Analysis

Safety: Safety analysis (including AEs, laboratory parameters, vital signs, and ECGs) was based on the review of individual values and descriptive statistics. The treatment-emergent adverse event (TEAE) period was defined as the time from the first SAR445088 administration up to the end of study visit (included). AEs were coded according to the Medical Dictionary for Regulatory Activities version 23.0, and the severity was graded per the National Cancer Institute Common Terminology Criteria for Adverse Events, version 5.0. The number (%) of participants experiencing TEAEs were summarized by dose level group. Potentially clinically significant abnormalities in clinical laboratory test results, vital signs, and ECG were flagged and summarized by dose level group using frequency tables.

The SLE panel testing was assessed by summarizing the number (%) of participants with negative, positive, or marginal status data for each dose level group, parameter, and visit. The number of participants experiencing local injection site reactions (e.g., pain, tenderness, erythema, swelling/induration, or itching) was summarized by dose level group and grade (mild/moderate, severe, and very severe). The immunogenicity for SAR445088 was assessed by summarizing the number and the percentage of participants with ADA positive or negative status, by dose level group and visit. In the setting of a positive ADA, the absolute ADA concentration was summarized with descriptive statistics by dose level and visit.

Pharmacokinetics: SAR445088 PK parameters were summarized by dose level using descriptive statistics. Dose proportionality was assessed using a power model on maximum drug concentration in plasma ($C_{max}$), area under the curve from dosing to the time of the last measured concentration ($AUC_{last}$) or area under the curve from time 0 to 168 h ($AUC_{0-168}$) and AUC for each route (IV and SC). Accumulation was assessed using a linear model on the log-transformed accumulation ratio. Variance components of log-transformed $C_{max}$ and $AUC_{0-168}$ were estimated using a linear model.

Pharmacodynamics: The percent CP activity, percent AP activity, CH50, and C4 were analyzed in all participants. Descriptive statistics were provided by dose level and time of measurement.

Results

Participants' Demographics and Disposition

Overall, 93 healthy participants were enrolled in Part 1 and Part 2. In Part 1, a total of participants were enrolled. A single dose of SAR445088 or matching placebo was administered IV to a total of 45 participants, including 33 participants receiving SAR445088 and 12 participants receiving placebo. A single dose of SAR445088 or matching placebo was administered SC to a total of 20 participants, including 15 participants receiving SAR445088 and 5 participants receiving placebo. In the Japanese cohort, three participants received SC dose of SAR445088. All cohorts completed enrollment of eight participants (six SAR445088 and two placebo) as planned, except for the 50 mg/kg IV non-Japanese cohort and 300 mg SC Japanese cohort. Enrollment in these two cohorts was terminated early due to recruitment difficulties amidst the COVID-19 pandemic. One patient in 300 mg SC Japanese discontinued the study due to non-study-related reasons.

In Part 2, a total of 28 participants were enrolled and randomized to receive multiple doses of SAR445088. Twenty-two participants received SAR445088, and six participants received placebo. A subject on placebo withdrew from the study and discontinued study treatment due to a TEAE (decreased neutrophil count); this subject was not replaced. Enrollment for the 600 mg SC once daily×3 days cohort was terminated early due to recruitment difficulties amidst the COVID-19 pandemic. All enrolled participants in Parts 1 and 2 were included in the safety, PK, and PD analyses. A flow diagram of the patients' disposition is presented in FIG. 1. Demographic and baseline characteristics are provided in Tables 2-4.

TABLE 2

Summary of demographic characteristics of study population (Part 1, IV)
Part 1

| Parameters | Placebo (n = 12) | SAR445088 IV (n = 33) | | | | | | All (n = 45) |
| | | 2 mg/kg (n = 6) | 4 mg/kg (n = 6) | 8 mg/kg (n = 6) | 16 mg/kg (n = 6) | 30 mg/kg (n = 6) | 50 mg/kg (n = 3) | |
| --- | --- | --- | --- | --- | --- | --- | --- | --- |
| Age (years); mean (SD) | 30.9 (8.3) | 35.3 (3.9) | 31.0 (7.8) | 28.5 (10.1) | 34.0 (7.6) | 35.0 (7.6) | 29.3 (2.1) | 32.0 (7.5) |
| Female | 6 (50.0) | 1 (16.7) | 3 (50.0) | 1 (16.7) | 3 (50.0) | 3 (50.0) | 1 (33.3) | 18 (40.0) |
| Male | 6 (50.0) | 5 (83.3) | 3 (50.0) | 5 (83.3) | 3 (50.0) | 3 (50.0) | 2 (66.7) | 27 (60.0) |
| Race; n (%) | | | | | | | | |
| White | 7 (58.3) | 2 (33.3) | 2 (33.3) | 5 (83.3) | 4 (66.7) | 5 (83.3) | 1 (33.3) | 26 (57.8) |
| Black or African American | 2 (16.7) | 2 (33.3) | 3 (50.0) | 1 (16.7) | 1 (16.7) | 1 (16.7) | 1 (33.3) | 11 (24.4) |
| Asian | 2 (16.7) | 2 (33.3) | 0 | 0 | 0 | 0 | 0 | 4 (8.9) |

TABLE 2-continued

Summary of demographic characteristics of study population (Part 1, IV)
Part 1

| | SAR445088 IV (n = 33) | | | | | | | |
|---|---|---|---|---|---|---|---|---|
| Parameters | Placebo (n = 12) | 2 mg/kg (n = 6) | 4 mg/kg (n = 6) | 8 mg/kg (n = 6) | 16 mg/kg (n = 6) | 30 mg/kg (n = 6) | 50 mg/kg (n = 3) | All (n = 45) |
| Multiple | 1 (8.3) | 0 | 1 (16.7) | 0 | 1 (16.7) | 0 | 1 (33.3) | 4 (8.9) |
| Hispanic or Latino | 6 (50.0) | 0 | 1 (16.7) | 2 (33.3) | 1 (16.7) | 3 (50.0) | 0 | 13 (28.9) |
| Not Hispanic or Latino | 6 (50.0) | 6 (100) | 5 (83.3) | 4 (66.7) | 5 (83.3) | 3 (50.0) | 3 (100) | 32 (71.1) |
| Weight (kg); mean (SD) | 77.83 (10.80) | 83.32 (8.88) | 75.63 (11.98) | 82.07 (8.62) | 78.63 (13.89) | 78.93 (10.76) | 79.23 (21.42) | 79.18 (11.16) |
| BMI <30 | 10 (83.3) | 6 (100) | 6 (100) | 5 (83.3) | 5 (83.3) | 4 (66.7) | 3 (100) | 39 (86.7) |
| BMI ≥30 | 2 (16.7) | 0 | 0 | 1 (16.7) | 1 (16.7) | 2 (33.3) | 0 | 6 (13.3) |

Abbreviations: BMI, body mass index; IV, intravenous; n, number of participants treated in each group; n (%), number and percent of participants; SC, subcutaneous; SD, standard deviation

TABLE 3

Summary of demographic characteristics of study population (Part 1, SC)
Part 1

| | SAR445088 SC (n = 15) | | | | |
|---|---|---|---|---|---|
| Parameters | Placebo (n = 5) | 600 mg (n = 6) | 1200 mg (n = 6) | 300 mg Japanese (n = 3) | All (n = 20) |
| Age (years); mean (SD) | 36.4 (8.0) | 35.3 (4.0) | 41.7 (7.4) | 38.7 (9.9) | 38.0 (7.0) |
| Female | 2 (40.0) | 1 (16.7) | 5 (83.3) | 2 (66.7) | 10 (50.0) |
| Male | 3 (60.0) | 5 (83.3) | 1 (16.7) | 1 (33.3) | 10 (50.0) |
| Race; n (%) | | | | | |
| White | 2 (40.0) | 3 (50.0) | 3 (50.0) | 0 | 8 (40.0) |
| Black or African American | 2 (40.0) | 2 (33.3) | 3 (50.0) | 0 | 7 (35.0) |
| Asian | 1 (20.0) | 0 | 0 | 3 (100) | 4 (20.0) |
| Multiple | 0 | 1 (16.7) | 0 | 0 | 1 (5.0) |
| Hispanic or Latino | 1 (20.0) | 3 (50.0) | 0 | 0 | 4 (20.0) |
| Not Hispanic or Latino | 4 (80.0) | 3 (50.0) | 6 (100) | 3 (100) | 16 (80.0) |
| Weight (kg); mean (SD) | 78.38 (13.46) | 88.73 (9.07) | 68.95 (12.10) | 61.63 (13.76) | 76.15 (14.81) |
| BMI < 30 | 5 (100) | 4 (66.7) | 6 (100) | 3 (100) | 18 (90.0) |
| BMI ≥ 30 | 0 | 2 (33.3) | 0 | 0 | 2 (10.0) |

Abbreviations: BMI, body mass index; IV, intravenous; n, number of participants treated in each group; n (%), number and percent of participants; SC, subcutaneous; SD, standard deviation

TABLE 4

Summary of demographic characteristics of study population (Part 2)
Part 2

| | | SAR445088 SC (n = 15) | | | |
| Parameters | Placebo (n = 6) | 300 mg once weekly × 4 (n = 8) | 600 mg once weekly × 4 (n = 8) | 600 mg once daily × 3 (n = 6) | All (n = 28) |
| --- | --- | --- | --- | --- | --- |
| Age (years); mean (SD) | 35.3 (5.4) | 39.3 (7.8) | 34.1 (7.6) | 33.8 (8.1) | 35.8 (7.3) |
| Sex; n (%) | | | | | |
| Female | 1 (16.7) | 3 (37.5) | 2 (25.0) | 2 (33.3) | 8 (28.6) |
| Male | 5 (83.3) | 5 (62.5) | 6 (75.0) | 4 (66.7) | 20 (71.4) |
| Race; n (%) | | | | | |
| White | 5 (83.3) | 4 (50.0) | 5 (62.5) | 4 (66.7) | 18 (64.3) |
| Black or African American | 1 (16.7) | 1 (12.5) | 2 (25.0) | 0 | 4 (14.3) |
| Asian | 0 | 2 (25.0) | 1 (12.5) | 2 (33.3) | 5 (17.9) |
| Multiple | 0 | 1 (12.5) | 0 | 0 | 1 (3.6) |
| Ethnicity; n (%) | | | | | |
| Hispanic or Latino | 2 (33.3) | 4 (50.0) | 1 (12.5) | 1 (16.7) | 8 (28.6) |
| Not Hispanic or Latino | 4 (66.7) | 4 (50.0) | 7 (87.5) | 5 (83.3) | 20 (71.4) |
| Weight (kg); mean (SD) | 80.63 (8.41) | 71.98 (14.07) | 74.03 (9.45) | 80.92 (13.05) | 76.33 (11.62) |
| BMI (kg/m$^2$); n (%) | | | | | |
| BMI < 30 | 5 (83.3) | 8 (100) | 8 (100) | 5 (83.3) | 26 (92.9) |
| BMI ≥ 30 | 1 (16.7) | 0 | 0 | 1 (16.7) | 2 (7.1) |

Abbreviations: BMI, body mass index; IV, intravenous; n, number of participants treated in each group; n (%), number and percent of participants; SC, subcutaneous; SD, standard deviation Safety and Tolerability The 93 randomized healthy adult participants who received at least one dose of SAR445088 or matching placebo were included in the safety population. There were no deaths, severe TEAE, or treatment-emergent serious adverse event (TESAE) reported during the study.

Overall, there were no concerning trends observed in vital signs, ECGs, or laboratory values. No serious infections or meningococcal infections occurred.

Pharmacokinetics

Figures 2A, 2B:
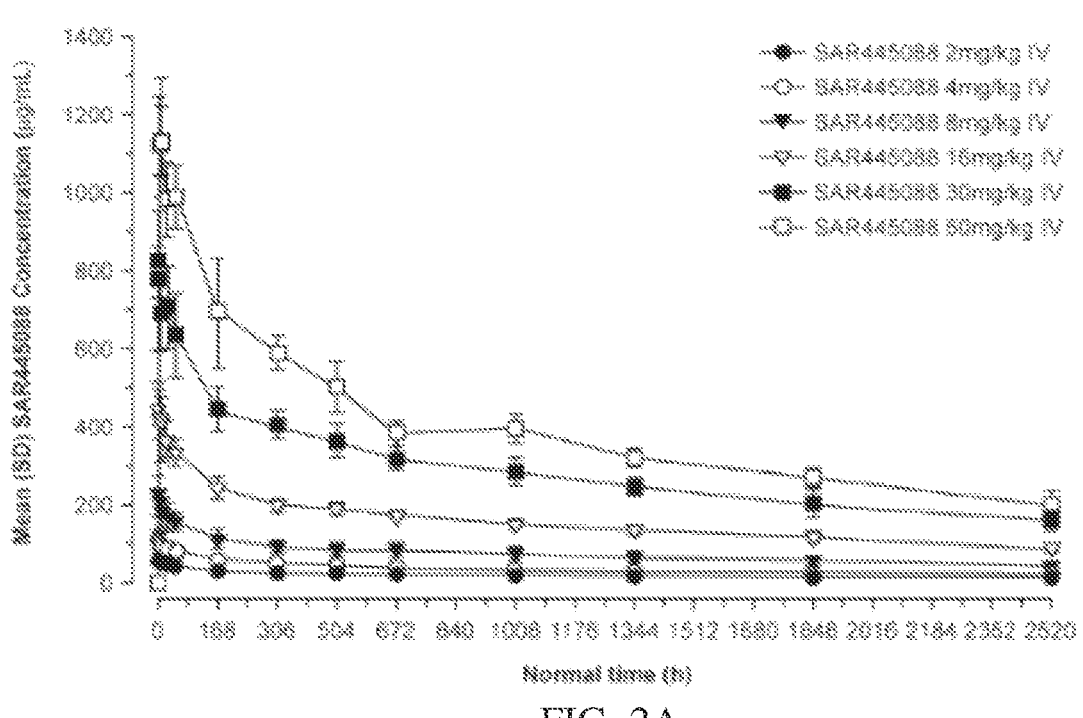
FIGS. 2A-2D show the pharmacokinetic (mean±SD) plasma concentration-time profiles (a) single-dose IV cohorts (mean±SD) in linear scales, (b) single-dose SC cohorts (mean±SD) in linear scales, (c) multiple-dose 300 mg or 600 mg SC after the last weekly dose, (d) multiple-dose 600 mg SC daily for three doses. IV, intravenous; h, hour; SC, subcutaneous; SD, standard deviation.
Figure 2C:
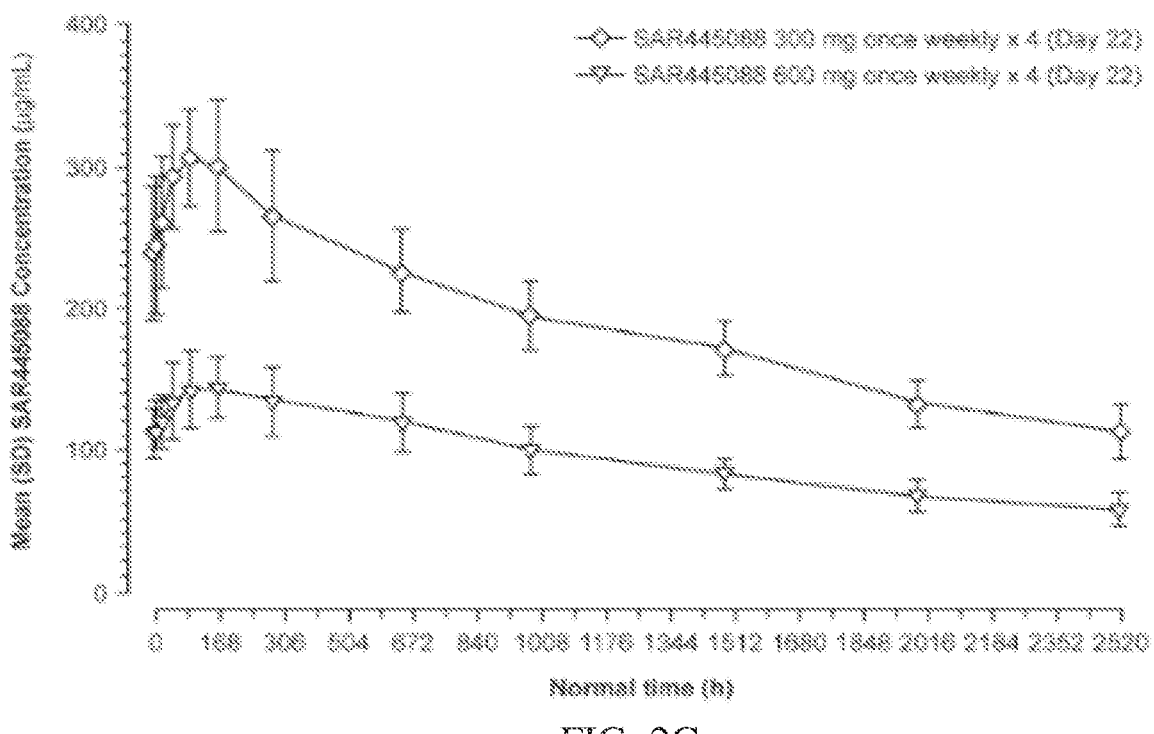
Figure 2D:
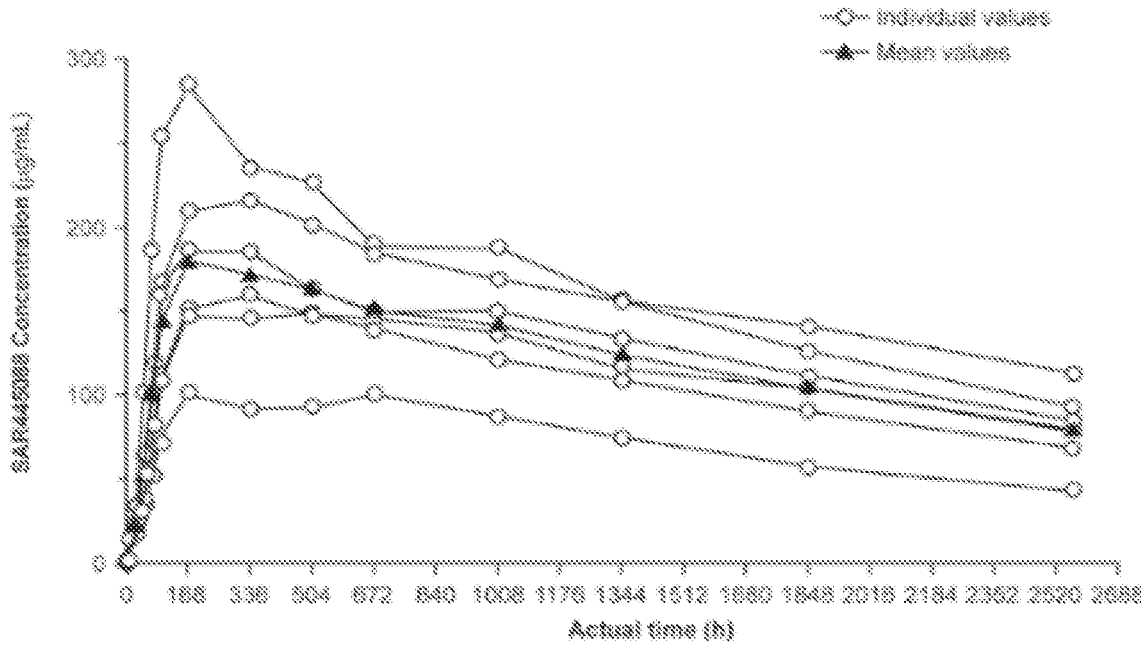

The mean (±SD) PK parameters after IV and SC doses and the corresponding plasma concentration-time profiles for Parts 1 and 2 are presented in Table 5 and FIG. 2, respectively.

TABLE 5

Summary of mean (±SD) PK parameters

| | | | | | | | | |
| Cohort[a] | n | $C_{max}$ (μg/mL) | $t_{max}$ (h)[b] | AUC (h × μg/mL)[c] | $AUC_{last}$ (h × μg/mL) | $t_{1/2z}$ (h) | CL (mL/h) | $V_dF$ (L) |
| --- | --- | --- | --- | --- | --- | --- | --- | --- |
| 2 mg/kg IV | 6 | 55.3 (9.39) | 1.65 (1.60-9.10) | 96,700 (15,900) | 48,800 (8640) | 2560 (946) | 1.75 (0.376) | 6.23 (1.63) |
| 4 mg/kg IV | 6 | 111 (23.2) | 1.60 (1.60-4.60) | 140,000 (66,600) | 86,800 (29,500) | 1610 (854) | 2.86 (2.13) | 4.91 (1.15) |
| 8 mg/kg IV | 6 | 229 (48.3) | 1.62 (1.60-4.63) | 322,000 (48,600) | 187,000 (34,200) | 2130 (398) | 2.08 (0.293) | 6.29 (1.04) |
| 16 mg/kg IV | 6 | 464 (74.3) | 1.63 (1.62-8.63) | 634,000 (78,500) | 389,000 (23,100) | 1890 (315) | 2.01 (0.471) | 5.36 (0.684) |
| 30 mg/kg IV | 6 | 819 (90.2) | 1.61 (1.53-1.63) | 1190,000 (255,000) | 718,000 (77,000) | 1970 (669) | 2.04 (0.375) | 5.61 (1.37) |
| 50 mg/kg IV | 3 | 1180 (127) | 4.68 (1.60-8.63) | 1390,000 (146,000) | 995,000 (89,500) | 1400 (60.1) | 2.82 (0.538) | 5.65 (0.869) |
| 600 mg SC | 6 | 82.5 (21.1) | 181 (167-337) | 198,000 (48,500) | 123,000 (22,900) | 1800 (316) | 3.19 (0.784)[d] | 8.03 (1.11)[e] |
| 1200 mg SC | 6 | 185 (27.0) | 131 (94.8-242) | 557,000 (139,000) | 310,000 (44,000) | 2050 (409) | 2.27 (0.583)[d] | 6.47 (0.604)[e] |

TABLE 5-continued

| Summary of mean (±SD) PK parameters | | | | | | | | |
|---|---|---|---|---|---|---|---|---|
| 300 mg SC (Japanese) | 3 | 51.2 (11.0) | 171 (169-506) | 138,000 (60,400) | 72,200 (40,800) | 1630 (470) | 2.42 (0.852)[d] | 5.32 (0.741)[e] |

| Part 2 | | | | | | | | |
|---|---|---|---|---|---|---|---|---|
| Cohort | n | First dose $C_{min}$ (µg/mL) | Last dose $C_{min}$ (µg/mL) | $t_{max}$ (h)[f] | $t_{1/2z}$ (h) | Day 1 $AUC_{0-168}$ (µg × h/mL) | Day 22 $AUC_{0-168}$ (µg × h/mL) | Accumulation ratio[g] |
| 300 mg SC once weekly × 4 | 8 | 37.8 (7.40) | 144 (22.5) | 96.0 (48.1 to 168) | 1800 (378) | 4460 (1760) | 22,800 (4000) | 5.50 (1.54)[g] |
| 600 mg SC once weekly × 4 | 8 | 83.4 (14.4) | 301 (47.0) | 96.4 (48.0 to 97.6) | 1690 (588) | 10,900 (2060) | 49,000 (6200) | 4.61 (0.563)[g] |
| 600 mg SC once daily × 3 | 6 | 22.5 (8.42) | 102 (57.1) | 119 (117 to 122) | 1950 (460) | — | — | — |

Abbreviations: AUC, area under the curve; $AUC_{0-168}$, area under the curve from time 0 to 168 h; $AUC_{last}$, AUC from dosing to the time of the last measured concentration; CL, volume of plasma cleared of analyte per unit of time; CL/F; $C_{max}$, maximum drug concentration in plasma; $C_{min}$, minimum drug concentration in plasma; IV, intravenous; n, number participants; PK, pharmacokinetics; SC, subcutaneous; SD, standard deviation; $t_{1/2z}$, terminal-phase elimination half-life; $t_{max}$, time to reach maximum drug concentration; $V_dF$, apparent volume of distribution
[a]For IV cohorts, the median infusion time was 0.6 h and the first post-dose sample was collected 1 h after the end of infusion.
[b]Presented as median (range).
[c]Extrapolation ratios ranged from 28.3% to 48.9%, estimated parameters (AUC, CL, CL/F, $V_z$, and $V_z$/F) should be interpreted with caution.
[d]Apparent clearance (CL/F) after a subcutaneous dose was estimated.
[e]Apparent volume of distribution ($V_d$/F) after a subcutaneous dose was estimated.
[f]$t_{max}$ estimated after the last dose: median (min, max).
[g]Weekly dosing accumulation ratio calculated as Ratio Day 22 $AUC_{0-168 \ h}$/Day 1 $AUC_{0-168 \ h}$.

The bioavailability range of SAR445088 after an SC dose was 67.5% to 92.0%. After a single IV or SC dose of SAR445088, exposure increased in a dose-proportional manner over the entire range of 2 to 50 mg/kg IV or 600 to 1200 mg SC. After a single SC dose, the PK profile of SAR445088 was described by slow absorption (3.95-21.1 days). A long half-life (cohort mean: 8-15 weeks) after IV or SC administration was observed.

Figure 3A:
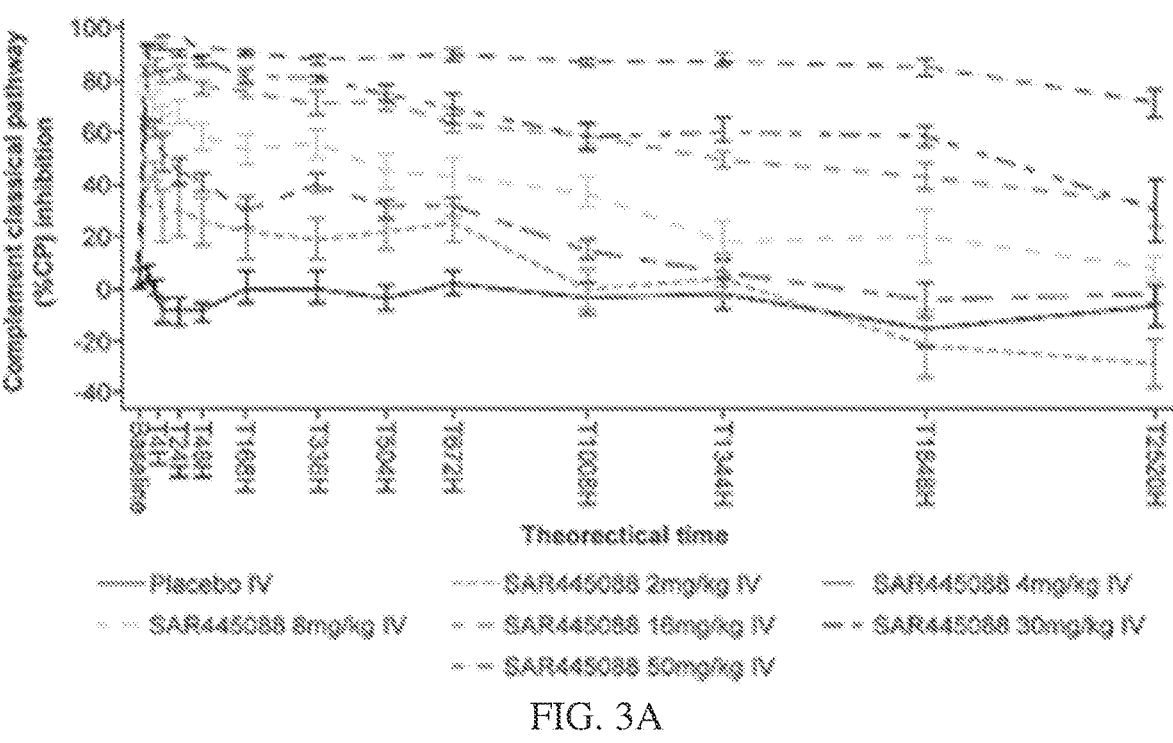
FIGS. 3A-3F show the pharmacodynamic effect on complement classical pathway and CH50 (Part 1 and Part 2). (a) Percentage CP inhibition—time profile plots after single IV dose. (b) Percentage CP inhibition—time profile plots after single SC dose. (c) Percentage CP inhibition—time profile plots after repeated SC doses. (d) CH50—time profile plots after single IV dose. (e) CH50—time profile plots after single SC dose. (f) CH50—time profile plots after repeated SC doses. CP, classical complement pathway; CH50, 50% hemolytic complement activity; IV, intravenous; SC, subcutaneous; SEM, standard error of mean.
Figure 3B:
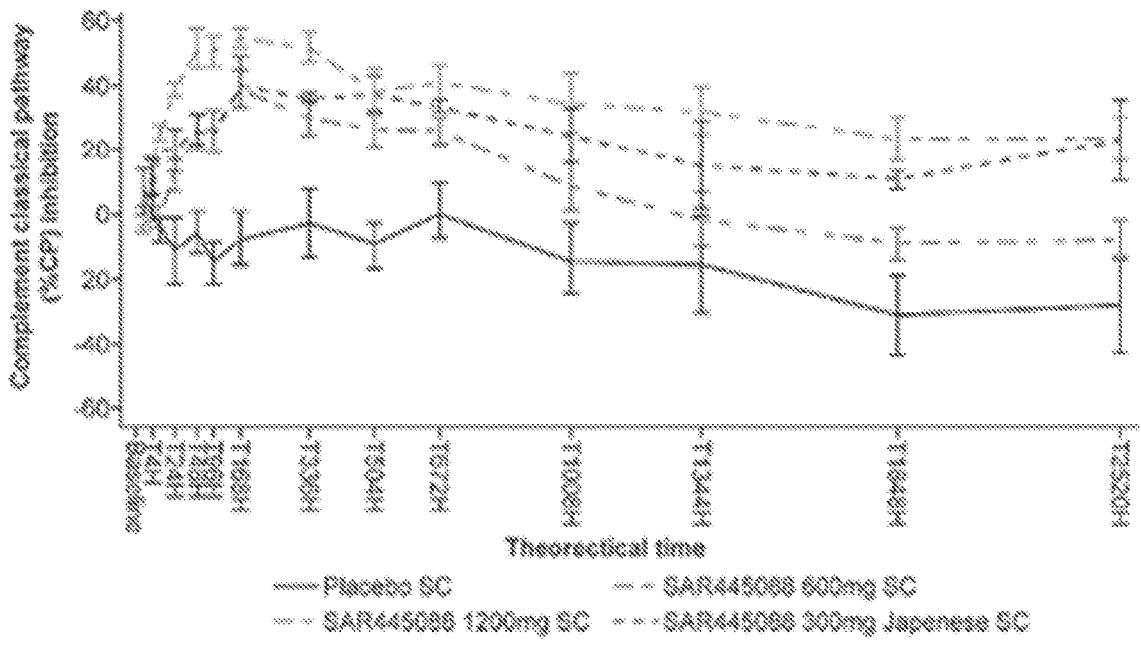
Figure 3C:
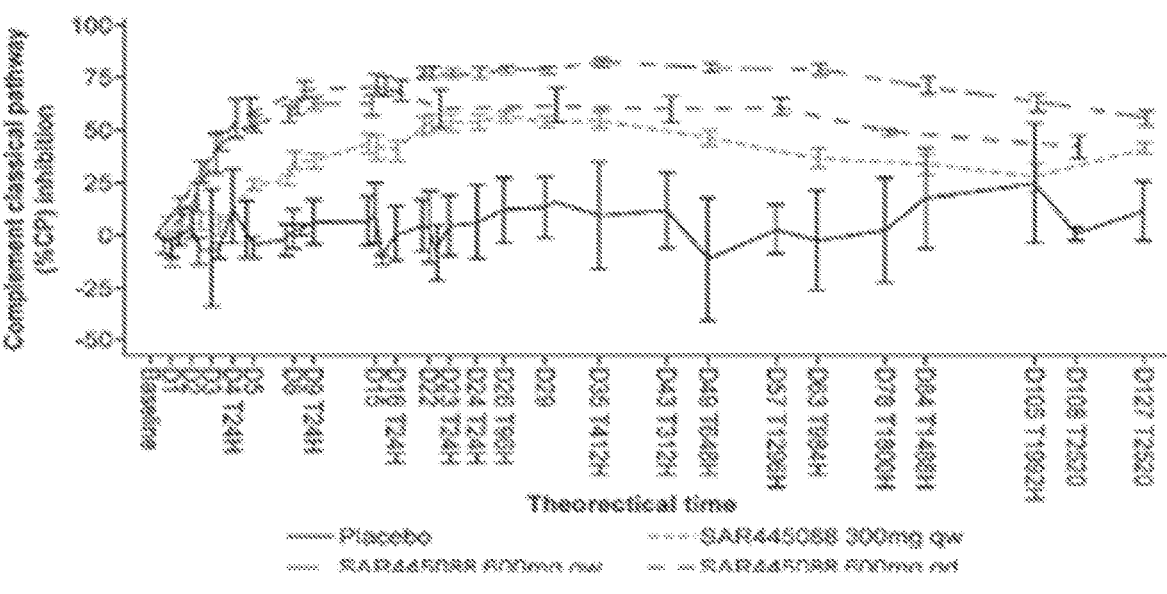

Treatment-related ADAs were observed in two participants in Part 1 (one subject each after 2 mg/kg IV and 600 mg SC) and in two participants in Part 2 (300 mg SC group) with no apparent impact on SAR445088 exposure.
Pharmacodynamics Percent CP activity: Dose-dependent inhibition of percent CP activity, analyzed as change from the pre-dose level, was observed after single or multiple doses of SAR445088 (FIGS. 3A-3C). In Part 1, the maximum inhibition of percent CP activity from baseline was >90% on Day 1 after a single 30 or 50 mg/kg IV dose and 55% on Day 7 after a single 1200 mg SC dose. The extent and duration of inhibition of percent CP activity after a single IV or SC dose appeared to be dose dependent. The maximum inhibition of percent CP activity of >90% was sustained for approximately 4 weeks after administration of 50 mg/kg IV. In Part 2, the maximum inhibition of percent CP activity from baseline was 82% on Day 35 after the fourth weekly 600 mg SC dose, and the inhibition of percent CP activity was sustained over the duration of the study period. After three daily 600 mg SC doses, the maximum inhibition of percent CP activity from baseline was 70.5% on Day 15 and declined thereafter.

Figure 3D:
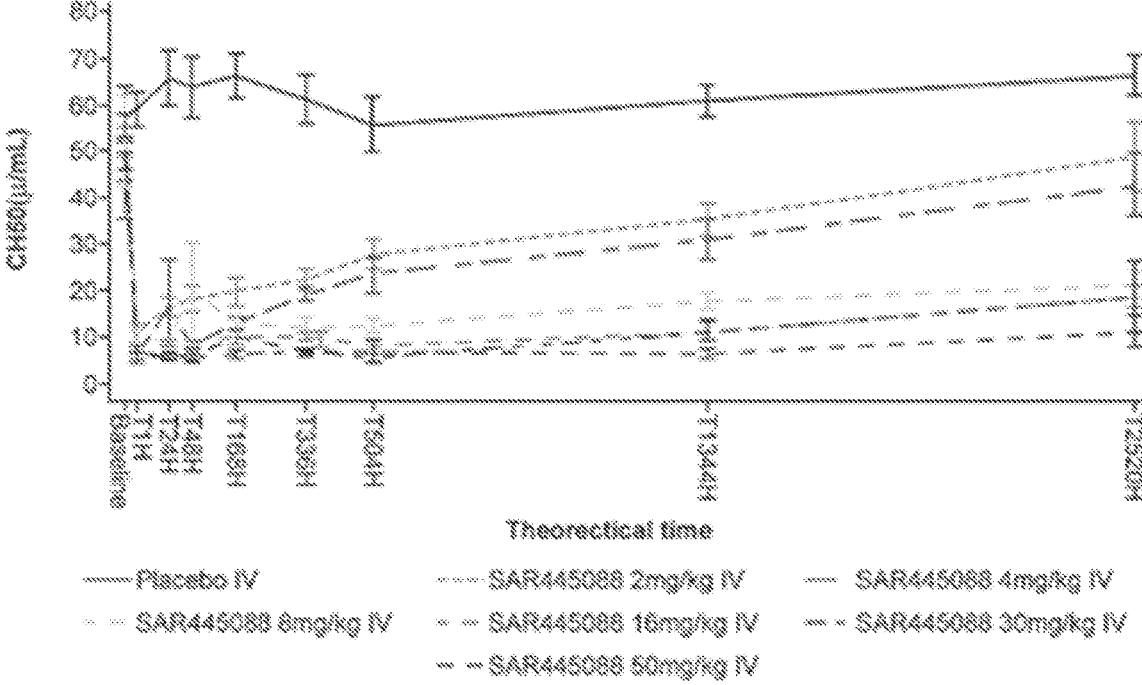
Figure 3E:
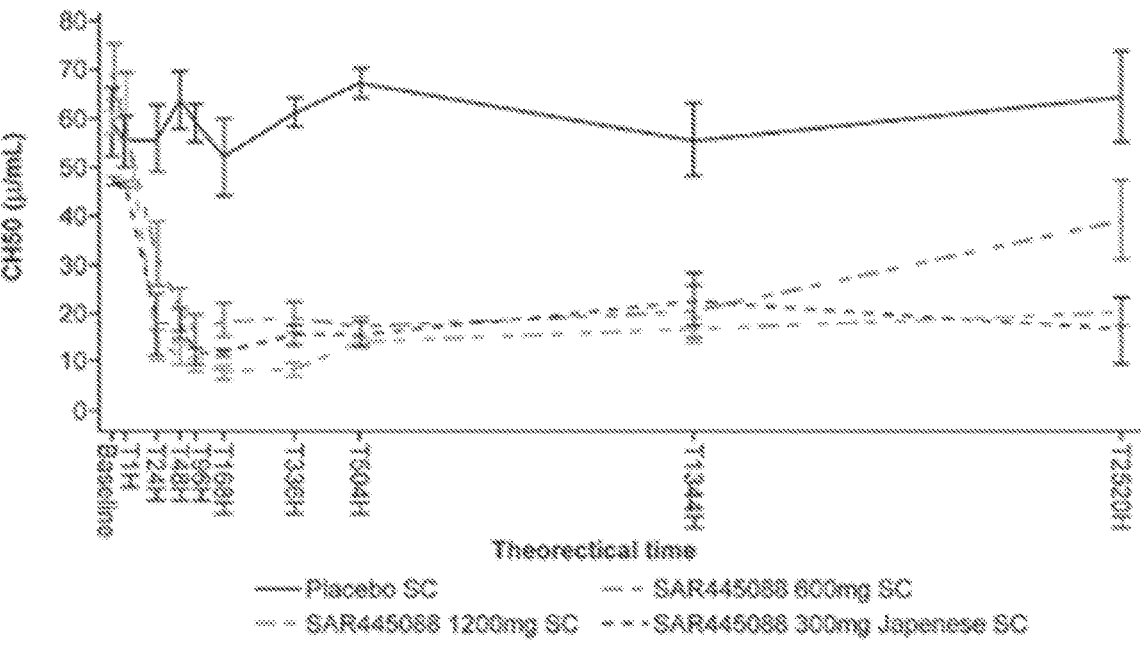
Figure 3F:
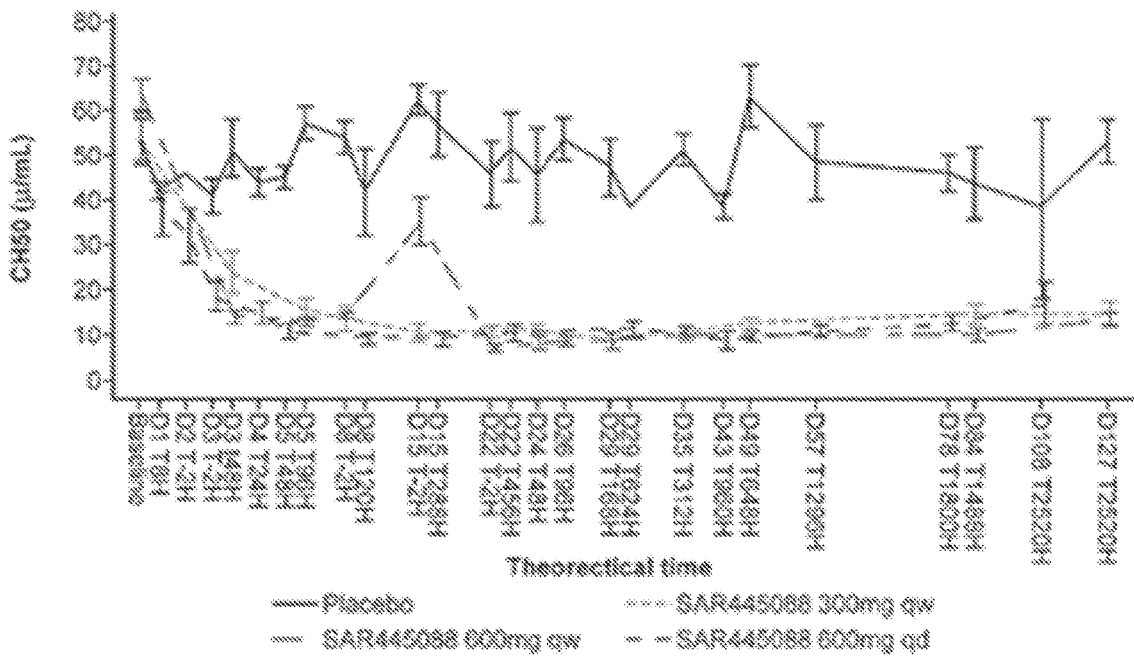
Figure 4A:
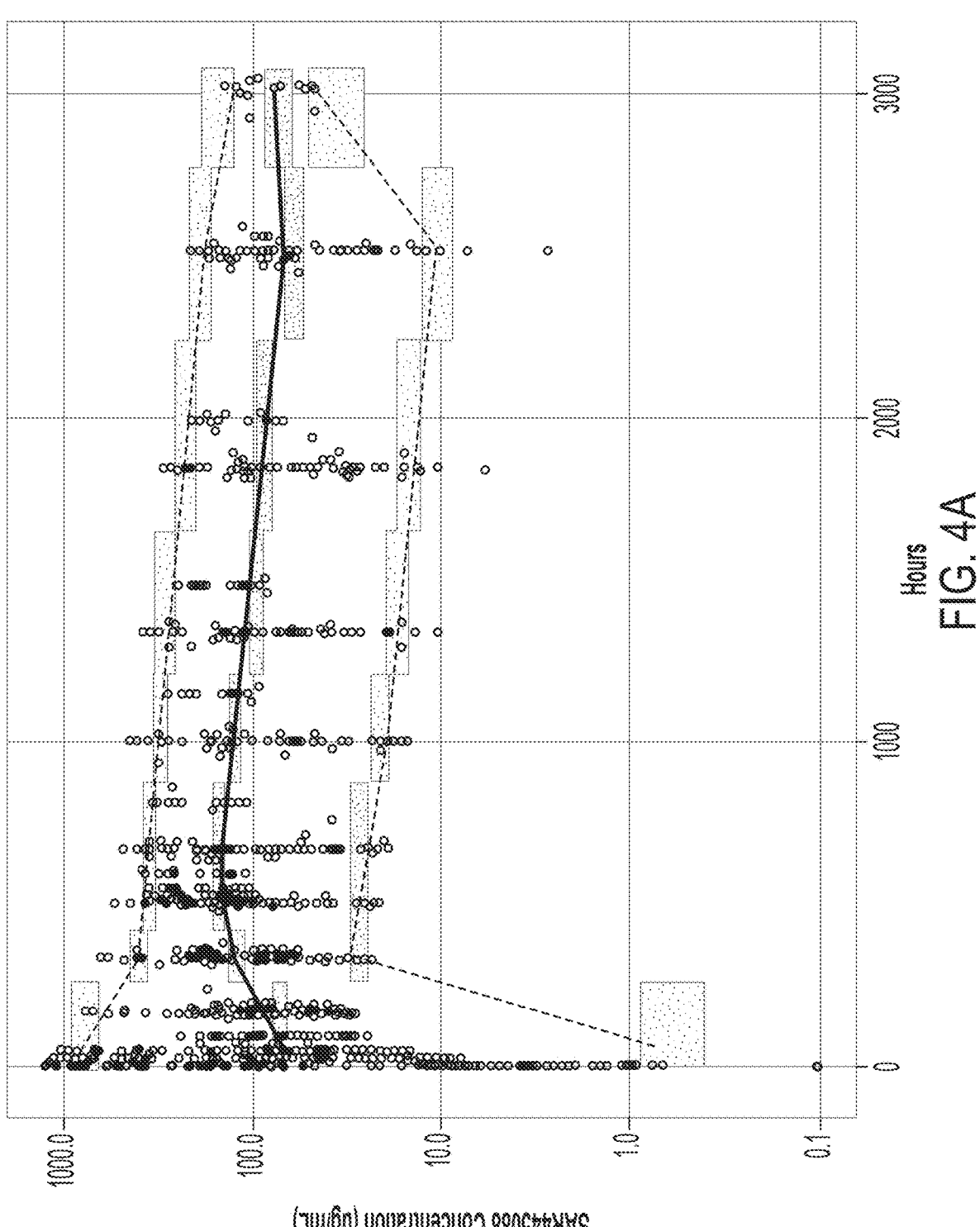
FIGS. 4A-4E show the pharmacokinetic/pharmacodynamic correlation: percent CP, CH50, percent AP and C4 profiles. (a) Visual predictive checks for the final healthy subject population PK model. Note: Legend: blue dots: observations; solid and red dashed lines: the median and bounds (5th and 95th percentiles) of observed concentrations at each time bin; pink and light blue areas: confidence intervals of median and centiles of predicted concentrations at each time bin. X-axis is time after administration of first dose. (b) CH50 vs SAR445088 (single dose) concentration for IV cohorts. (c) CH50 vs SAR445088 (single dose) concentration profile for SC dose. (d) % CP inhibition vs SAR445088 (single dose) concentration for IV cohorts. (e) % CP inhibition vs SAR445088 (single dose) concentration for SC dose. AP, alternate pathway; CH50, 50% hemolytic complement activity; CP, classical complement pathway; IV, intravenous; SC, subcutaneous.
Figure 4B:
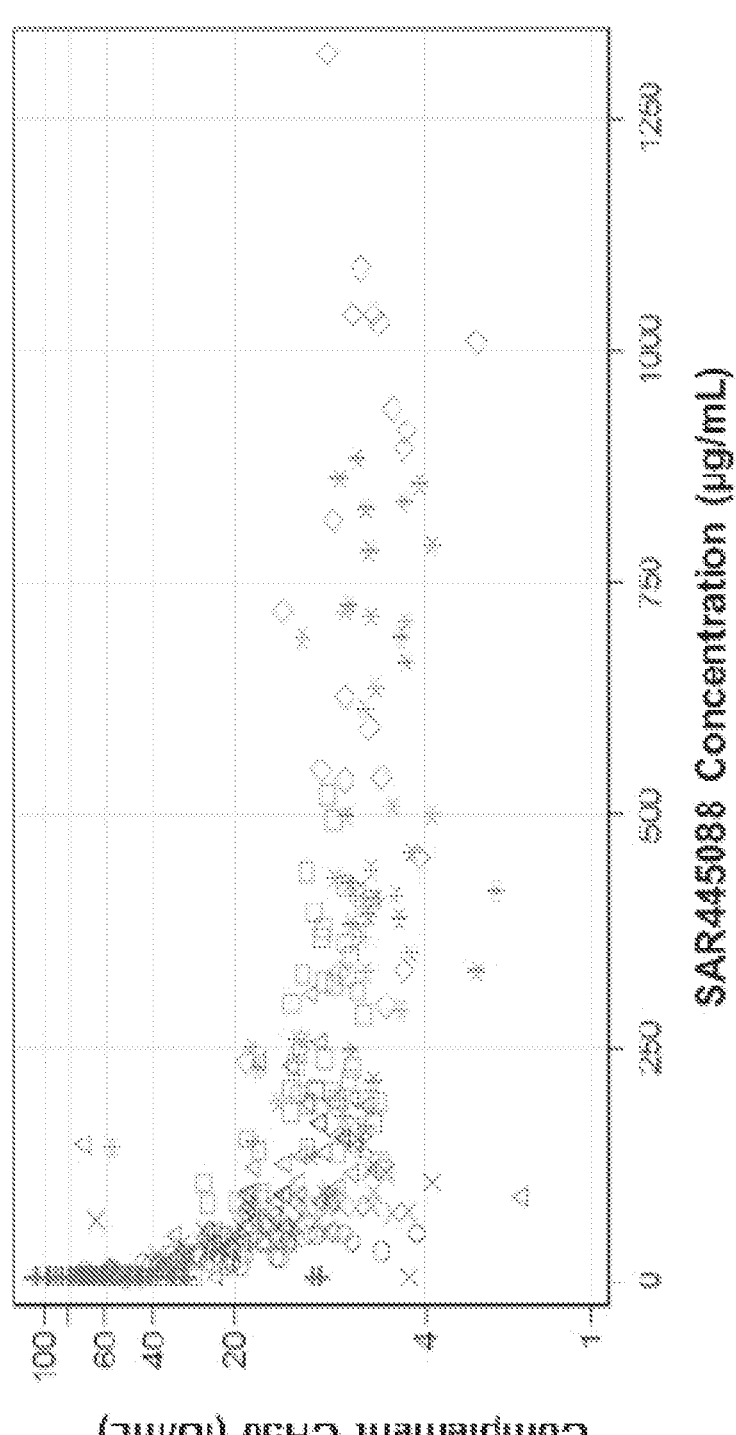
Figure 4C:
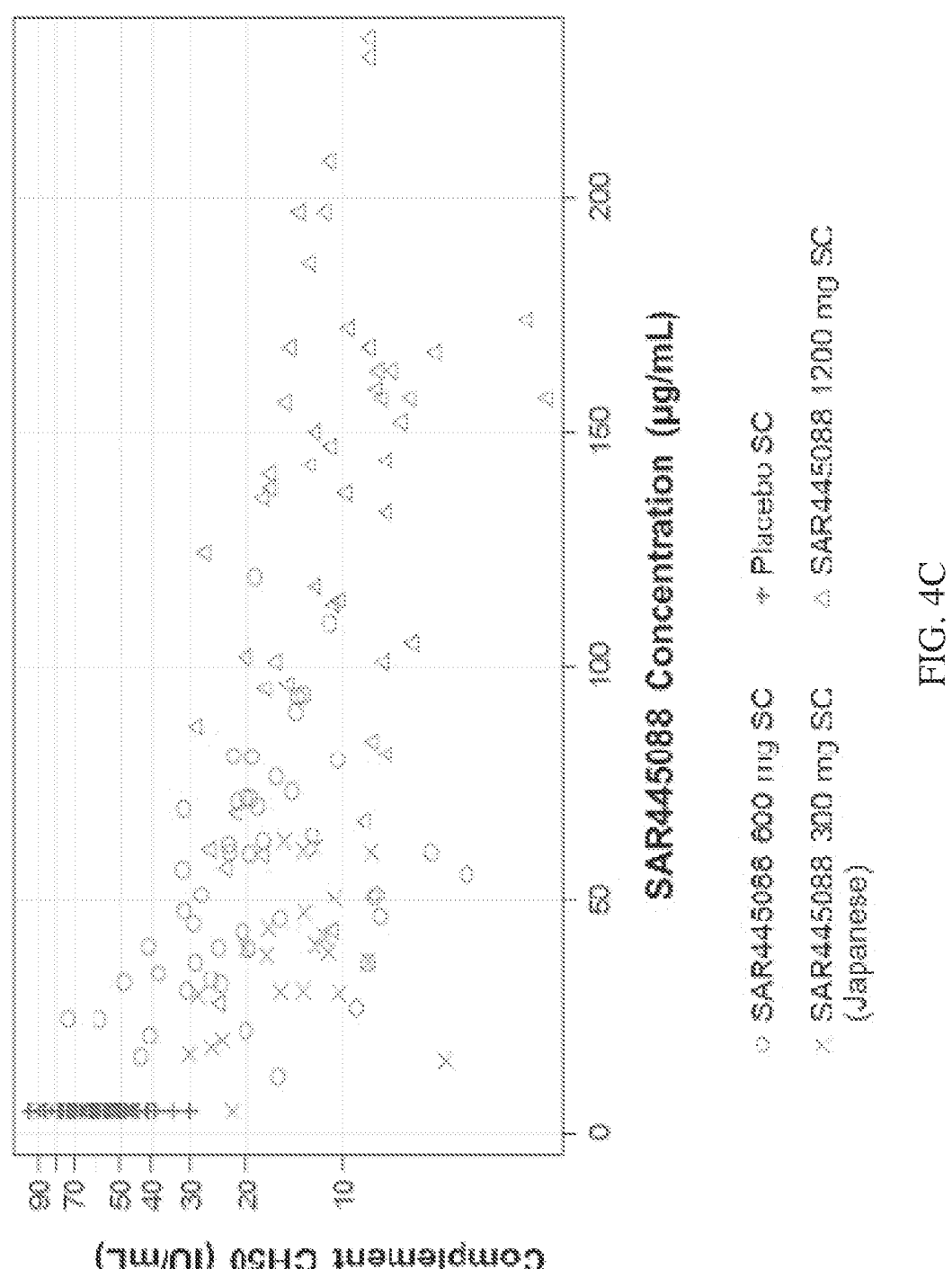
Figure 4D:
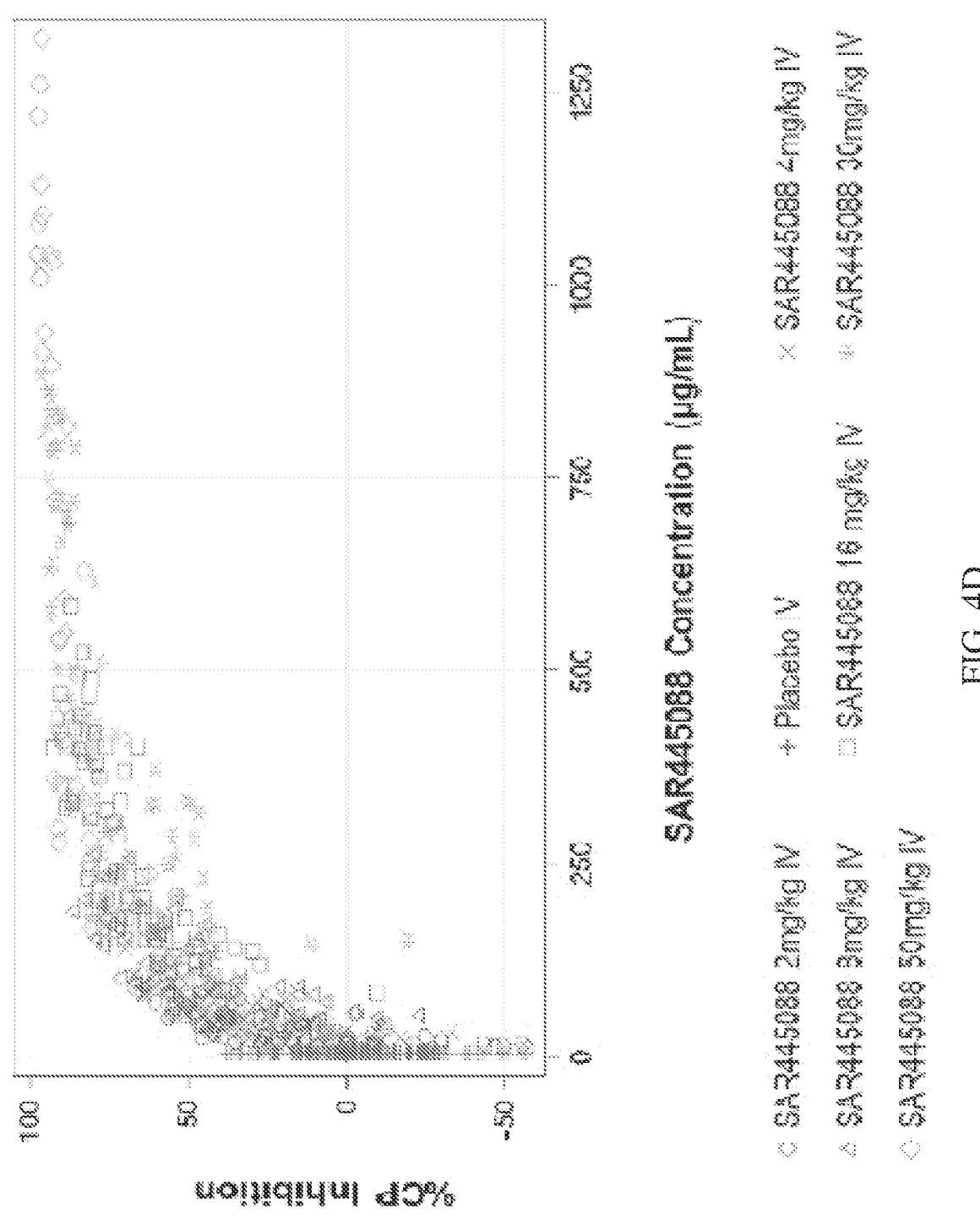
Figure 4E:
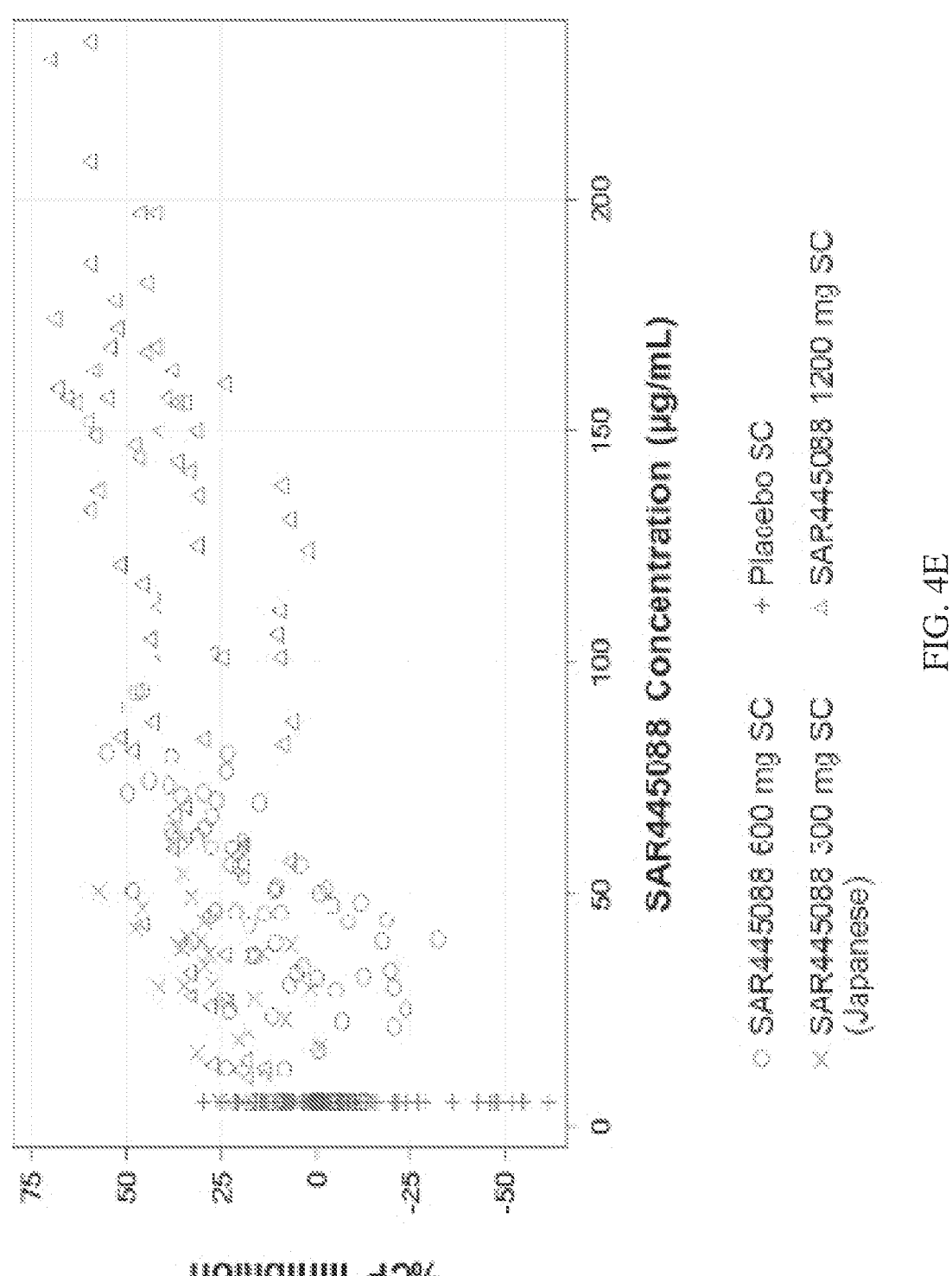

CH50 inhibition: Dose-dependent inhibition of CH50 was observed after single or multiple doses of SAR445088 (FIGS. 3D-3F). In Part 1, a sustained reduction in CH50 (≤10 IU/mL) was observed with the 16 mg/kg IV dose within 1 h and was sustained at this level until week 3. A longer sustained reduction in CH50 to <10 IU/mL was observed with administration of 30 mg/kg IV (>3 weeks) or 50 mg/kg IV (>8 weeks). After a single 1200 mg SC dose, a reduction in CH50 (≤10 U/mL) was observed on Day 5, which was sustained until Day 15. In Part 2, a reduction in CH50 (≤10 U/mL) was observed in the 600 mg SC weekly cohort on Day 22, which was sustained at this level until Day 84. Daily administration of 600 mg SC for 3 days resulted in a reduction of CH50 to ≤10 IU/mL on Day 8, which was sustained until Day 22. Percent AP activities did not change after a single IV or SC dose and were similar to baseline levels throughout the study period for all participants. C4 is the first complement component in the CP cleaved by activated C1s. Total C4 levels did not change after single or multiple doses and were similar to baseline levels throughout the study period in all study participants. Without wishing to be bound by theory, this was likely due to the fact that the study was conducted in healthy participants who only have low-level activation of C1s.
Population PK/PD Modeling Population PK modeling: A total of 70 participants (who received SAR445088) with 1244 concentration records were used for the model development. The population PK of SAR445088 was characterized by a two-compartment model with the first-order absorption and linear elimination. Typical clearance was 2.12 mL/h. The total volume of distribution ($V_d$) (5.45 L) was consistent with plasma volume, and drug distribution was confined to blood circulation. Model estimated bioavailability after SC administration was 75.4%. Population PK parameters were estimated with good precision with a relative standard error (RSE) of ≤30%. The magnitudes of estimated IIV were modest (36.6% CV to 75.0% CV). The results of the visual predicted checks (VPC) showed that the majority of the observed concentrations were within the prediction range (5th-95th percentiles). Among the tested covariates, bodyweight on the volume of the peripheral compartment ($V_2$) was retained as a statistically significant covariate. The peripheral $V_d$ increased 2.3-fold as the bodyweight increased from 50.4 kg (minimum) to 100.8 kg (maximum) (FIG. 4A).

Exposure-response relationship: A total of 93 participants (receiving SAR443088 or placebo) with 1496 CP and 963 CH50 records were used for developing the PK/PD model. The base CP PK/PD model was a direct response model with a nonlinear source of variability. The baseline CP activity was identified as a primary source of SAR445088 CP population pharmacokinetic-pharmacodynamic (PopPK/PD) variability. The observed CP baseline range was 66.2% to 186%, while the modeled base CP range was 75.3% to 139%. The VPC showed that the majority of the observed concentrations were within the prediction range ($5^{th}$-$95^{th}$ percentiles). For percent CP, the typical $IC_{50}$ was 96.4 µg/mL and the typical $IC_{90}$ was 458 µg/mL. The base CH50 PK/PD model was a direct response model with a nonlinear PD effect (FIGS. 4B-4E). No covariate was identified for the CH50 population PK/PD model that met the prespecified criteria for inclusion. The results of the VPC demonstrated that the majority of observed concentrations were within the prediction range ($5^{th}$-$95^{th}$ percentiles). For CH50, the typical $IC_{50}$ was 16.6 µg/mL, and the typical $IC_{90}$ was 57.0 µg/mL.

Using the final CP model, the concentration-time profiles of SAR445088 were simulated for a patient population (n=200) with bodyweight of 70 kg for a proposed therapeutic regimen (50 mg/kg IV load and 600 mg SC weekly maintenance). The proposed therapeutic regimen achieved inhibition of the CP (based on the Wieslab CP assay PK/PD relationship) after the first dose and maintained this inhibition throughout the treatment duration.

DISCUSSION

In this FIH trial in healthy participants, single or multiple doses up to 50 mg/kg IV of SAR445088 were well tolerated, and no safety concerns were observed. All reported TEAEs were of mild or moderate severity. No deaths, serious AEs, serious infection, infections with encapsulated bacteria, or meningitis were reported in this study. The risk of infection with encapsulated bacteria as a result of SAR445088 administration may be lower than with other complement inhibitors since SAR445088 leaves the alternative and lectin pathways of complement intact. Vaccination for encapsulated bacteria, such as meningococcus, was required in this study to mitigate this risk. Based on data from the participants with congenital CP deficiencies, a theoretical risk of inhibition of C1s is the development of SLE. In this study, no AEs concerning for the development of SLE were reported.

The PK of SAR445088 in healthy participants was notable for a long elimination half-life after IV or SC administration, which is partly due to methionine-to-leucine (M428L) and asparagine-to-serine (N434S) mutations that increase neonatal Fc receptor (FcRn) binding affinity at pH 6.0. In addition, SAR445088 binds only to activated C1s. target-mediated drug disposition Target-mediated drug disposition (TMDD) was not observed at the dose levels studied. Good bioavailability after SC dosing was also observed, which offers the potential of self-administration at home in chronic diseases requiring maintenance therapy. An approximate dose-proportional increase in SAR445088 exposure was observed over the evaluated dose ranges.

The incidence of treatment-induced ADA was low with no apparent impact on SAR445088 exposure, PK parameters or safety profile of SAR445088.

Complement inhibition was measured using two distinct assays, the Wieslab CP and CH50 hemolysis assays. With each assay, dose-dependent inhibition of the CP that reached levels observed among individuals with inborn or acquired classical complement deficiency was observed. Also, while comparing the Wieslab CP and CH50 hemolysis assays, approximately 8-fold difference in $IC_{50}$ values was observed, with higher drug exposures required to achieve the same level of CP inhibition with the Wieslab CP assay than with the CH50 hemolysis assay. This was possibly due to differences in the sample assay dilutions and readouts in the CH50 and Wieslab CP assays. Notably, in vitro studies using SAR445088 in patient blood samples also produced similar discrepancies between percent CP and CH50.

CONCLUSION

In this FIH trial in healthy adults, SAR445088 was well tolerated, and no serious or severe adverse events occurred. SAR445088 showed dose-dependent inhibition of the classical CP after a single IV or SC and multiple weekly or daily SC ascending doses in healthy participants.

Example 2. A Multicenter, Phase 1b, Open Label, Nonrandomized, Single Dose Study Evaluating the Safety, Tolerability and Activity of SAR445088 in Adults with Cold Agglutinin Disease Rationale The purpose of this Phase 1b study was to determine the safety, tolerability, activity, and PK of IV administration of a single dose of SAR445088 in an adult population of patients with cold agglutinin disease (CAD). By testing the effects of SAR445088 in CAD, this study aimed to detect biomarker evidence of improvement in hemolysis to support proof of concept for SAR445088.

Methodology

This was a multicenter, Phase 1b, open-label, nonrandomized study evaluating the safety and tolerability of a single IV dose of SAR445088 in adult participants with cold agglutinin disease (CAD).

The study was designed to assess the impact of SAR445088 on complement classical pathway-mediated hemolysis in CAD, and to generate data to determine doses for future studies. The study design included up to three single-dose IV cohorts. The study began dosing in Cohort 1a at a dose of 30 mg/kg IV, and on-study decisions about selection of the dose for the next cohort and/or expansion within a cohort were made based on clinical response (total bilirubin and hemoglobin) and variability of response across participants. Following Cohort 1a, a higher dose cohort (Cohort 1b) or lower dose cohort (Cohort 1c) could be enrolled. Cohort 1b was not enrolled while Cohort 1c at a dose of 15 mg/kg IV was enrolled.

Number of Participants

Planned: Approximately 6 participants were to be dosed in any IV cohort.

Treated: Twelve adult participants were treated with a single IV dose of SAR445088. Six participants received 30 mg/kg IV, and 6 participants received 15 mg/kg IV.

All 12 treated participants were included in all analysis populations (safety, pharmacodynamics, pharmacokinetics, ADA, BA, PK/PD, and PK/BA)

Diagnosis and Main Criteria for Inclusion and Exclusion:

Male and female participants aged 18 years and older with CAD, with a hemoglobin level ≤11 mg/dL at the time of screening.

i) have been previously vaccinated against encapsulated organisms ii) have not received systemic corticosteroids (in excess of 10 mg/prednisone or its equivalent per day), systemic immunosuppressants, systemic cytotoxic agents, specific complement system inhibitors other than SAR445088, or anti-CD20 therapy within three months prior to screening iii) have not received any biologics (antibody or its derivatives) within 4 months prior to screening.

Duration of Study Intervention

The total study duration for each participant was approximately 23 weeks:

Screening: up to 56 days, minimum of 14 days (Day −56 to Day −1).

Treatment: 1 day (Day 1); and,

Follow-up and End of Study: 105 days after SAR445088 administration (follow up visits from Day 2 to Day 71; End of Study visit on Day 106).

The study was considered completed for each participant when the participant completed all the scheduled study procedures.

Statistical Methods

Safety:

Safety analysis (AE, laboratory parameters, vital signs, ECGs) was based on the review of individual values, and descriptive statistics, and focused on the TEAE period that was defined as the time from the first IMP administration up to the end of study visit (included). All safety analyses were performed using the safety population by dose level cohort.

Adverse events were coded according to the Medical Dictionary for Regulatory Activities (MedDRA Version 24.1). Their severity was graded according to NCI-CTCAE v5.0. The number (%) of participants experiencing TEAEs was summarized by dose level cohort. Potentially clinically significant abnormalities (PCSAs) in clinical laboratory test results, vital signs, and ECG were flagged and summarized by dose level cohort using frequency tables. The SLE panel testing was assessed by summarizing the number (%) of participants with negative, positive or marginal status data for each dose level cohort, parameter and visit. Quantitative SLE parameters were summarized using descriptive statistics (N, mean, SD, SEM, median, min and max) and were provided by dose level cohort and time of measurement. The number of participants experiencing local injection site reactions (pain, tenderness, erythema, swelling/induration or itching) was summarized by dose level cohort and grade (mild/moderate, severe and very severe).

Anti-SAR445088 Antibodies (ADA):

Anti-SAR445088 antibodies (anti-drug antibodies, ADAs): the immunogenicity for SAR445088 was assessed by evaluating participants' ADA positive or negative status and summarizing by dose level cohort and visit, using ADA population. In addition, if ADA status was confirmed, absolute ADA concentration was summarized in descriptive statistics by dose level cohort and visit.

Pharmacokinetics (PK):

SAR445088 concentrations calculated in plasma were summarized by dose level cohort using descriptive statistics. In addition, a summary plot on raw data (mean+/−SD) was provided, one curve per dose level cohort. The population PK model developed in healthy subjects was evaluated in CAD patients by statistically evaluating model-predicted versus observed SAR445088 concentrations for each participant.

Pharmacodynamics (PD):

All PD analyses were performed by dose level cohort using the PD population. Quantitative parameters percent CP activity, percent AP activity, CH50, and total C4 were analyzed as raw data, change from baseline, and percent normalized to baseline for all participants included in the PD population. Percent CP inhibition was analyzed as raw data. Descriptive statistics on raw data, change from baseline, and percent normalized to baseline for percent CP activity, CH50, and total C4 were provided by dose level cohort and time of measurement. Time profile plots (mean±standard error of mean [SEM]) as well as change from baseline for each dose level cohort were provided for all PD parameters (percent CP activity, percent CP inhibition, CH50, and total C4).

Biomarker Activity (BA)

Hematologic BA were analyzed as raw data and change from baseline in all participants included in the BA population. Time profile plots (mean±standard deviation [SD]) for each dose level cohort were provided for all BA parameters as well as change from baseline.

PK/PD and PK/BA

The relationship between PD and BA variables and SAR445088 plasma concentrations was explored graphically using the PK/PD population and PK/BA population. Plot of mean (±SEM) change from baseline in PD and BA data and mean SAR445088 plasma concentration versus time (hours post-dose) overlaid onto the same plot. Scatter plots of PK SAR445088 concentrations versus PD raw data and change from baseline were provided over time.

SUMMARY OF RESULTS AND CONCLUSIONS

A total of 12 participants received a single dose of SAR445088 by IV administration.

Demographic and Other Baseline Characteristics:

The age range of study participants was 54 to 80 years (mean 67.4; median 69.0). The study included 1 male and 11 female participants.

Exposure:

The study began with 3 participants receiving a single dose of 30 mg/kg IV in Cohort 1a. After dosing, 2 of the 3 participants were found to have a bilirubin within the normal range at baseline, even though their bilirubin was above the ULN during screening. A decision was therefore made to enroll an additional 3 participants at a dose of 30 mg/kg. A normalization of bilirubin levels by Day 8 was seen in the 4 participants in Cohort 1a who had bilirubin levels above the ULN at baseline. The decision was therefore made to proceed to Cohort 1c at a dose of 15 mg/kg.

Overall, 6 participants received a single dose of SAR445088 30 mg/kg IV, and 6 participants received a single dose of SAR445088 15 mg/kg IV.

Safety Results:

There were no treatment-emergent SAEs, TEAEs leading to death, or TEAEs leading to permanent study discontinuation. No participant experienced a serious infection, meningococcal infection, allergic and/or hypersensitivity reaction, or thromboembolic event.

Overall, SAR445088 was generally well-tolerated. No new safety concerns were identified.

Pharmacodynamic Results:

After a single dose of SAR445088 30 mg/kg IV, mean percent CP activity decreased from 49.70% at baseline to <10% on D1 1H, followed by gradual increase of CP activity. The mean CH50 value decreased from 21.7 IU/mL at baseline to <10 IU/mL at D1 1H. At the EOS visit, the mean CH50 value remained <10 IU/mL. After a single dose of SAR445088 15 mg/kg IV, mean percent CP activity decreased from 56.09% at baseline to 10.23% on D1 1H, followed by gradual increase of CP activity. The mean CH50 value decreased from 25.7 IU/mL at baseline to <10 IU/mL at D1 1H. At the EOS visit, the mean CH50 value was 13.6 IU/mL. No reduction in AP activity was observed for the duration of the study.

Figure 5:
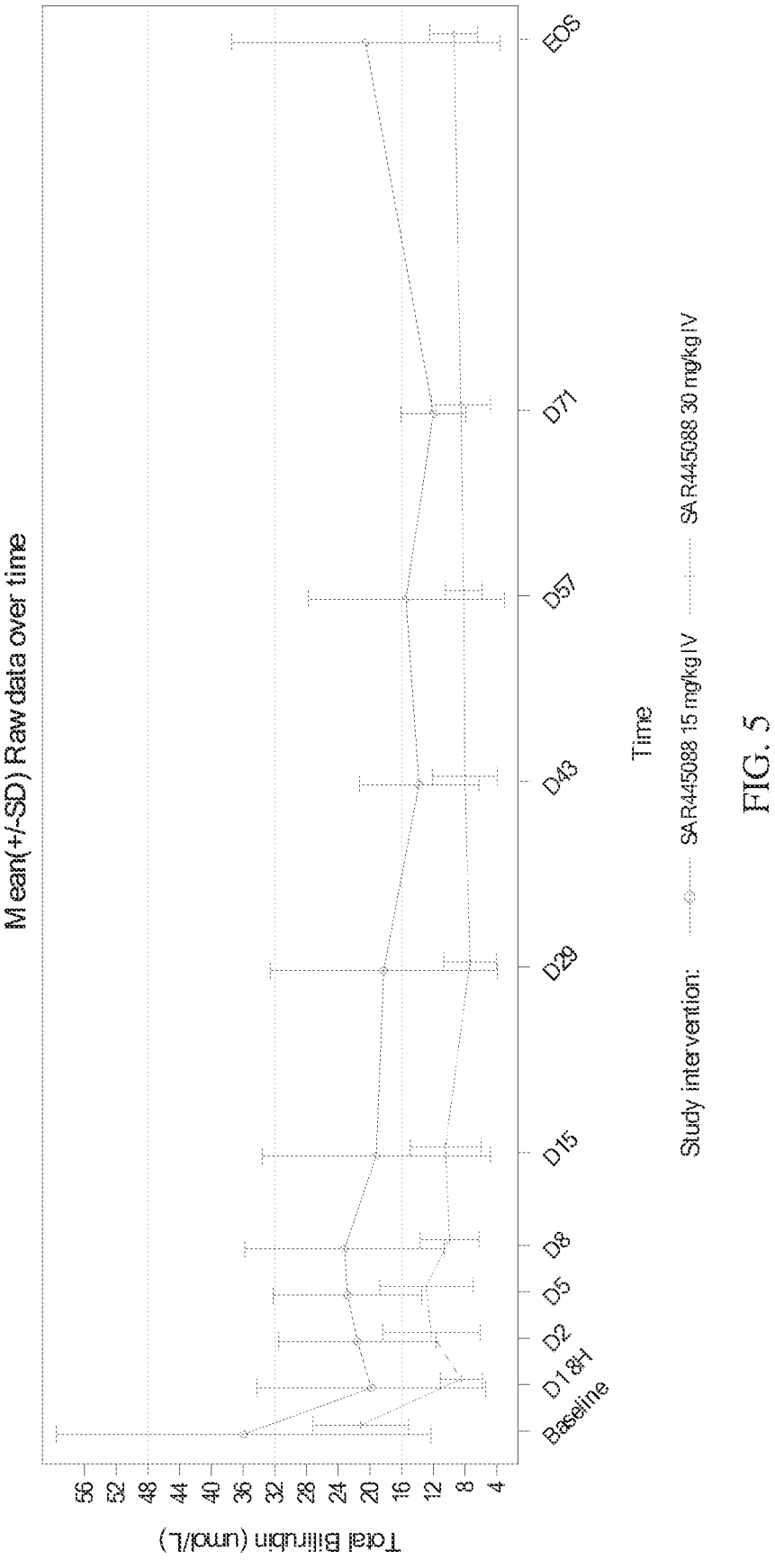
FIG. 5 shows the summary plots on total bilirubin (umol/L) change from baseline over time—biomarker activity (BA) population. Baseline is defined as the D1–1H assessment value. D=day; H=hour.

The effect of SAR445088 on clinical biomarkers of hemolysis was evaluated using mean total bilirubin (a marker of red blood cell destruction) and mean hemoglobin, by timepoint. After a single dose of 30 mg/kg, mean bilirubin decreased from 21.18 μmol/L (upper limit of normal, 17.1 μmol/L) at baseline to a trough value of 7.35 μmol/L at D29, and 9.41 μmol/L at the EOS visit. After a single dose of 15 mg/kg, mean bilirubin decreased from 35.91 μmol/L at baseline to a trough value of 11.97 μmol/L at D71, with a value of 20.52 μmol/L at the EOS visit (FIG. 5).

Figure 6:
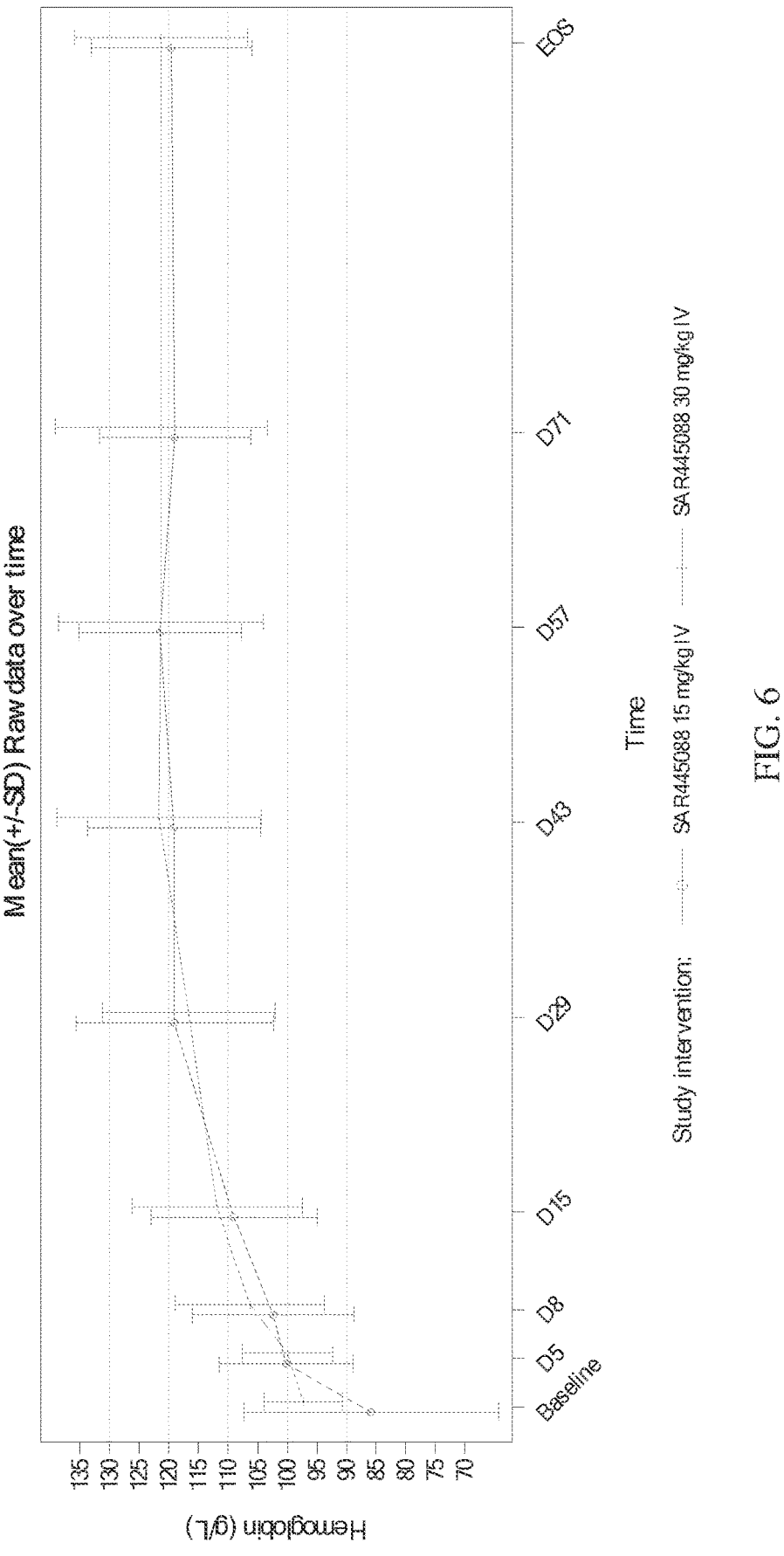
FIG. 6 shows the summary plots on hemoglobin (g/L) change from baseline over time–BA population. Baseline is defined as the D1–1H assessment value. D=day; H=hour.

After a single dose of 30 mg/kg, hemoglobin increased from a mean of 97.3 g/L at baseline to a peak of 121.7 g/L at D43, with a value of 121.3 at the EOS visit. After a single dose of 15 mg/kg, hemoglobin increased from 85.9 g/L at baseline to a peak of 121.5 g/L at D57, with a value of 119.5 g/L at the EOS visit (FIG. 6). In the 15 mg/kg group, two participants received transfusion of packed red blood cells on the day of SAR445088 administration. Analysis of hemoglobin increase from baseline in this group may be influenced by these transfusion events.

Figure 7:
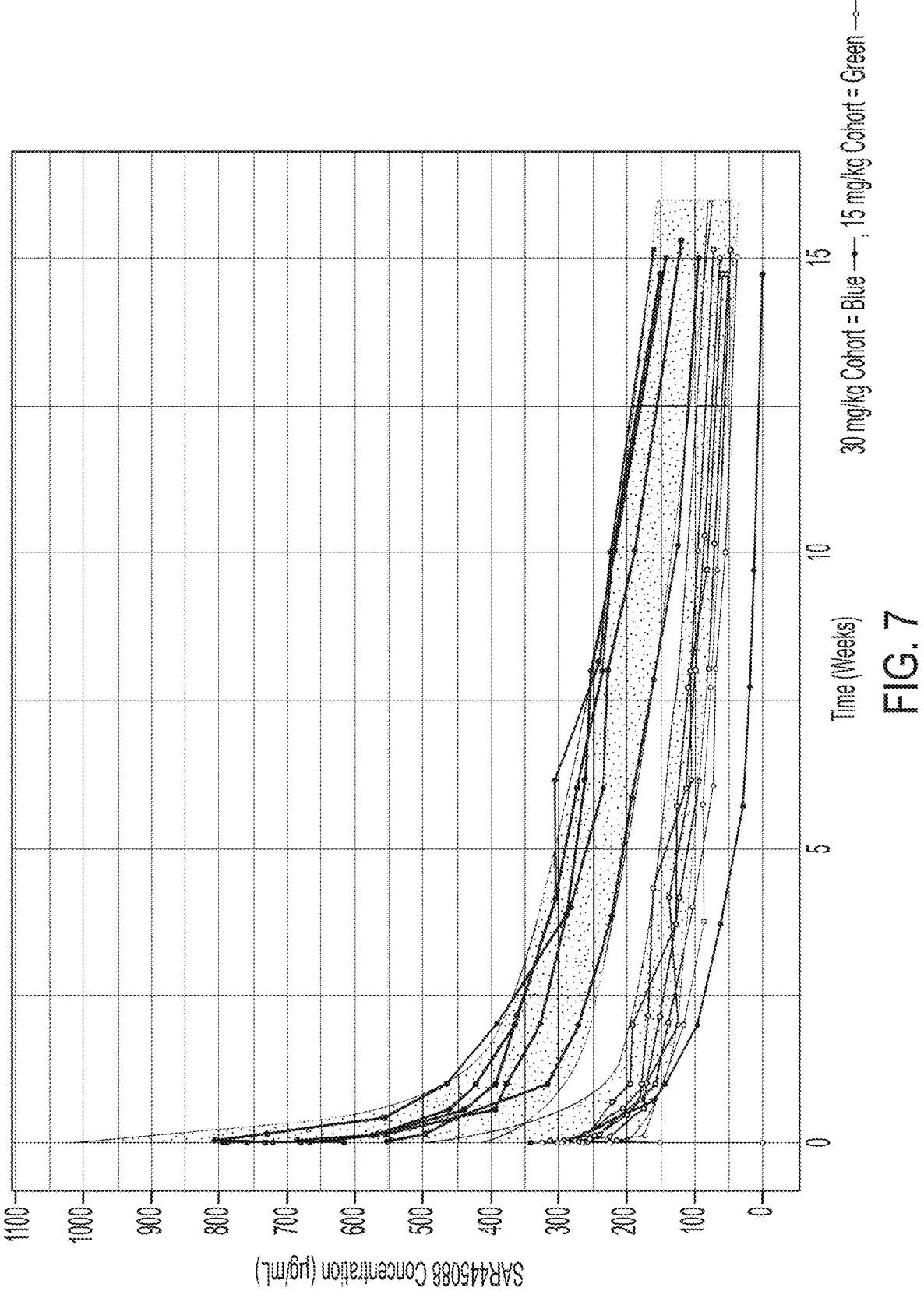
FIG. 7 shows the observed SAR445088 concentration time profile in CAD patients and 90% prediction interval with the popPK model based on healthy subject data.

Pharmacokinetic Results:

SAR445088 concentrations were generally within the 90% prediction interval based on a PopPK model developed in healthy participants, indicating that the PK for CAD participants were similar to that of healthy participants (FIG. 7).

Other Results:

There was no participant with treatment-induced ADA, treatment-boosted ADA, or treatment-emergent ADA. There was no ADA-inconclusive participant.

CONCLUSIONS

A single dose of SAR445088 had an acceptable safety and tolerability profile in adult participants with CAD. Sustained reduction in CH50 was observed after single doses of 30 mg/kg IV and 15 mg/kg IV during 15 weeks of follow-up. The observed reduction in CH50 values corresponded to a decrease in total bilirubin, and an increase in hemoglobin during the follow-up period. Collectively, these findings demonstrate that a single IV dose of or 15 mg/kg of SAR445088 leads to classical complement inhibition, control of hemolysis, and improvement in anemia in adult patients with CAD.

Example 3. SAR445088 Dose Regimen Selection for Phase 2/3 Studies

The main objective of this study was to simulate dosing regimens for Phase 2/3 studies in patients with cold agglutinin disease (CAD) and chronic inflammatory demyelinating polyneuropathy (CIDP).

Methodology:

Software

SAR445088 concentration versus time data were simulated using NONMEM software version 7.4.1 (ICON, Development Solutions, Elliot City, MD, USA).

Simulation dataset, graphical analysis, descriptive statistics and evaluation of NONMEM outputs were conducted using R (R Core Team. R: A Language and Environment for Statistical Computing. R Foundation for Statistical Computing. Vienna, Austria, 2019).

Population Pharmacokinetic/Pharmacodynamic Model

PopPK and PopPK/PD Models in Healthy Subjects

A population pharmacokinetic (PopPK) model and a population pharmacokinetic/dynamic (PopPK/PD) model were developed for SAR445088 using data from single and multiple ascending dose studies in healthy adult participants (Example 1). These studies investigated intravenous (IV) doses of 2 to 50 mg/kg and subcutaneous (SC) doses of 300 to 600 mg as a single or repeated doses.

The pharmacokinetics (PK) of SAR445088 in healthy subjects was adequately described by a two-compartment model with linear elimination with first order absorption after subcutaneous (SC) administration. The typical clearance (CL) was 2.21 mL/h. The total volume of distribution (V) was consistent with plasma volume indicating the drug distribution being confined to blood circulation. Body weight on peripheral volume of distribution (V p) was the primary source of SAR445088 PK variability. V p increased 2.3-fold as body weight increased from 50.4 kg to 100.8 kg (the range observed in the healthy subject studies). Moreover, all other covariates including age, gender, race, and anti-drug antibody (ADA) status were evaluated and not found to have statistically significant effect on SAR445088 PK.

The popPK model suggested that SAR445088 was more distributed in the organs and tissues in individuals with higher body weight. The fast intercompartmental clearance (Q=14 mL/h) and slow CL indicated that SAR445088 resided in the central volume of distribution ($V_c$) most of the time. Hence, body weight over the tested range was expected to have negligible impact on SAR445088 plasma concentration.

PopPK/PD models were developed for complement pathway activity as measured by Wieslab classical pathway (CP) and 50% hemolytic component (CH50) as pharmacodynamic (PD) markers. A discrepancy was observed in the PK/PD of SAR445088 to CP and CH50: the $IC_{90}$ for CP was 458 μg/mL, and that for CH50 was 57.0 μg/mL. As a conservative approach, the CP PK/PD model was used to propose the dosing regimen for Phase 2 CAD and CIDP studies.

Simulations for Dose Selection for Phase 2/3 Studies

The popPK and popPK/PD models were used for simulations of different dosing regimens (once per week, qw, once every other week, q2w, once per month, qm, once every 12 weeks, q12w), with or without an IV or SC loading dose, with the goal of achieving CP below 10% (i.e., inhibition of >90%) or CH50 of <10 U/mL.

Dosing Regimen Selection for Phase 2 CAD and CIDP Studies

Based on the popPK/PD model for CP mentioned above, single IV doses of 15 and 30 mg/kg were chosen for a proof-of-concept study in CAD patients (Example 2). These models were also used to select a loading dose of 50 mg/kg IV followed by 600 mg SC every week starting Day 8 for the Phase 2 CIDP studies.

Flat Dose Versus Body-Weight Based Regimen

The popPK model for SAR445088 was used for simulating PK by body weight. As a conservative approach to evaluate body weight impact on SAR445088 exposure, the PK parameters CL and V were allometrically scaled based on body weight. The exponent used for CL was 0.85, and that for V was 1. The equations for CL and V were as follows:

$$Cl = TVCL * \left(\frac{WT_I}{WT_{median}}\right)^{0.85} * e^{\eta cL}$$

$$V = TVV * \left(\frac{WT_I}{WT_{median}}\right)^{1} * e^{\eta V}$$

The body weight distribution from 35 to 200 kg was categorized into bins to facilitate comparison according to Table 6.

TABLE 6

| Weight bins bln |
| --- |
| A: 35-54 kg |
| B: 55-64 kg |
| C: 65-74 kg |
| D: 75-84 kg |
| E: 85-94 kg |
| F: 95-105 kg |
| G: 106-130 kg |
| H: 130-200 kg |

From the body weight distribution, patients (n=1000) were randomly selected with replacement using an R script. For each patient (n=1000), the SAR445088 exposure profile was simulated to steady state. PK parameters area under the curve at steady state ($AUC_{ss}$) and predose concentration at steady state ($C_{trough}$) were estimated.

Body Weight Distribution and Simulations

The PK/PD model for CH50 was used to evaluate the following regimens, matched for a 70 kg individual, for CAD and CIDP patient populations:

Flat dosing regimen: 3.5 g IV q12w with an additional 3.5 g IV dose on Day 29

Weight-based dosing regimen: 50 mg/kg q12w with an additional 50 mg/kg IV dose on Day 29.

Body weight distribution data was obtained from the following studies:

1) CAD: Cadenza (BIVV009-03) and Cardenal (BIVV009-04) studies; n=66, median=65.6+/−13.5 kg.

2) CIDP: CIDP patient population from a Center for Disease Control database (Centers for Disease Control and Prevention. US CIDP patient body weight. February 2022); n=100, median=83.9+/−35.8 kg.

The population densities of the indications overlapped, with the majority of patients in the 50 to 90 kg range.

Results and Discussion:

Dose Regimen Selection for Phase 2 CAD and CIDP Studies

CAD

Figure 8:
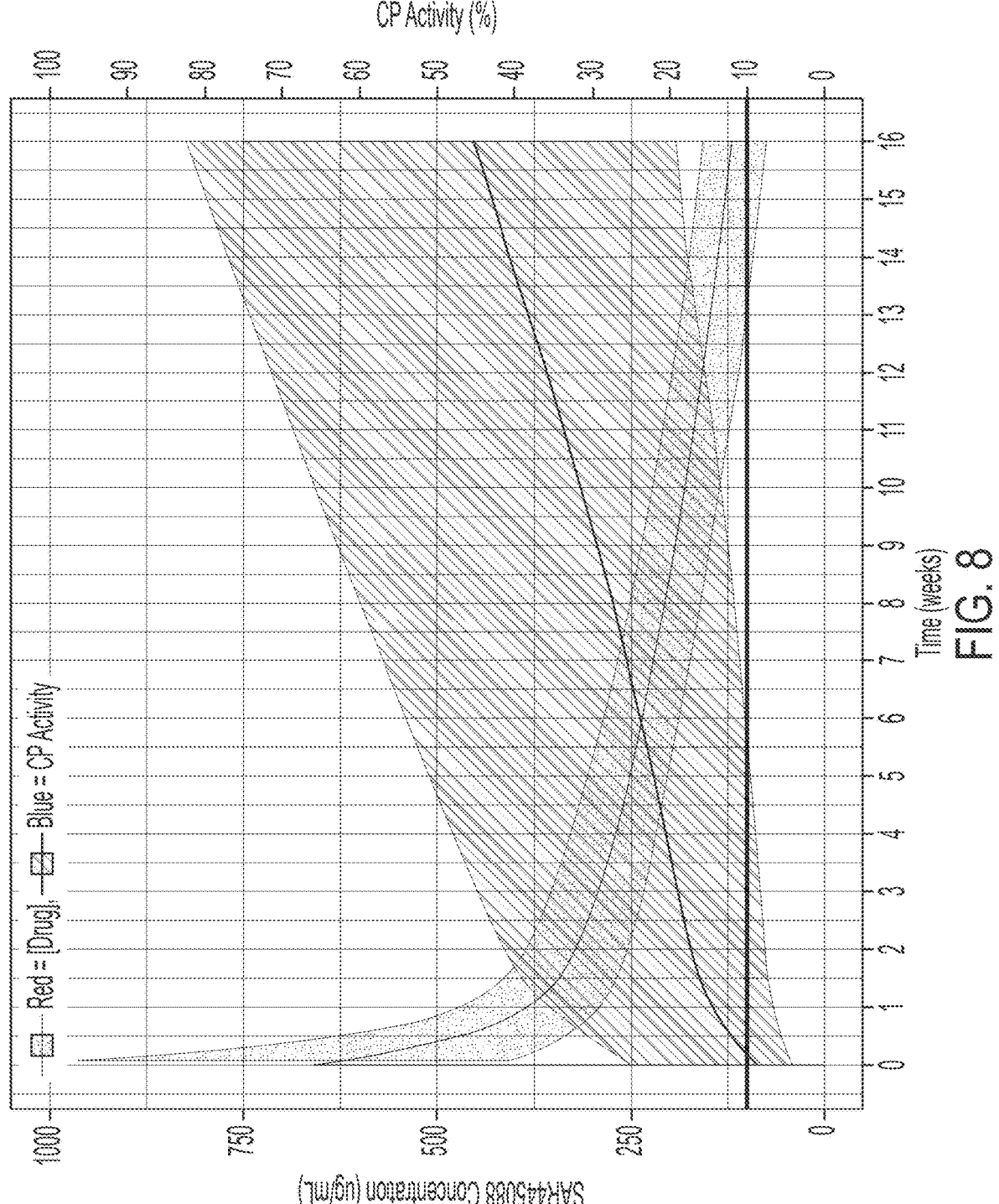
FIG. 8 shows PK/PD simulations for SAR445088 regimen for Phase 2 CAD study: 30 mg/kg IV.

Based on the PK/PD model for CP, a single IV dose of 30 mg/kg in CAD patients was predicted to achieve a maximum concentration ($C_{max}$) of ~0.660 µg/mL with CP below 10% in 60% of patients (FIG. 8).

CIDP

Figure 9:
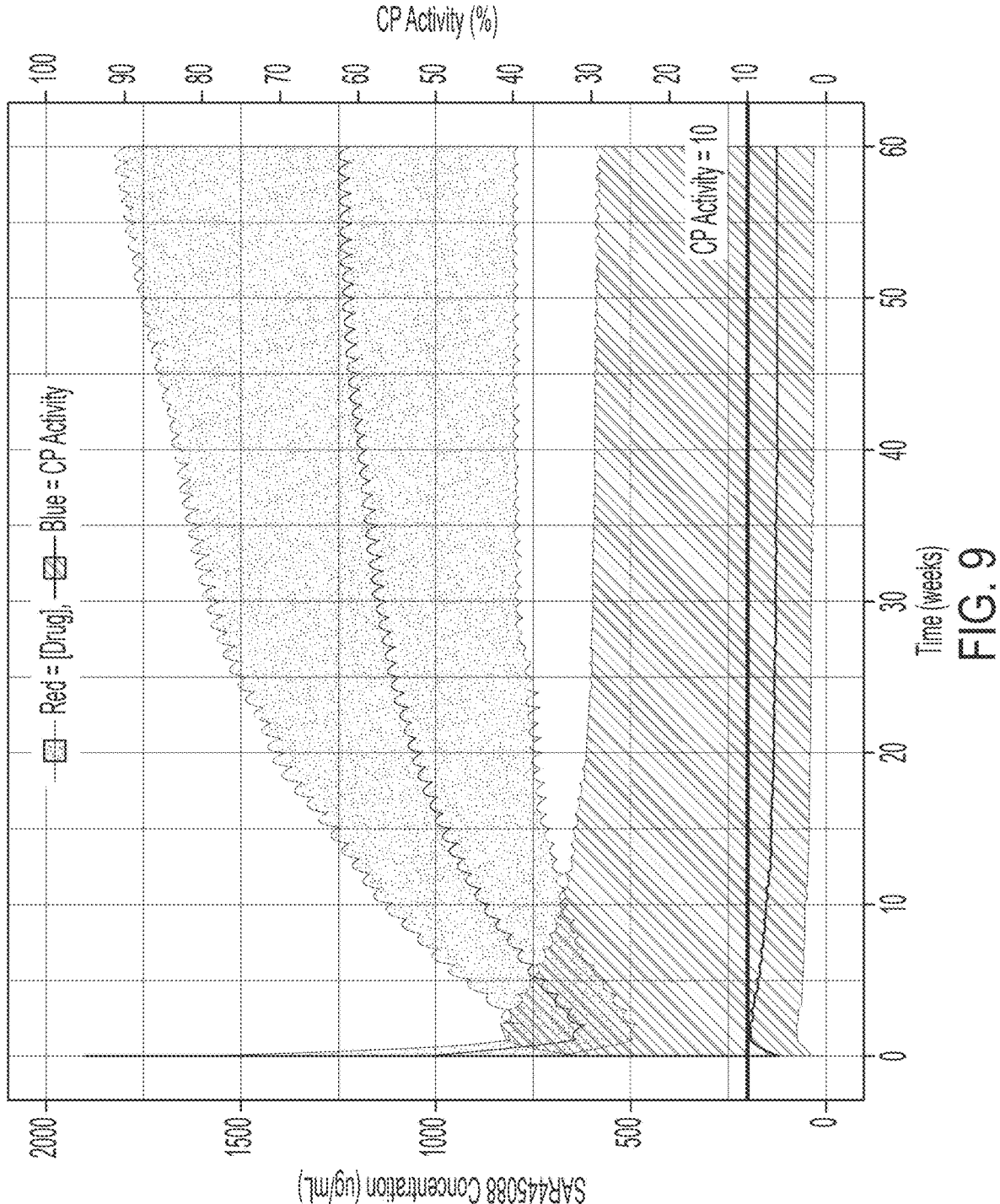
FIG. 9 shows PK/PD simulations for SAR445088 regimen for Phase 2 CIDP Studies: mg/kg IV on Day 1+600 mg SC qw from Day 8 onwards. Red line: predicted SAR445008 concentrations, shaded red 90% prediction interval. Blue line: predicted CH50 level; shaded blue 90% prediction interval.

A loading dose of 50 mg/kg IV followed by 600 mg SC qw on Day 8 predicted the steady-state pre-dose concentration ($C_{trough}$) to be approximately 1210 µg/mL with CP value below 10% in the majority of patients (50%) throughout the treatment period (FIG. 9). The estimated exposure margin based on $AUC_{ss}$ comparing the 26-week nonhuman primate (NHP) study no-observed-adverse-effect (NOAEL) (AUC0-12 wks=8,388,000 µg*h/mL) was greater than 2.

A loading dose was necessary to rapidly achieve 90% CP inhibition. For example, a 1200 mg SC dose administered every 2 weeks (q2w) achieves 90% CP inhibition approximately 12 weeks into treatment with $C_{trough}$ at 1145 µg/mL.

Alternative Regimens

Lower Dose

The dose proposed for Phase 2 CIDP was based on CP PK/PD as a conservative approach. Regimens based on the CH50 PK/PD, requiring a lower maintenance dose, were proposed for SC and IV.

SC. A proposed lower maintenance dose regimen with SC administration was Day 1 mg/kg IV and Day 8 300 mg SC qw. Based on the CH50 popPK/PD model, this regimen achieves rapid SAR445088 level that reduces CH50 value to below 10 U/mL, and is sustained with a $C_{trough}$ of ~600 ug/mL for the duration of treatment.

IV. A proposed lower maintenance dose regimen with IV administration was Day 1 50 mg/kg IV q8w. Based on the CH50 popPK/PD model, this regimen achieves rapid SAR445088 level that reduces CH50 to below 10 U/mL, and is sustained with a $C_{trough}$ of ~800 g/mL for the duration of treatment.

Flat Dose Versus Body-Weight Based Regimen

Figure 10:
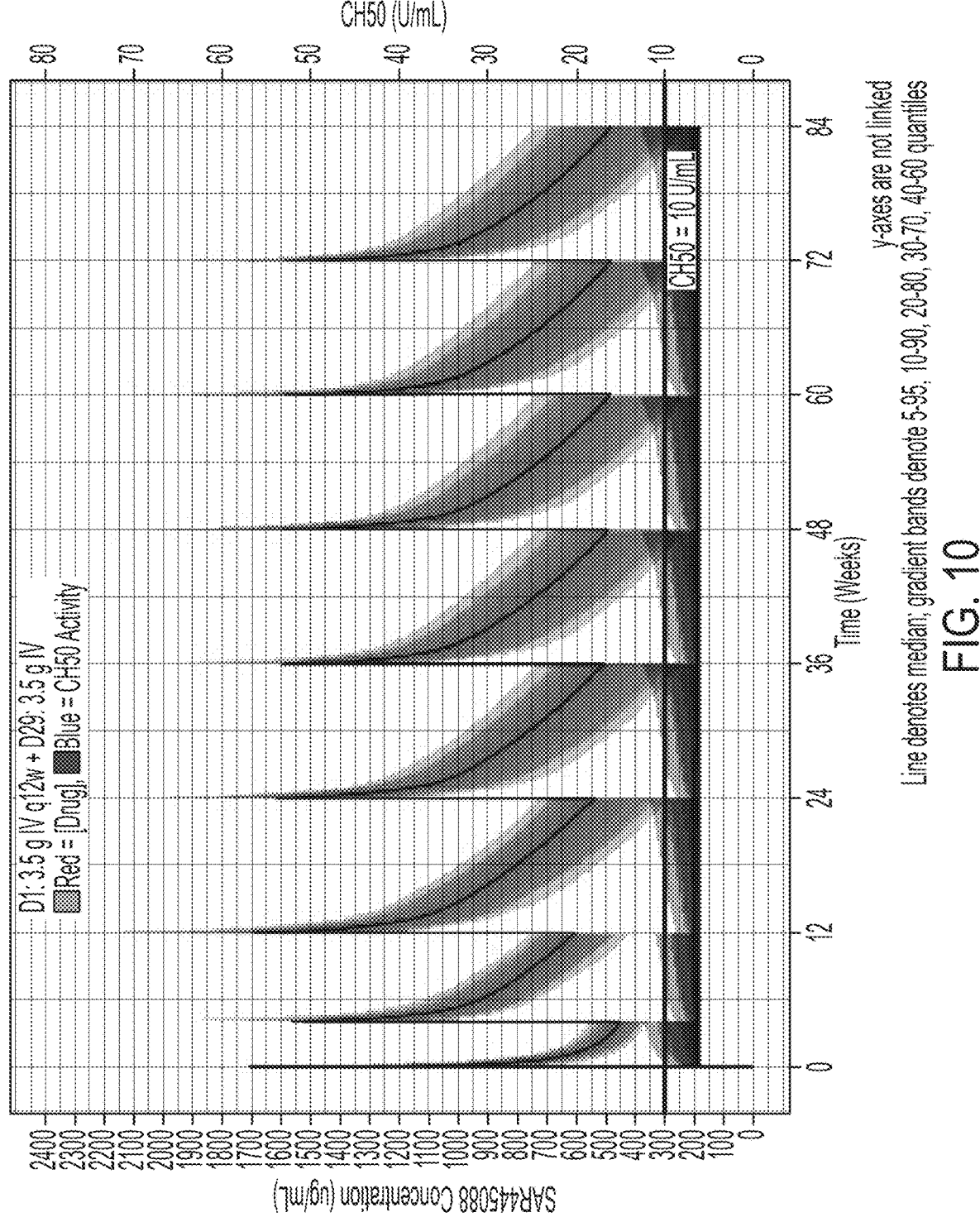
FIG. 10 shows PopPK simulation for flat dose regimen: 3.5 g IV q12w starting on Day 1+3.5 g IV on Day 29.

A body-weight based regimen of a 50 mg/kg IV dose administered every twelve weeks (q12w), with an additional 50 mg/kg IV dose on Day 29 and an equivalent flat dose for a 70 kg individual were compared to support dose selection for the CAD Phase 3 study. A simulation is presented in FIG. 10 for 3.5 g IV every twelve weeks with an additional 3.5 g IV dose on Day 29. At steady state, SAR445088 levels in 12% of patients were predicted to be below 300 µg/mL, but were predicted to be above 100 µg/mL in 100% of patients. A $C_{trough}$ comparison between 3.5 g and 50 mg/kg for the proposed regimen showed $C_{trough}$ to be comparable between the two approaches (Table 7).

TABLE 7

PopPK simulation $C_{trough}$ for flat versus weight-based dose regimen: 3.5 g or 50 mg/kg IV q12w starting on Day 1 + 3.5 g or 50 mg/kg IV on Day 29

| Time | Ctrough (µg/mL) | |
| --- | --- | --- |
| (Wks) | Flat | Weight-Based |
| 4 | 404 | 529 |
| 13 | 567 | 567 |
| 25 | 537 | 522 |
| 37 | 519 | 498 |
| 49 | 513 | 491 |
| 61 | 508 | 488 |
| 73 | 506 | 486 |
| 85 | 505 | 485 |

Figure 11:
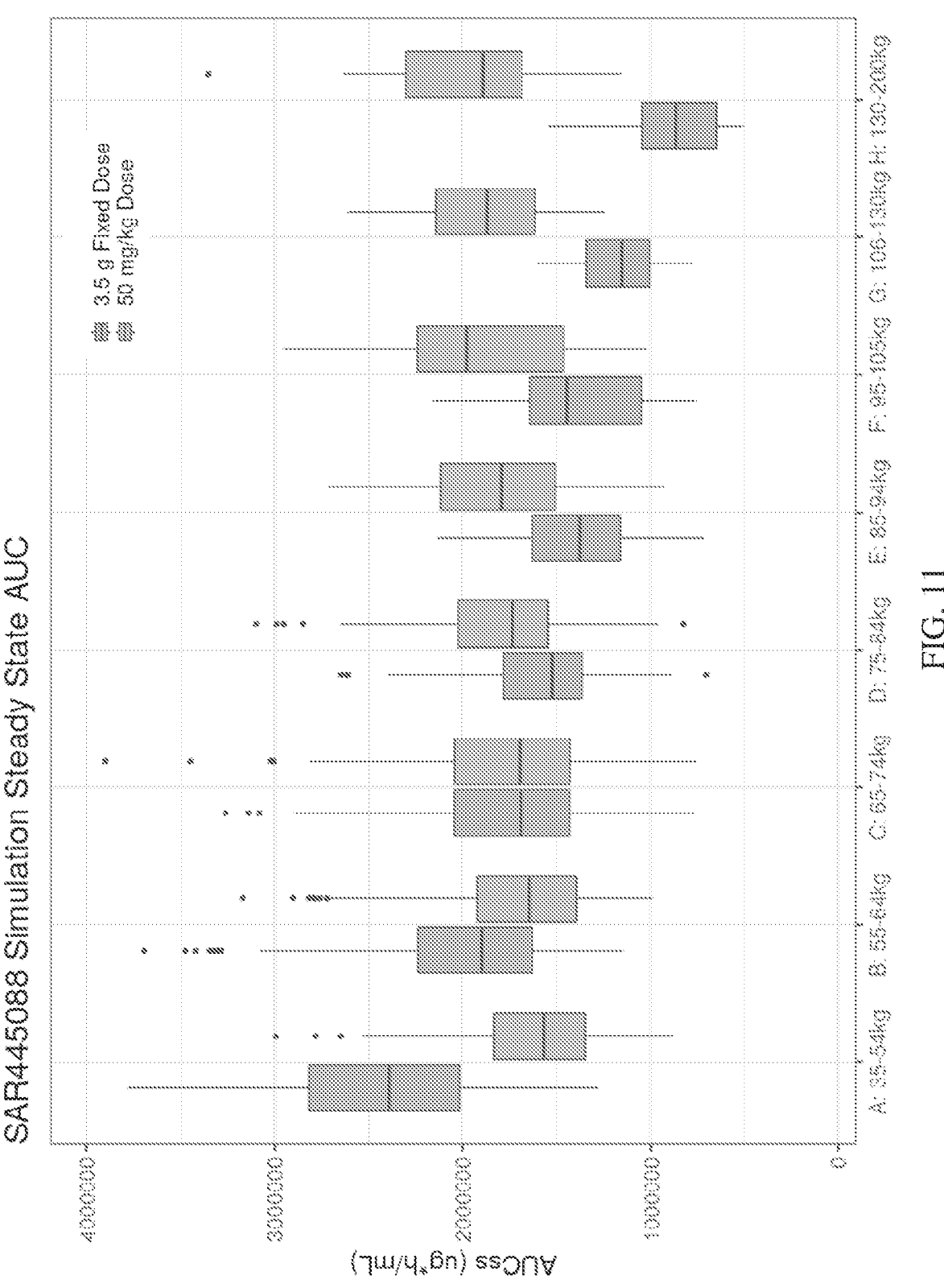
FIG. 11 shows SAR445088 flat vs. weight-based dose simulated steady state AUC boxplots.

The simulated area under the curve at steady state ($AUC_{ss}$) is presented in FIG. 11 and summarized in Table 8. For the flat dose approach, there was a trend in $AUC_{ss}$ decreasing from low body weight (bin A) to high body weight (bin H); this decrease was ~2.8-fold. For the weight-based dose regimen, there was trend in $AUC_{ss}$ increase from low body weight (bin A) to high body weight (bin H); this increase was ~1.2-fold.

TABLE 8

| bln | n | Fixed_Dose_AUCss_Median | WT_Dose_AUCs_Median | Fixed_vs_WT_Ratio |
|---|---|---|---|---|
| | | SAR445088 flat vs. weight-based dose simulated steady state AUC | | |
| A: 35-54 kg | 141 | 2409601.6 | 1567144 | 1.56 |
| B: 55-64 kg | 296 | 1897776.2 | 1643898 | 1.15 |
| C: 65-74 kg | 309 | 1694159.8 | 1699211 | 1.00 |
| D: 75-84 kg | 143 | 1522292.0 | 1737181 | 0.88 |
| E: 85-94 kg | 37 | 1378447.4 | 1794347 | 0.77 |
| F: 95-105 kg | 35 | 1445404.0 | 1978139 | 0.73 |
| G: 106-130 kg | 31 | 1151181.9 | 1870214 | 0.62 |
| H: 130-200 kg | 17 | 862918.8 | 1891702 | 0.46 |

For the middle weight bins 65-105 kg, the exposure between 3.5 g flat and 50 mg/kg dose approaches were comparable and, where most of the patients were expected. The biggest difference was observed for the extreme low (bin A) and high (bin H) weights, where the flat to weight-based $AUC_{ss}$ ratio was 1.54 for bin A, and 0.46 for bin H.

Figure 12:
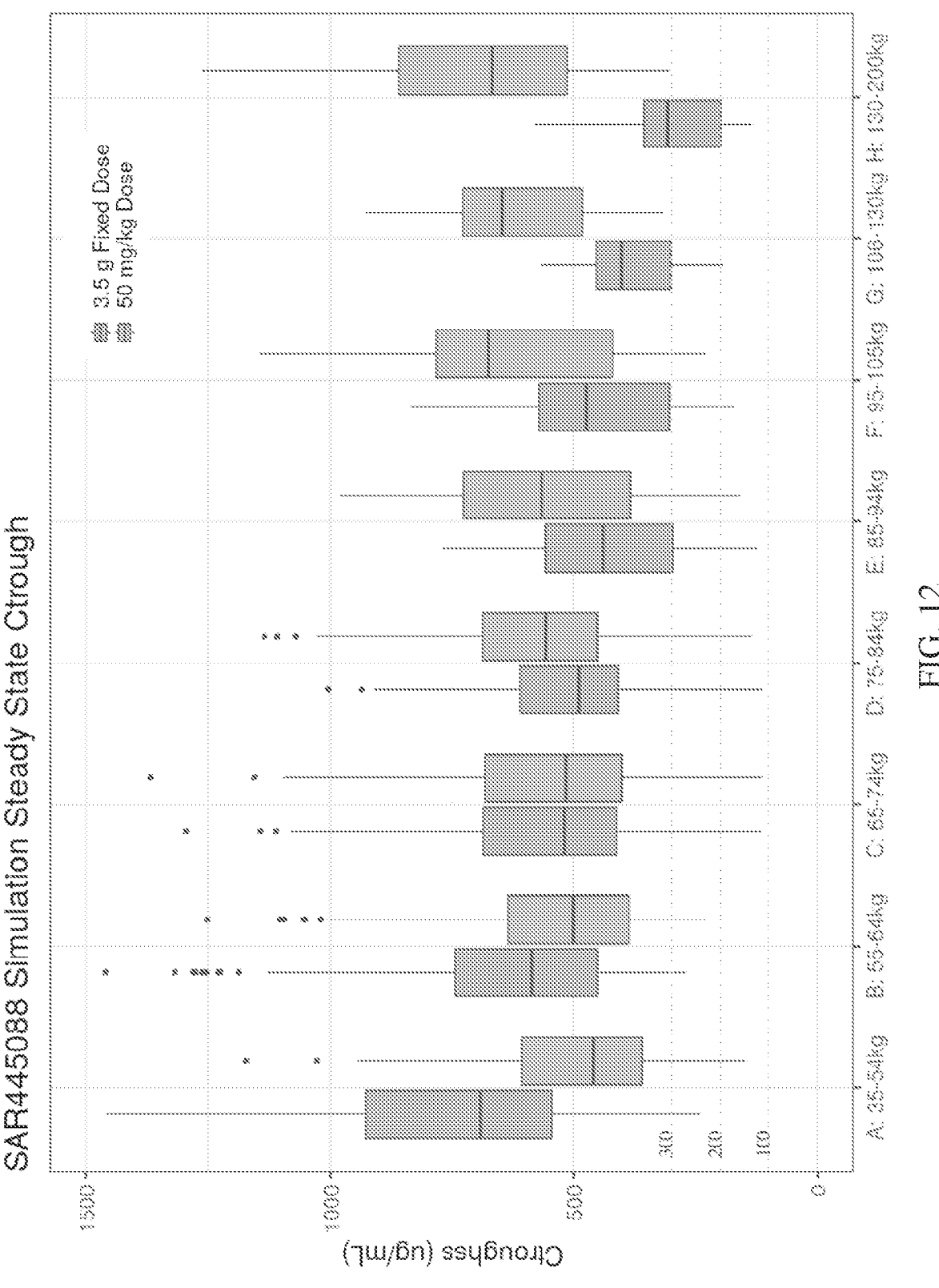
FIG. 12 shows SAR445088 flat vs. weight-based dose simulated steady state $C_{trough}$ boxplots.

The simulated minimum plasma drug concentration at steady state ($C_{trough}$) is present in FIG. 12 and summarized in Table 9. For the 3.5 g flat dose approach, there was a trend in $C_{trough}$ decreasing from the low body weight (bin A) to high body weight (bin H); this decrease was ~2.3 fold. For the 50 mg/kg dose approach, there was a trend in $C_{trough}$ increasing from the low body weight (bin A) to high body weight (bin H); this increase was ~1.5-fold. Similar to $AUC_{ss}$, the middle bins (C to F) were comparable between flat and weigh-based dose approaches. The biggest difference was observed for the extreme low (bin A) and high (bin H) weights, where the flat to weight-based $C_{trough}$ ratio was 1.56 for bin A, and 0.46 for bin H.

TABLE 9

| bln | n | Fixed_Dose_Ctroughss_Median | WT_Dose_Ctroughss_Median | Fixed_WT_Ratio |
|---|---|---|---|---|
| | | SAR445088 flat vs. weight-based dose simulated steady state $C_{trough}$ | | |
| A: 35-54 kg | 141 | 715.74 | 459.71 | 1.56 |
| B: 55-64 kg | 296 | 586.58 | 500.71 | 1.17 |
| C: 65-74 kg | 309 | 521.58 | 517.55 | 1.01 |
| D: 75-84 kg | 143 | 488.80 | 556.51 | 0.88 |
| E: 85-94 kg | 37 | 440.02 | 565.74 | 0.78 |
| F: 95-105 kg | 35 | 474.24 | 675.23 | 0.70 |
| G: 106-130 kg | 31 | 402.81 | 646.79 | 0.62 |
| H: 130-200 kg | 17 | 306.58 | 667.50 | 0.46 |

The steady state exposure ($AUC_{ss}$) was compared to the NOAEL established in the 26-week NHP toxicity study (Table 10). All weight bins have an exposure margin greater than 3.

In the healthy subject studies (Example 1), the highest overall exposure was from the 50 mg/kg IV single dose cohort: $C_{max}$ was 1180 µg/mL and $AUC_{0-\infty}$ was 1 390 000 µg*h/mL. No severe adverse events (SAE) were observed in these subjects. The proposed flat dose regimen exposure would be 1.73-0.62 fold from 35-200 kg of the exposure observed in healthy subjects.

TABLE 10

| bln | Fixed_Exposure_Margin | WB_Exposure_Margin |
|---|---|---|
| | Exposure margin versus NHP NOAEL for flat versus weight-based dose regimens | |
| A: 35-54 kg | 3.48 | 5.35 |
| B: 55-64 kg | 4.42 | 5.10 |

TABLE 10-continued

| bln | Fixed_Exposure_Margin | WB_Exposure_Margin |
|---|---|---|
| | Exposure margin versus NHP NOAEL for flat versus weight-based dose regimens | |
| C: 65-74 kg | 4.95 | 4.94 |
| D: 75-84 kg | 5.51 | 4.83 |
| E: 85-94 kg | 6.09 | 4.67 |
| F: 95-105 kg | 5.80 | 4.24 |
| G: 106-130 kg | 7.29 | 4.49 |
| H: 130-200 kg | 9.72 | 4.43 |

An analysis of $C_{trough}$ level was presented in Table 11 for flat dose, and Table 12 for weight-based dose approaches.

TABLE 11

| bln | n | Fixed_300 | Fixed_200 | Fixed_100 |
|---|---|---|---|---|
| | | SAR445088 flat dose simulated $C_{trough}$ analysis. | | |
| A: 35-54 kg | 141 | 4 | 0 | 0 |
| B: 55-64 kg | 269 | 5 | 0 | 0 |
| C: 65-74 kg | 309 | 27 | 5 | 0 |
| D: 75-84 kg | 143 | 13 | 2 | 0 |
| E: 85-94 kg | 37 | 10 | 2 | 0 |
| F: 95-105 kg | 35 | 9 | 2 | 0 |
| G: 106-130 kg | 31 | 8 | 2 | 0 |
| H: 130-200 kg | 17 | 8 | 5 | 0 |
| Total | 982 | 84 | 18 | 0 |

TABLE 12

| SAR445088 weight-based dose simulated $C_{trough}$ analysis | | | | |
| --- | --- | --- | --- | --- |
| bln | n | WB_300 | WB_200 | WB_100 |
| A: 35-54 kg | 141 | 16 | 4 | 0 |
| B: 55-64 kg | 269 | 21 | 0 | 0 |
| C: 65-74 kg | 309 | 29 | 5 | 0 |
| D: 75-84 kg | 143 | 9 | 2 | 0 |
| E: 85-94 kg | 37 | 4 | 1 | 0 |
| F: 95-105 kg | 35 | 3 | 0 | 0 |
| G: 106-130 kg | 31 | 0 | 0 | 0 |
| H: 130-200 kg | 17 | 0 | 0 | 0 |
| Total | 982 | 82 | 12 | 0 |

At steady state, 92% of patients were predicted to have $C_{trough}$ above 300 µg/mL. For the flat dose approach, 84 out of 982 patients were below 300 µg/mL and 18 out of 982 were below 200 µg/mL; this was comparable to the weight-based dose approach, where 82 out of 982 patients were below 300 µg/mL and 12 out of 982 were below 200 µg/mL. Overall, 100% of patients were predicted to be above 100 µg/mL (2-fold above $IC_{90}$).

CONCLUSIONS

1) Bayesian analysis showed that CAD patients had similar PK profiles as those of healthy participants.
2) The reduction of CH50 values upon SAR445088 exposure in CAD patients correlated with improved clinical markers, bilirubin and hemoglobin, confirming CH50 as the relevant PD marker for SAR445088.
3) The dose regimens selected for the Phase 2 studies were predicted to achieve CP below 10% (i.e., inhibition of >90%) or CH50<10 IU/mL over the entire treatment period in the majority of patients. The predicted exposure margin for these regimens was greater than 2 compared to the 26-week NHP NOAEL.
4) A flat dose regimen appeared to produce similar $C_{trough}$ values to that of body weight-based regimen across the body weight range of 35 to 200 kg, which would remain above 100 µg/mL for 100% of the patients. The predicted exposure margin for the flat dose regimen from 35 to 200 kg compared to the 26-week NHP NOAEL was greater than 3.

Example 4. A Phase 2, Multicenter, Open-Label, Non-Randomized, Proof-of-Concept Study Evaluating the Efficacy, Safety, and Tolerability of SAR445088 in Adults with CIDP As described in Example 1 above, a single SAR445088 IV dose of 30 mg/kg or 50 mg/kg resulted in maximum CP inhibition of at least 90%. The 90% cutoff for CP inhibition is derived from prior studies with a first generation C1s mAb used in cold agglutinin disease (CAD), which found 90% CP inhibition to be a predictor of therapeutic effect (blocking of hemolytic activity in the blood compartment) (Jager et al. Blood. 2019 Feb. 28; 133(9):893-901. doi: 10.1182/blood-2018-06-856930. Epub 2018 Dec. 17). Such degree of CP inhibition is therefore expected to translate into therapeutic benefits (improvement of severe hemolytic anemia in CAD). CAD represents a good model of a complement-mediated disease in the blood compartment. However, the target site in CIDP is in the peripheral nerve, which requires SAR445088 to cross the blood-nerve barrier. To account for the uncertainty in the ability for SAR445088 to reach sufficient exposure at this target site in CIDP patients, a two-fold CP IC90 plasma concentration (i.e., 1200 µg/mL) was used as the exposure criteria for the dose selection for Phase 2.

The available data from the Phase 1 studies supported the initiation of a Phase 2 study in CIDP patients, using a dose that is expected to result in the targeted inhibition of the CP of at least 90%, which is anticipated to reverse the pathological activation of this pathway. This effect may induce clinical benefits associated with reversal of nerve inflammation, remyelination, as well as prevention of axonal degeneration.

The purpose of this SAR445088 Phase 2 study is to determine the preliminary efficacy, safety, and tolerability of SAR445088 in three CIDP subpopulations including standard of care (SOC)-Treated, SOC-Refractory, and SOC-Naïve. Results from this Phase 2 study determine proof-of-concept (PoC) and inform Phase 3 trials.

Figure 13:
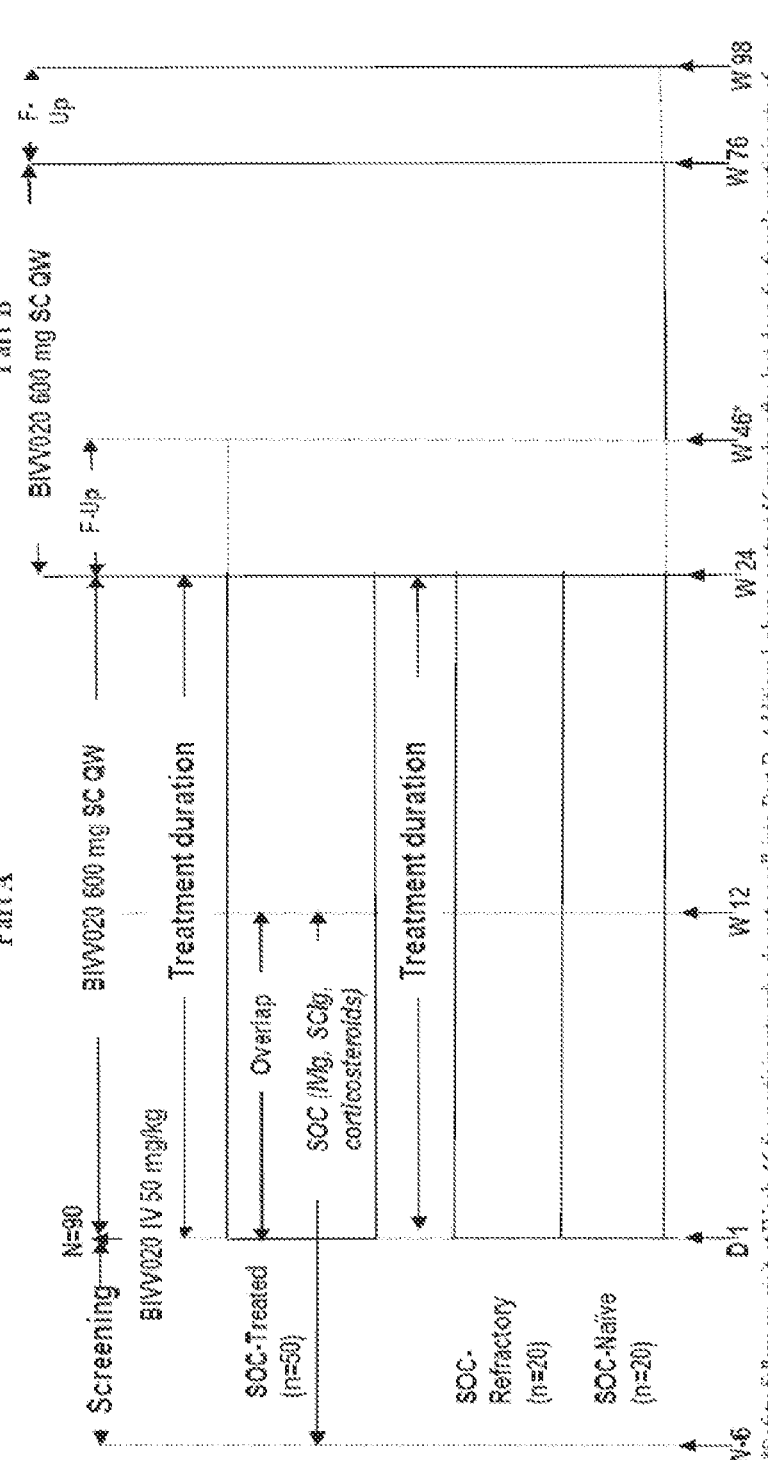
FIG. 13 shows a schematic of a Phase 2 CIDP study.
Figure 14:
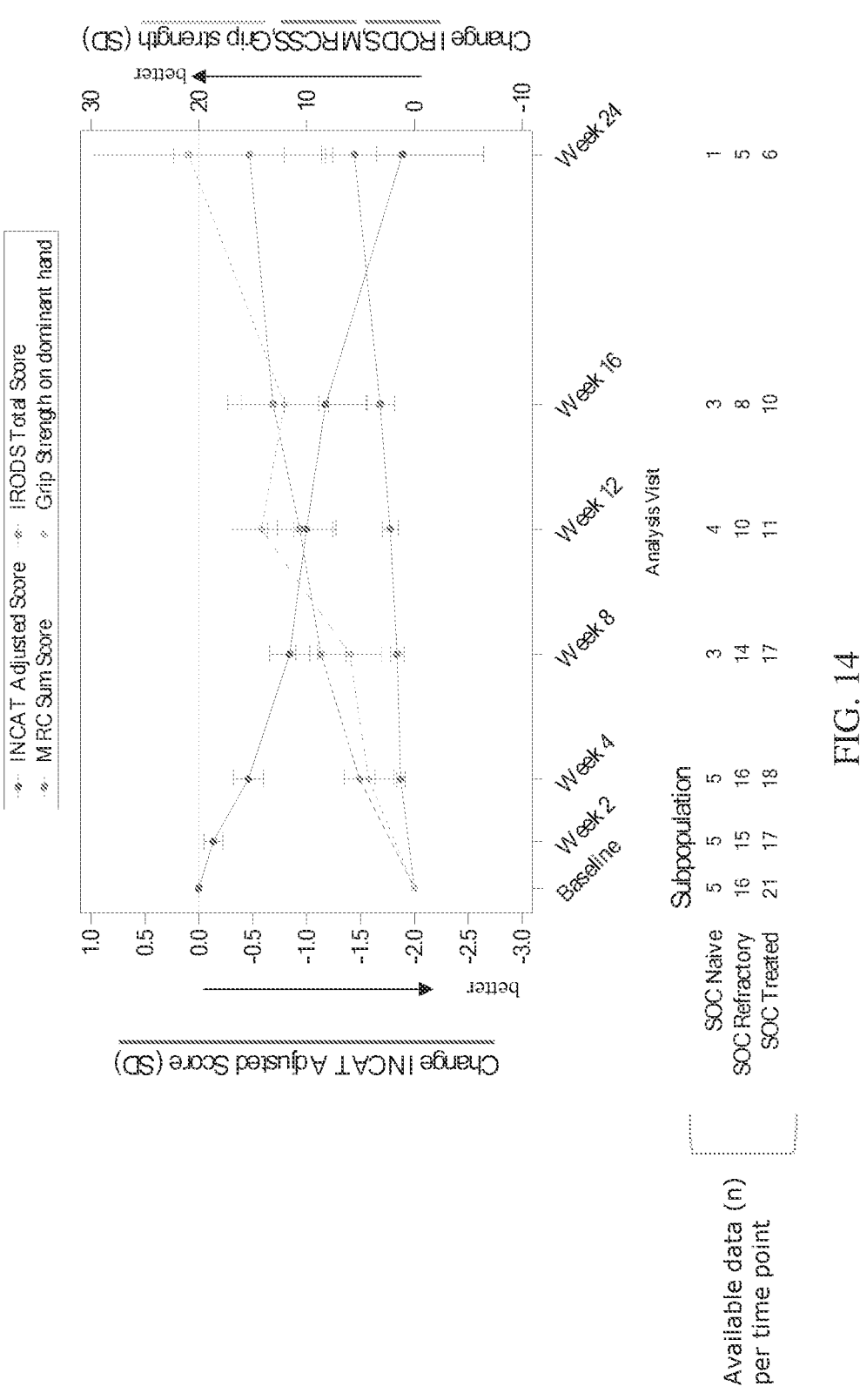
FIG. 14 shows an overview of all efficacy endpoints—the primary endpoint of INCAT score and secondary efficacy endpoints of I-RODS total score, grip strength and MRC sum score (MRCSS), in all trial patients. The change from baseline for the overall data is shown as mean±SD. The number of patients contributing to each timepoint from each subgroup is in the table below the graph.
Figure 15:
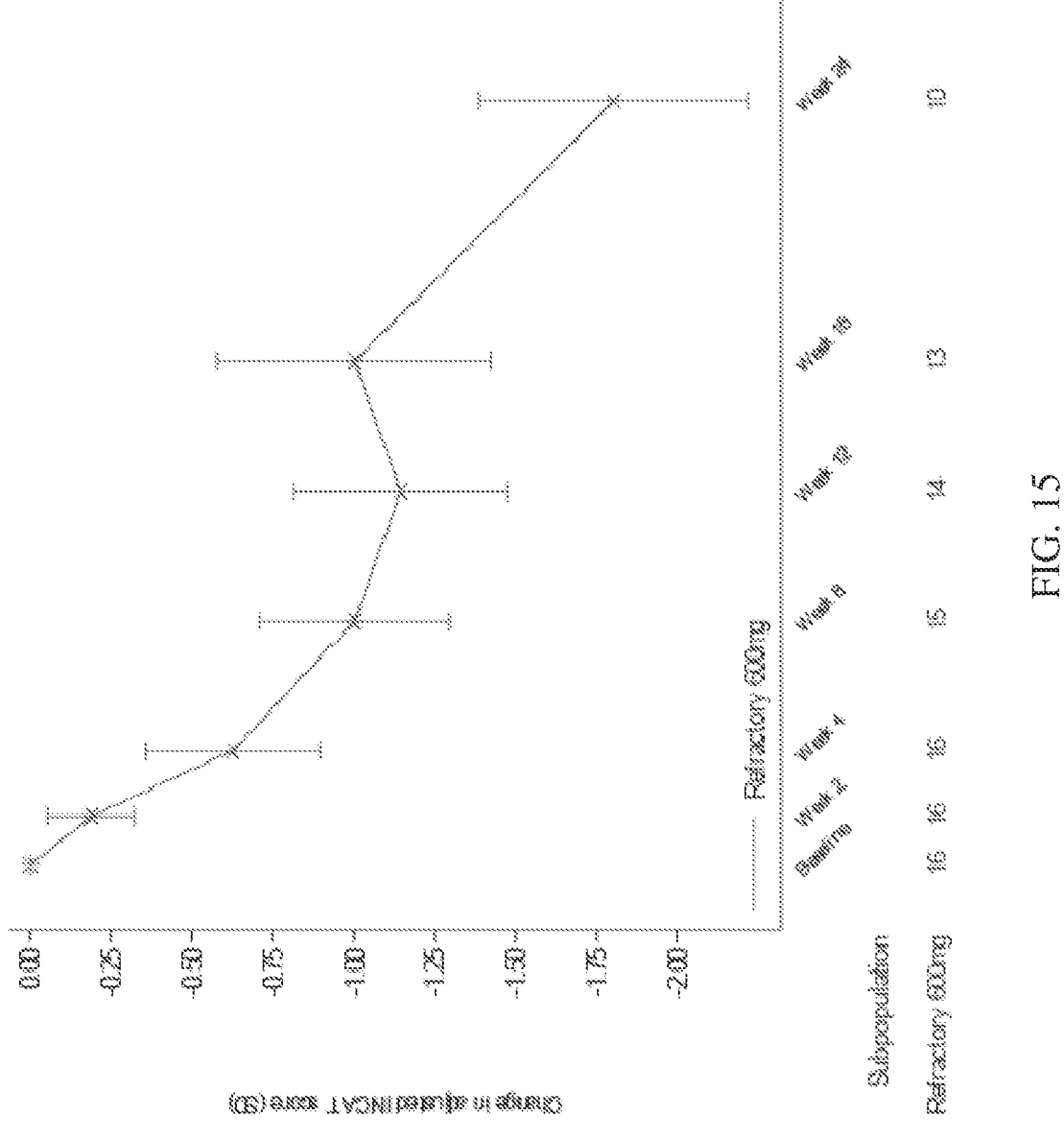
FIG. 15 shows longitudinal change from baseline in INCAT score, SOC-Refractory patients, group data. Data include all available patients/timepoints at the time of cutoff. Error bars indicate standard deviation (SD).
Figure 16:
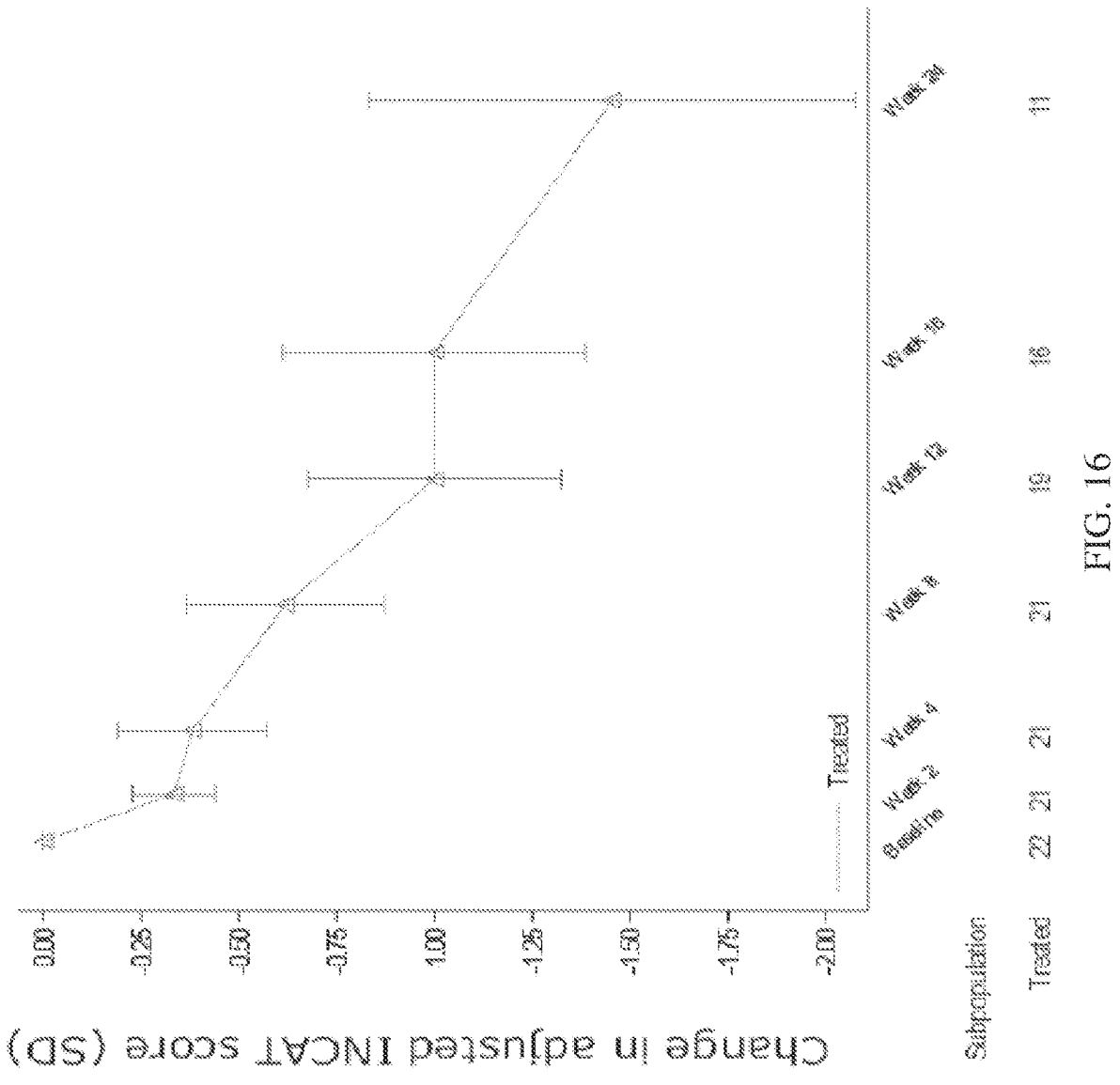
FIG. 16 shows the longitudinal change from baseline in INCAT score, SOC-Treated patients, group data.
Figure 17:
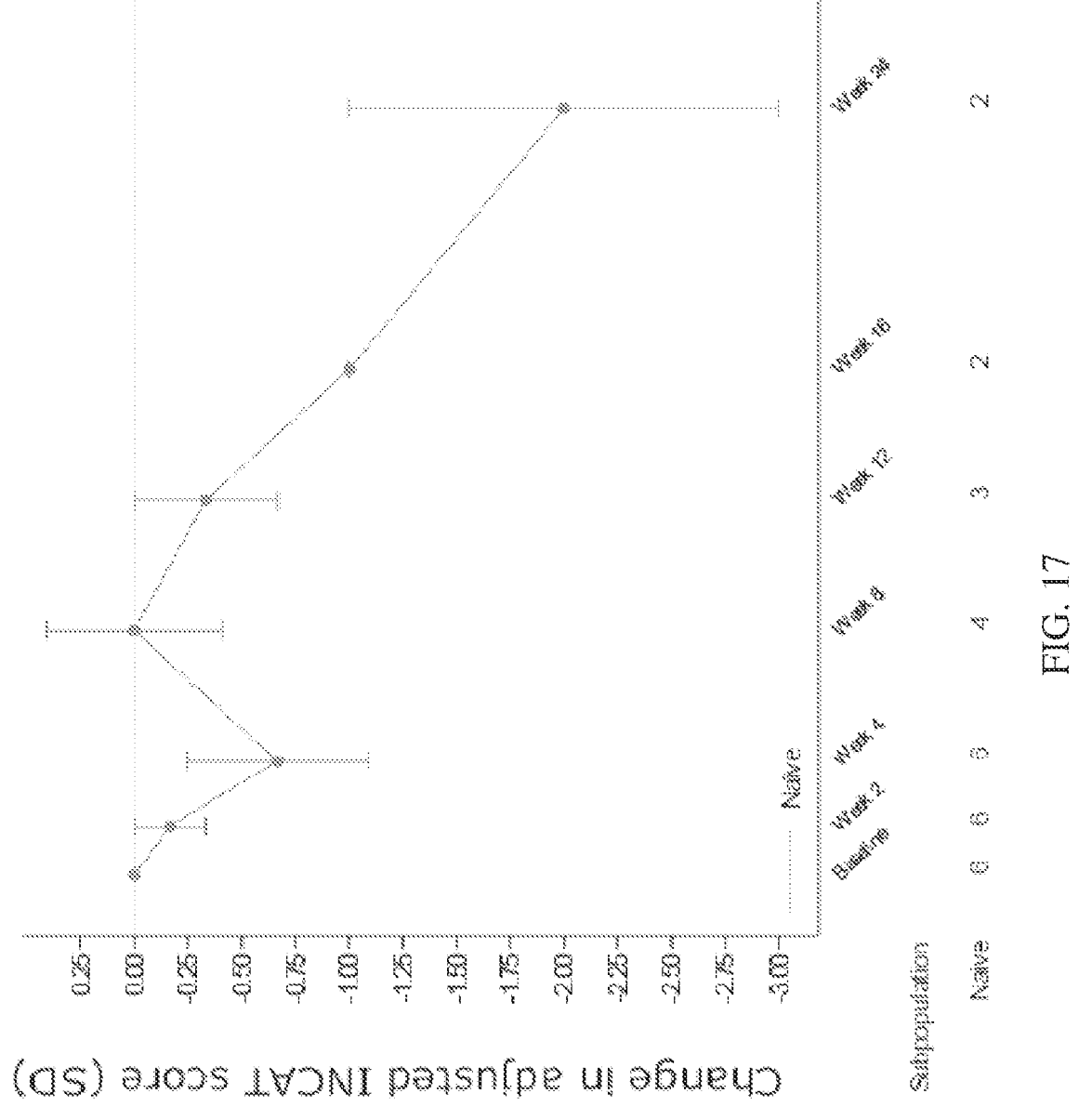
FIG. 17 shows the longitudinal change from baseline in INCAT score, SOC-Naïve patients, group data.

This study is a global multicenter, Phase 2, open label, PoC study evaluating the efficacy, safety, and tolerability of SAR445088 administered to 3 subpopulations of patients with CIDP: patients who are being treated with SOC therapies defined as intravenous immunoglobulin (IVIg), subcutaneous immunoglobulin (SCIg), or corticosteroids; patients with CIDP who are refractory to SOC; and patients with CIDP who are naïve to SOC. The study will consist of two parts: an initial 24-week treatment period (Part A), followed by an optional extension period aimed at evaluating long-term safety and tolerability (Part B) that will provide up to 1 year of additional treatment. A schematic of the study is shown in FIG. 13.

This study is enrolling patients from three CIDP subpopulations, which are separated depending on their experience with SOC therapies, defined as immunoglobulin or corticosteroids:

I. Refractory to SOC (SOC-Refractory); n=20 participants: Patients with evidence of failure or inadequate response to SOC defined as no clinically meaningful improvement and persistent INCAT score ≥2 after treatment for a minimum of 12 weeks on SOC prior to screening, or patients who are unable to receive or continue treatment with immunoglobulins or corticosteroids due to side effects. Patients should not have received immunoglobulins (IVIg or SCIg) within 12 weeks prior to screening. Patients have an INCAT score: 2-9 (a score of 2 should be exclusively from leg disability component of INCAT). Clinically meaningful improvement (and deterioration) is defined, respectively, as one of the following: ≥1-point decrease (increase) in adjusted INCAT score, ≥4 points increase (decrease) in I-RODS total score, ≥3 points increase (decrease) in MRC Sum score, ≥8 kilopascal improvement (decrease) in mean grip strength (one hand), or an equivalent improvement (deterioration) based on information documented in medical records and at the PI's judgement.

II. Naïve to SOC (SOC-Naïve), n=20 participants: Patients without previous treatment for CIDP or patients who received immunoglobulins (IVIg or SCIg) or corticosteroids but were stopped for reasons other than lack of response or side effects. Patients should not have received treatment with immunoglobulins (IVIg or SCIg) or corticosteroids for at least 6 months prior to screening. Patients have an INCAT score: 2-9 (a score of 2 should be exclusively from leg disability component of INCAT).

III. Successfully treated with the SOC therapies (SOC-Treated), n=50 participants: Patients on stable SOC therapy, defined as no change greater than 10% in frequency or dose of immunoglobulin therapy or corticosteroids within 8 weeks prior to screening, remaining at stable SOC therapy until the time of first SAR445088 dosing, who showed documented evidence of objective and clinically meaningful response, and evidence of clinically meaningful deterioration on interruption or dose reduction of SOC therapy within 24 months prior to screening. Clinically meaningful improvement is defined as above.

No control arm is included in this Phase 2 study as CIDP is a rare disease which limits the number of available study participants, and the study design will allow sufficient assessment of the safety and efficacy of SAR445088 in this population.

All participants are receiving an IV loading dose of 50 mg/kg of SAR445088 on Day 1, followed by weekly SC injections containing 600 mg SAR445088. Specifically, for the SOC-Treated group: following an IV loading dose on Day 1, patients treated with IVIg, SCIg or pulsed corticosteroids (IV methylprednisolone or oral dexamethasone) start SAR445088 treatment within one week after the last dose of these treatments. Patients on daily oral corticosteroids (e.g., prednisone or prednisolone) have that treatment tapered during the first 12 weeks of the study. Therefore, SAR445088 600 mg SC is administered weekly with superimposing effects of SOC therapy during the first 12 weeks in the study (overlap period).

Study participants undergo an initial 24-week treatment period (Part A, primary assessment), followed by an optional extension period providing up to 52 additional weeks of treatment (Part B). The primary endpoints in this proof-of-concept study are the following:

I. SOC-Naïve and SOC-Refractory: Percentage of participants responding during the SAR445088 treatment period (up to Week 24). Response is defined as ≥1-point decrease in adjusted INCAT disability score.

II. SOC-Treated: Percentage of participants relapsing after withdrawal of SOC and during the SAR445088 treatment period (up to Week 24). Relapse is defined as ≥1-point increase in adjusted INCAT disability score.

Secondary aims for Part A include safety and tolerability, immunogenicity, and efficacy of SAR445088 (with overlapping SOC therapy for the SOC-Treated group). The primary objective of Part B is to assess long-term safety and tolerability of SAR445088 in patients with CIDP. Percentage of participants with lasting efficacy during the treatment extension period (from Week 24 up to Week 76), i.e., relapse-free (SOC-Treated) or with sustained response (SOC-Refractory and SOC-Naïve), defined as no increase in adjusted INCAT disability score ≥2 points). The secondary objectives of Part B are durability of efficacy during long-term treatment, and long-term immunogenicity.

Each patient group is analyzed independently, depending on the time of study completion of each group. In addition, independent interim analyses are conducted when 50% of participants in each group complete the primary 24-week assessment.

The data from the Phase 2 study is used to refine the design of a planned Phase 3 study in patients with CIDP.
Preliminary Results Two pre-planned interim analyses have been conducted to date in the ongoing Phase 2 study PDY16744. These analyses were performed when 50% of the participants in the standard of care (SOC)-Refractory group and 50% of the participants in the SOC-Treated group completed 24 weeks, which is the time needed for readout of the primary endpoint. The primary endpoint in the SOC-Refractory group is percentage of participants with a clinically meaningful response during the treatment period from Day 1 up to Week 24. Response is defined as a ≥1-point decrease in adjusted INCAT disability score relative to baseline. The primary endpoint in the SOC-Treated group is percentage of participants with a relapse (clinically meaningful deterioration) during the treatment period from Day 1 up to Week 24. Relapse is defined as a ≥1-point increase in adjusted INCAT disability score relative to baseline. INCAT score ranges from 0 (normal) to 10 (maximum disability) and represents the sum of the arm and leg subscales (5 points each). Patients who experienced a relapse at any time during the first 24 weeks of the study (1-point increase from baseline in adjusted INCAT score) were discontinued from SAR445088. Results from the two interim analyses conducted to date showed that:

8 out of 12 participants from the SOC-Refractory group (66.7%) had a clinically meaningful improvement (response, primary endpoint) after receiving SAR445088, which was maintained up to Week 24. The SOC-Refractory group consisted of patients with CIDP who had received multiple treatments. Of the 12 SOC-Refractory participants included in this analysis, 10 had failed or shown inadequate response to IVIg, and 7 of these had also tried additional therapies (corticosteroids, immunosuppressive therapy, plasma exchange). The remaining 2 participants had received prior corticosteroid and immunosuppressive therapy.

11 out of 25 participants from the SOC-Treated group (44%) had a clinically meaningful response after switching from SOC to SAR445088 that was maintained up to Week 24. An additional 44% of SOC-Treated participants (11 out of 25) remained stable (i.e. no change in INCAT disability score) for 24 weeks. The remaining 12% of SOC-Treated participants (3 out of 25) had a clinically meaningful deterioration (relapse, primary endpoint) after switching from SOC to SAR445088. Of the 25 SOC-Treated participants included in the interim analysis, 18 were on IVIg treatment prior to enrollment, 3 were receiving both IVIg and corticosteroid therapy and 4 were receiving corticosteroid therapy alone.

The observed rates of clinically meaningful responses in SOC-Refractory and SOC-Treated groups indicate that the tested dose regimen of SAR445088 is effective in CIDP. The results observed in these interim analyses also met pre-specified criteria for study success and Go-to-Phase 3 decision. Notably, the observed response rate in the SOC-Treated group is remarkable, since it had been anticipated that CIDP disease would be under control in these patients receiving SOC treatment at the time of enrollment, i.e. improvement was not anticipated.

Figure 19:
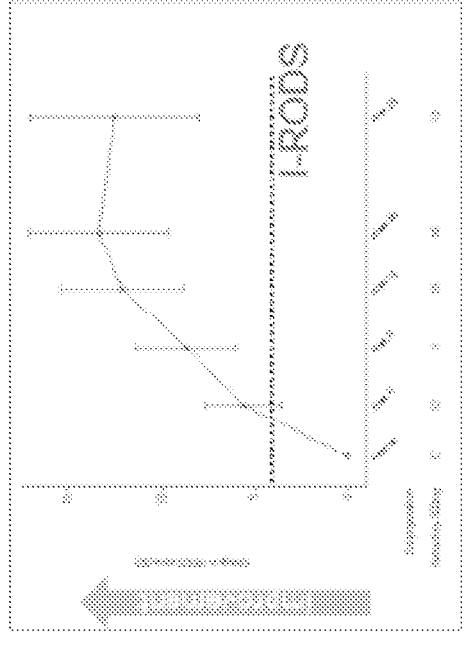
FIG. 19 shows change from baseline in the key clinical outcome measures evaluating functional disability (INCAT disability score, I-RODS) and impairment (grip strength, MRC-SS), SOC-Refractory group (N=12), Interim Analysis at 50% of total sample size. The dashed lines represent the minimal clinically important difference (MCID) cutoff established in the field (2021 EAN/PNS guidelines).
Figure 19:
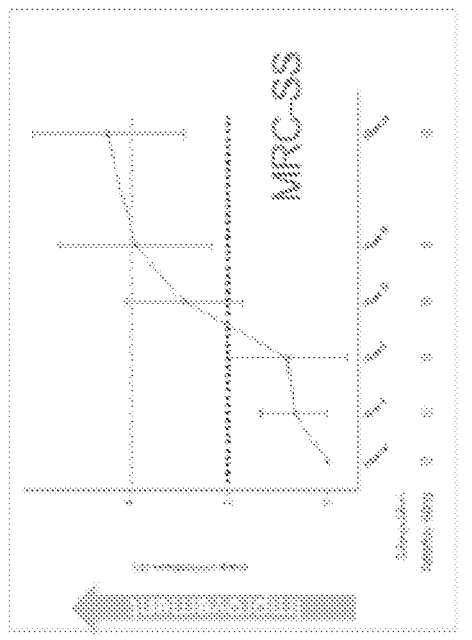
Figure 19:
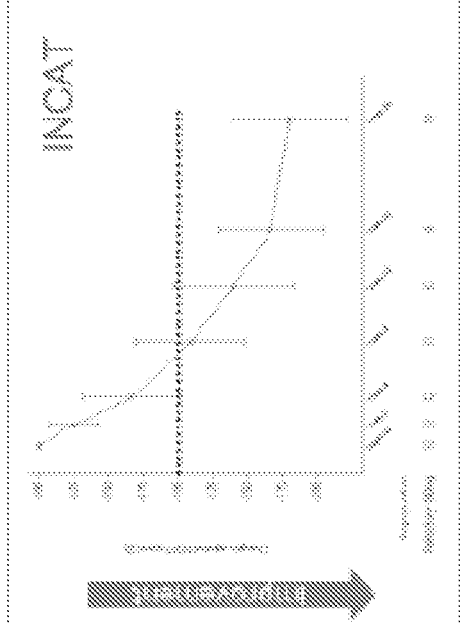
Figure 19:
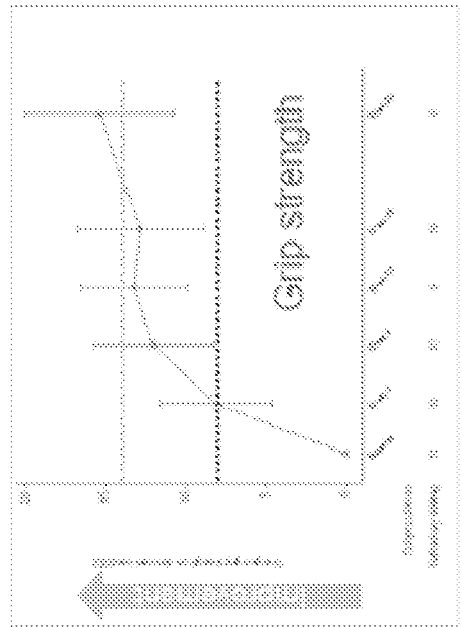
Figure 20:
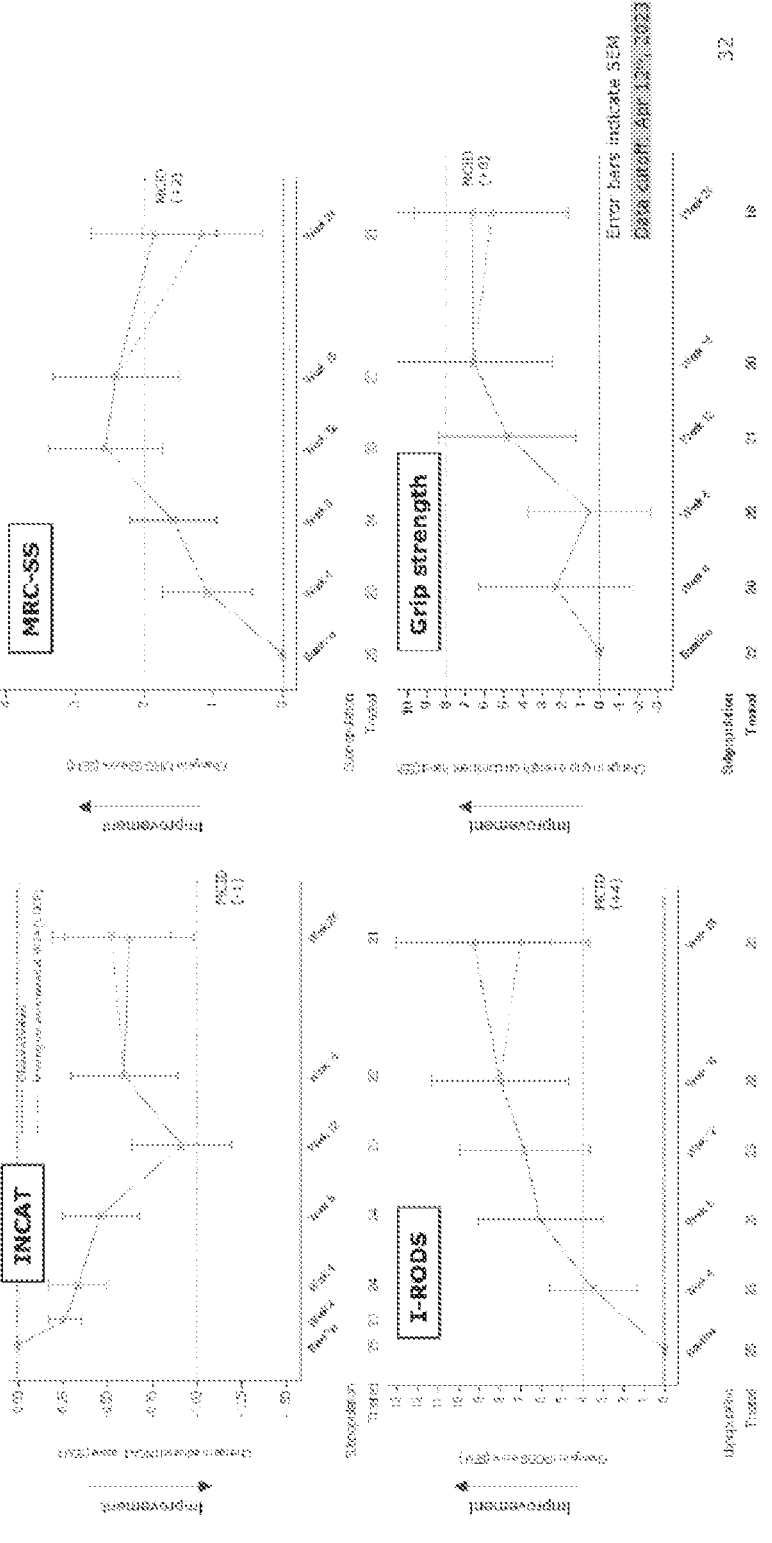
FIG. 20 shows change from baseline in the key clinical outcome measures evaluating functional disability (INCAT disability score, I-RODS) and impairment (grip strength, MRC-SS), SOC-Treated group (N=25), Interim Analysis at 50% of total sample size. The dashed lines represent the minimal clinically important difference (MCID) cutoff established in the field (2021 EAN/PNS guidelines).

Additional clinical efficacy results are shown in FIGS. 19 and 20. FIGS. 19 and 20 depict group data corresponding to change from baseline in the key clinical outcome measures evaluating functional disability (INCAT disability score, I-RODS) and impairment (grip strength, MRC-SS) for the SOC-Refractory and SOC-Treated groups, respectively. Results show internal consistency, with improvements across outcome measures that follow the expected directionality compatible with a positive effect (consistent decrease in INCAT disability score over time, combined with a consistent increase in I-RODS, grip strength and MRC-SS over time). The magnitude of response observed in the analyses suggests a robust effect, as it goes beyond the minimal clinically important difference (MCID) thresholds established in the field. As per consensus, these MCID thresholds are: adjusted INCAT adjusted score: at least 1 point; I-RODS: at least 4 points; grip strength: at least 8-14 kPa, and MRC sum score (MRCSS): at least 2-4 points (2021 EAN/PNS CIDP guidelines, Van den Bergh et al. J Peripher Nery Syst. 2021; 26(3):242-268).

Figure 18:
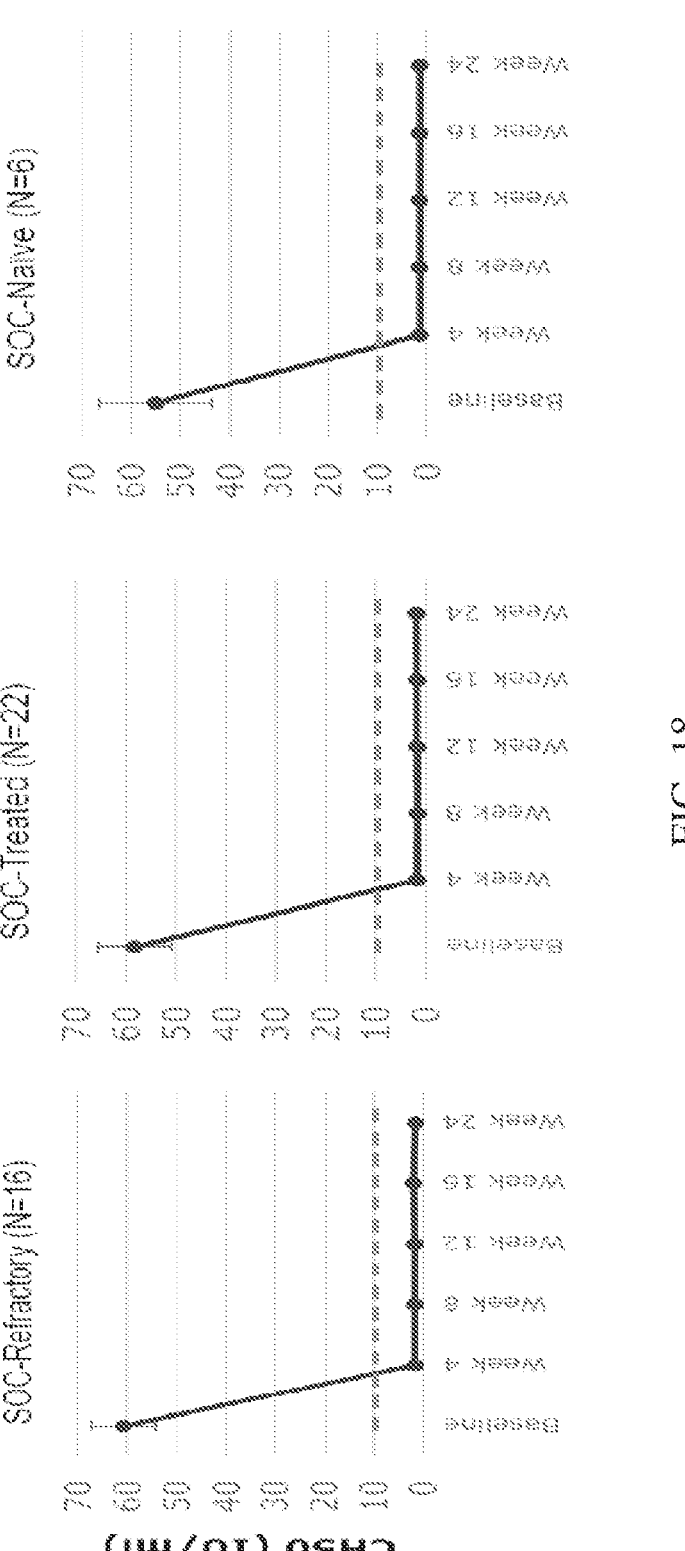
FIG. 18 shows complement inhibition (CH50 biomarker) in SOC-Refractory (N=16), SOC-Treated (N=22), and SOC-Naïve (N=6) patients. Dashed lines indicate expected level of complement deficiency based on sutimlimab (<10 IU/ml cutoff). Data include all available patients/timepoints at the time of cutoff. Error bars represent SD.

Results with complement biomarker CH50 are shown in FIG. 18. Data suggest that the dose being tested in PDY16744, 50 mg/kg IV load followed by 600 mg SC weekly, provides strong and sustained inhibition of complement activity in blood to an extent ($\leq$10 IU/ml, $\geq$90% inhibition) that is expected to translate into beneficial clinical effects, based on extrapolation of a related C1s-targeting compound, Sutimlimab, in patients with CAD (Jager et al. Blood. 2019 Feb. 28; 133(9):893-901).

Aside from the two interim analyses, preliminary results for 6 SOC-Naïve patients from the Phase 2 study indicate that the tested dosage regimens are effective, with 2 responses observed out of 5 completers at the time of cutoff. Overall, 2 patients who had reached 24 weeks responded to the treatment, while one responsive patient discontinued the study for reasons unrelated to the treatment.

Additional Proposed Dose Regimens

Participants are administered a one-time 50 mg/kg IV loading dose on Day 1 and receive SC doses administered with a syringe, or pre-filled syringe, or autoinjector, or large-volume drug delivery system. Possible administered SC doses include 300 mg qw, 600 mg qw, 600 mg q2w, 1200 mg q2w, 1200 mg q4w, 2400 mg q4w, 3600 mg q12w, or 7200 mg q12w. Participants receive SC doses administered regularly with a syringe, or pre-filled syringe, or autoinjector, or large-volume drug delivery system until end of treatment.

TABLE 13

Summary of proposed dose regimens and predicted SAR445088 Ctrough during treatment with a large volume subcutaneous device and a 50 mg/kg IV loading dose.

| | SAR445088 Ctrough (ug/mL) for dose regimens with 50 mg/kg IV loading dose and large volume SC device | | | | | |
|---|---|---|---|---|---|---|
| Time (Wks) | +D 8 600 qw | +D 8 300 qw | +D 29 2400 q4w | +D 29 1200 q4w | +D 8 1200 q2w | +D 8 600 q2w |
| 4 | 358 | 328 | 348 | 324 | 384 | 333 |
| 8 | 530 | 597 | 372 | 399 | 518 | 375 |
| 12 | 647 | 574 | 402 | 436 | 631 | 413 |
| 16 | 745 | 550 | 457 | 466 | 726 | 443 |
| 20 | 821 | 534 | 511 | 487 | 761 | 466 |
| 24 | 840 | 529 | 661 | 472 | 820 | 487 |
| 28 | 857 | 526 | 730 | 460 | 837 | 487 |
| 32 | 865 | 523 | 770 | 483 | 837 | 490 |
| 36 | 883 | 521 | 830 | 466 | 837 | 488 |
| 40 | 890 | 521 | 830 | 474 | 837 | 486 |
| 44 | 890 | 520 | 830 | 480 | 837 | 486 |
| 48 | 890 | 520 | 860 | 479 | 837 | 487 |

Figure 21A:
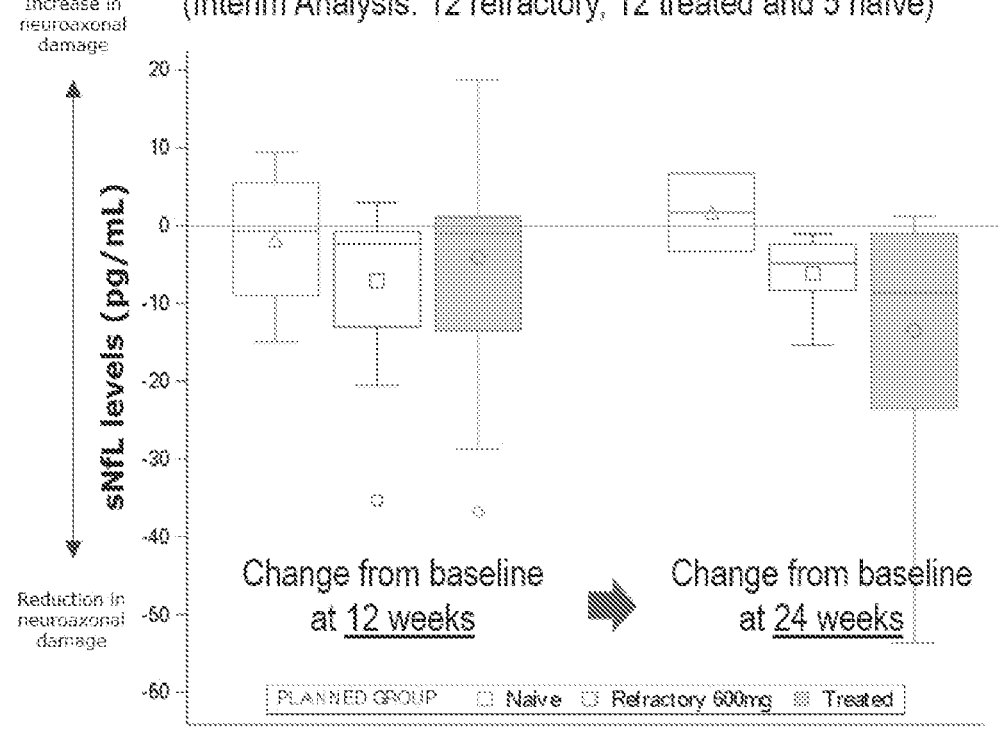
FIGS. 21A-21B show change from baseline in serum NfL levels.
Figure 21B:
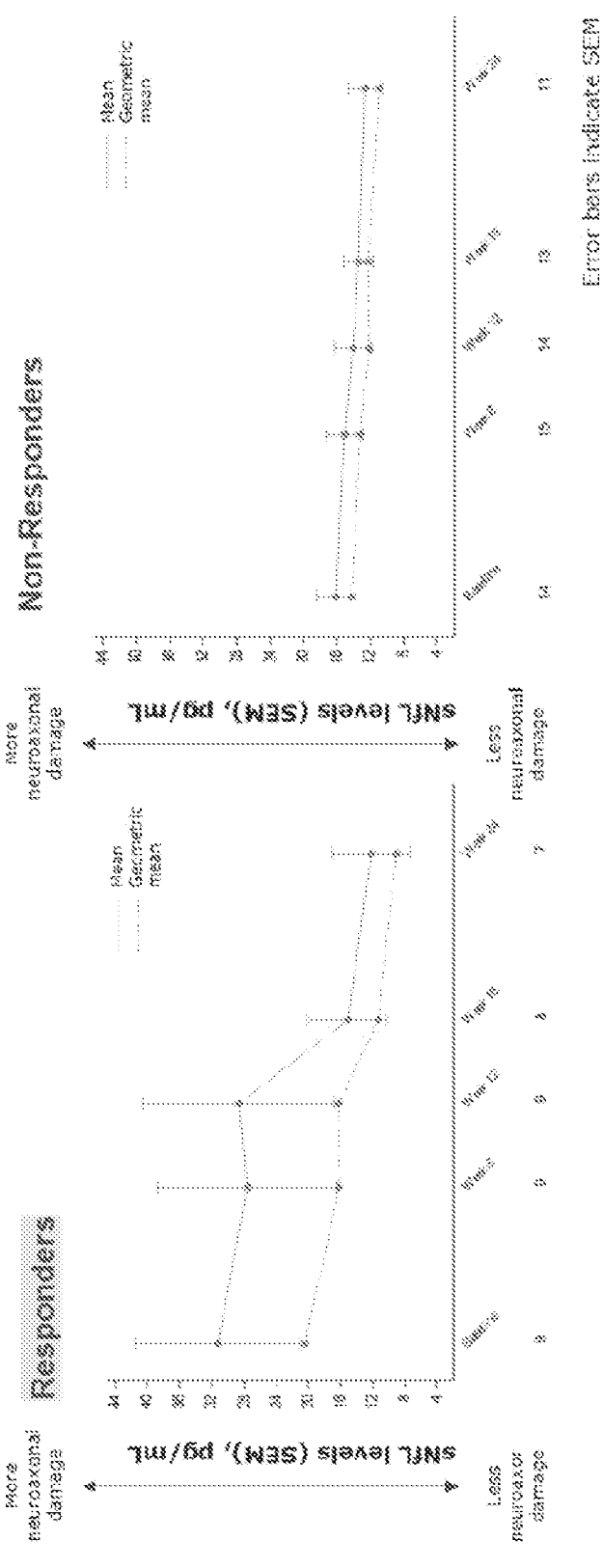

Last, preliminary data with serum neurofilament light chain (NfL) levels (FIGS. 21A, 21B) indicate a trend for reduction over time that mirrors the effects observed with the clinical outcomes. NfL is an objective biomarker of neuroaxonal damage that has emerged as a potential biomarker of disease activity in autoimmune neuropathies, particularly CIDP (van Lieverloo et al. J Peripher Nery Syst. 2019 June; 24(2):187-194).

Altogether, interim data from the ongoing Phase 2 study PDY16744 are promising and support that SAR445088 can address the unmet treatment needs of patients with CIDP. As a potential limitation of the data, PDY16744 study is an open label uncontrolled study, thus it is unclear to what extent placebo effect could play a role. However, the response rates observed in the study are clearly superior than the placebo rates that have been historically reported in published trials in CIDP, which are in the range of 11% for trials that used response/improvement as an endpoint (meta-analysis Lewis et al. J Peripher Nery Syst. 2020 September; 25(3): 230-237). This is also the case for the observed 12% relapse rate in SOC-Treated group (versus the historical 43% placebo relapse rate). Additionally, the combination of magnitude of effect, directionality across outcome measures, and correlation with objective biomarker effects also support the interpretation that the results are robust and unlikely driven by placebo.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between and including the upper and lower ends of the range are specifically contemplated and described herein.

What is claimed is:

1. A method for treating chronic inflammatory demyelinating polyneuropathy (CIDP) in a subject in need thereof, the method comprising:

administering to the subject a loading dose of about 50 mg/kg of the subject's body weight of a humanized antibody that specifically binds complement component C1s, and one or more maintenance doses of about 300 mg, about 600 mg, about 1,200 mg, about 2,400 mg, about 3,600 mg, or about 7,200 mg of the antibody, wherein the antibody comprises: a light chain (LC) complementarity determining region (CDR) 1 comprising the amino acid sequence of SEQ ID NO: 1, a LC CDR2 comprising the amino acid sequence of SEQ ID NO: 2, and a LC CDR3 comprising the amino acid sequence of SEQ ID NO: 3; and a heavy chain (HC) CDR1 comprising the amino acid sequence of SEQ ID NO: 4, an HC CDR2 comprising the amino acid sequence of SEQ ID NO: 5, and an HC CDR3 comprising the amino acid sequence of SEQ ID NO: 6.

2. The method of claim 1, wherein the one or more maintenance doses are administered about every 1, 2, 4, or 12 weeks thereafter.

3. The method of claim 1, wherein the loading dose is administered intravenously on Day 1, followed by subcutaneous administration of the maintenance dose about every week starting on Day 8.

4. The method of claim 1, wherein the subject has received another CIDP treatment prior to the loading dose or is concomitantly receiving another CIDP treatment.

5. The method of claim 1, wherein the subject has not received another treatment for CIDP within about 6 months prior to the loading dose.

6. The method of claim 1, wherein the antibody comprises a light chain variable region (VL) comprising the amino acid sequence of SEQ ID NO: 7 and a heavy chain variable region (VH) comprising the amino acid sequence of SEQ ID NO: 8.

7. The method of claim 1, wherein the antibody comprises a heavy chain constant region of the isotype IgG4.

8. The method of claim 7, wherein the IgG4 constant region comprises a proline substitution, a glutamic acid substitution, a leucine substitution, and a serine substitution at amino acid residues 108, 115, 308, and 314, respectively, relative to the IgG4 constant region sequence of SEQ ID NO: 11.

9. The method of claim 1, wherein the antibody comprises a light chain comprising the amino acid sequence of SEQ ID NO: 9 and a heavy chain comprising the amino acid sequence of SEQ ID NO: 10.

10. The method of claim 1, wherein the antibody is a Fab fragment, a F(ab')2 fragment, a scFv, or a Fv.

11. The method of claim 1, wherein the antibody is administered intravenously or subcutaneously.

12. The method of claim 1, wherein administration of the antibody results in a one point or greater decrease in adjusted Inflammatory Neuropathy Cause and Treatment (INCAT) disability score relative to the INCAT score prior to treatment with the antibody.

13. The method of claim 1, wherein following administration of the antibody, the subject has a plasma concentration of the antibody of at least about 100 μg/mL.

14. The method of claim 1, wherein the subject is refractory to another CIDP treatment.

15. The method of claim 1, wherein the antibody is administered using a syringe, a pre-filled syringe, or a large-volume drug delivery system.

16. The method of claim 1, wherein the antibody is administered using an autoinjector.

17. The method of claim 4, wherein the subject has received another CIDP treatment within about one week of the loading dose.

18. The method of claim 4, wherein the other CIDP treatment is intravenous immunoglobulin (IVIg), subcutaneous immunoglobulin (SCIg), or corticosteroids.

* * * * *

SEQUENCE LISTING

Sequence total quantity: 15
SEQ ID NO: 1                 moltype = AA   length = 15
FEATURE                      Location/Qualifiers
REGION                       1..15
                             note = Synthetic
source                       1..15
                             mol_type = protein
                             organism = synthetic construct
SEQUENCE: 1
KASQSVDYDG DSYMN                                                          15

SEQ ID NO: 2                 moltype = AA   length = 7
FEATURE                      Location/Qualifiers
REGION                       1..7
                             note = Synthetic
source                       1..7
                             mol_type = protein
                             organism = synthetic construct
SEQUENCE: 2
DASNLES                                                                   7

SEQ ID NO: 3                 moltype = AA   length = 9
FEATURE                      Location/Qualifiers
REGION                       1..9
                             note = Synthetic
source                       1..9
                             mol_type = protein
                             organism = synthetic construct
SEQUENCE: 3
QQSNEDPWT                                                                 9

SEQ ID NO: 4                 moltype = AA   length = 5
FEATURE                      Location/Qualifiers
REGION                       1..5
                             note = Synthetic
source                       1..5
                             mol_type = protein
                             organism = synthetic construct
SEQUENCE: 4
DDYIH                                                                     5

SEQ ID NO: 5                 moltype = AA   length = 17
FEATURE                      Location/Qualifiers
REGION                       1..17
                             note = Synthetic
source                       1..17
                             mol_type = protein
                             organism = synthetic construct
SEQUENCE: 5
RIDPADGHTK YAPKFQV                                                        17

SEQ ID NO: 6                 moltype = AA   length = 10
FEATURE                      Location/Qualifiers
REGION                       1..10
                             note = Synthetic
source                       1..10
                             mol_type = protein
                             organism = synthetic construct
SEQUENCE: 6
YGYGREVFDY                                                                10

SEQ ID NO: 7                 moltype = AA   length = 111
FEATURE                      Location/Qualifiers
REGION                       1..111
                             note = Synthetic
source                       1..111
                             mol_type = protein
                             organism = synthetic construct
SEQUENCE: 7
DIVLTQSPDS LAVSLGERAT ISCKASQSVD YDGDSYMNWY QQKPGQPPKI LIYDASNLES   60
GIPARFSGSG SGTDFTLTIS SLEPEDFAIY YCQQSNEDPW TFGGGTKVEI K           111

SEQ ID NO: 8                 moltype = AA   length = 119
FEATURE                      Location/Qualifiers
REGION                       1..119
                             note = Synthetic
source                       1..119
                             mol_type = protein -continued

```
                            organism = synthetic construct
SEQUENCE: 8
QVQLVQSGAE VKKPGASVKL SCTASGFNIK DDYIHWVKQA PGQGLEWIGR IDPADGHTKY    60
APKFQVKVTI TADTSTSTAY LELSSLRSED TAVYYCARYG YGREVFDYWG QGTTVTVSS    119

SEQ ID NO: 9               moltype = AA   length = 218
FEATURE                    Location/Qualifiers
REGION                     1..218
                           note = Synthetic
source                     1..218
                           mol_type = protein
                           organism = synthetic construct
SEQUENCE: 9
DIVLTQSPDS LAVSLGERAT ISCKASQSVD YDGDSYMNWY QQKPGQPPKI LIYDASNLES    60
GIPARFSGSG SGTDFTLTIS SLEPEDFAIY YCQQSNEDPW TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 10              moltype = AA   length = 446
FEATURE                    Location/Qualifiers
REGION                     1..446
                           note = Synthetic
source                     1..446
                           mol_type = protein
                           organism = synthetic construct
SEQUENCE: 10
QVQLVQSGAE VKKPGASVKL SCTASGFNIK DDYIHWVKQA PGQGLEWIGR IDPADGHTKY    60
APKFQVKVTI TADTSTSTAY LELSSLRSED TAVYYCARYG YGREVFDYWG QGTTVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVLHEA LHSHYTQKSL SLSLGK                                        446

SEQ ID NO: 11              moltype = AA   length = 327
FEATURE                    Location/Qualifiers
source                     1..327
                           mol_type = protein
                           organism = Homo sapiens
SEQUENCE: 11
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 12              moltype = AA   length = 327
FEATURE                    Location/Qualifiers
REGION                     1..327
                           note = Synthetic
source                     1..327
                           mol_type = protein
                           organism = synthetic construct
SEQUENCE: 12
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 13              moltype = AA   length = 327
FEATURE                    Location/Qualifiers
REGION                     1..327
                           note = Synthetic
source                     1..327
                           mol_type = protein
                           organism = synthetic construct
SEQUENCE: 13
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVLHE ALHSHYTQKS LSLSLGK                                       327

SEQ ID NO: 14              moltype = AA   length = 107
```

-continued

```
FEATURE              Location/Qualifiers
REGION               1..107
                     note = Synthetic
source               1..107
                     mol_type = protein
                     organism = synthetic construct
SEQUENCE: 14
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 15        moltype = AA  length = 673
FEATURE              Location/Qualifiers
source               1..673
                     mol_type = protein
                     organism = Homo sapiens
SEQUENCE: 15
EPTMYGEILS PNYPQAYPSE VEKSWDIEVP EGYGIHLYFT HLDIELSENC AYDSVQIISG  60
DTEEGRLCGQ RSSNNPHSPI VEEFQVPYNK LQVIFKSDFS NEERFTGFAA YYVATDINEC 120
TDFVDVPCSH FCNNFIGGYF CSCPPEYFLH DDMKNCGVNC SGDVFTALIG EIASPNYPKP 180
YPENSRCEYQ IRLEKGFQVV VTLRREDFDV EAADSAGNCL DSLVFVAGDR QFGPYCGHGF 240
PGPLNIETKS NALDIIFQTD LTGQKKGWKL RYHGDPMPCP KEDTPNSVWE PAKAKYVFRD 300
VVQITCLDGF EVVEGRVGAT SFYSTCQSNG KWSNSKLKCQ PVDCGIPESI ENGKVEDPES 360
TLFGSVIRYT CEEPYYYMEN GGGGEYHCAG NGSWVNEVLG PELPKCVPVC GVPREPFEEK 420
QRIIGGSDAD IKNFPWQVFF DNPWAGGALI NEYWVLTAAH VVEGNREPTM YVGSTSVQTS 480
RLAKSKMLTP EHVFIHPGWK LLEVPEGRTN FDNDIALVRL KDPVKMGPTV SPICLPGTSS 540
DYNLMDGDLG LISGWGRTEK RDRAVRLKAA RLPVAPLRKC KEVKVEKPTA DAEAYVFTPN 600
MICAGGEKGM DSCKGDSGGA FAVQDPNDKT KFYAAGLVSW GPQCGTYGLY TRVKNYVDWI 660
MKTMQENSTP RED                                                   673
```